(12) United States Patent
Li et al.

(10) Patent No.: US 10,494,384 B2
(45) Date of Patent: Dec. 3, 2019

(54) UREA PEPTOID BORIC ACID COMPOUND, PHARMACEUTICAL COMPOSITION THEREOF, PREPARATION METHOD THEREFOR, AND USES THEREOF

(71) Applicants: Peking University, Beijing (CN); Zhengzhou Granlen Pharmatech. Ltd., Henan (CN)

(72) Inventors: Runtao Li, Beijing (CN); Haoyun An, Beijing (CN); Liqiang Han, Beijing (CN); Zemei Ge, Beijing (CN); Jingrong Cui, Beijing (CN); Tieming Cheng, Beijing (CN)

(73) Assignees: Peking University, Beijing (CN); Zhengzhou Granlen Pharmatech. Ltd., Henan (CN)

( * ) Notice: Subject to any disclaimer, the term of this patent is extended or adjusted under 35 U.S.C. 154(b) by 0 days.

(21) Appl. No.: 15/767,945

(22) PCT Filed: Sep. 22, 2016

(86) PCT No.: PCT/CN2016/099713
§ 371 (c)(1),
(2) Date: Apr. 12, 2018

(87) PCT Pub. No.: WO2017/063491
PCT Pub. Date: Apr. 20, 2017

(65) Prior Publication Data
US 2018/0298036 A1    Oct. 18, 2018

(30) Foreign Application Priority Data
Oct. 15, 2015    (CN) .......................... 2015 1 0665219

(51) Int. Cl.
| C07F 5/04 | (2006.01) |
| C07K 5/02 | (2006.01) |
| C07K 5/08 | (2006.01) |
| C07F 5/02 | (2006.01) |
| A61P 35/00 | (2006.01) |

(52) U.S. Cl.
CPC .............. *C07F 5/025* (2013.01); *A61P 35/00* (2018.01); *C07K 5/02* (2013.01); *C07K 5/08* (2013.01); *C07F 5/04* (2013.01)

(58) Field of Classification Search
CPC ... C07F 5/04; C07F 5/025; C07K 5/02; C07K 5/08
See application file for complete search history.

(56) References Cited

U.S. PATENT DOCUMENTS 7,576,206 B2 * 8/2009 Bernardini .............. C07F 5/025
546/13

FOREIGN PATENT DOCUMENTS

| CN | 1168633 A | 12/1997 |
| CN | 1867572 A | 11/2006 |
| CN | 101120006 A | 2/2008 |
| CN | 101247799 A | 8/2008 |
| CN | 102892417 A | 1/2013 |
| CN | 103945856 A | 7/2014 |
| CN | 106008572 A | 10/2016 |
| WO | WO 03/059898 A2 | 7/2003 |

OTHER PUBLICATIONS

Chemical Abstracts Registry No. 179324-16-4, indexed in the Registry file on STN CAS Online on Aug. 9, 1996. (Year: 1996).*
Basak, Subhash C. et al., "Quantitative structure-activity relationship studies of boron-containing dipeptide proteasome inhibitors using calculated mathematical descriptors" J Math Chem, 2011, pp. 185-200, vol. 49.
Zhu, Yong-Qiang et al., "3D-QSAR studies of boron-containing dipeptides as proteasome inhibitors with CoMFA and CoMSIA methods" European Journal of Medicinal Chemistry, 2009, pp. 1486-1499, vol. 44.
"Study of Aliphatic Substituted Urea Syntheses" May 2015.
International Search Report for PCT/CN2016/099713 dated Dec. 27, 2016.
Han, Li-Qiang et al., "Urea-containing peptide boronic acids as potent proteasome inhibitors" European Journal of Medicinal Chemistry, 2017, pp. 925-938, vol. 125.
Supplementary European Search Report for EP 16854873 dated Jun. 11, 2019.

* cited by examiner

*Primary Examiner* — Laura L Stockton
(74) *Attorney, Agent, or Firm* — Knobbe Martens Olson & Bear LLP

(57) ABSTRACT

The present invention provides a urea peptidomimetic boronic compound and pharmaceutical compositions thereof, their preparative methods and uses. The compounds are represented by the following formula (I).

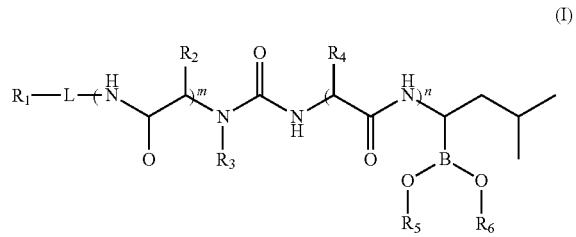

8 Claims, No Drawings

UREA PEPTOID BORIC ACID COMPOUND, PHARMACEUTICAL COMPOSITION THEREOF, PREPARATION METHOD THEREFOR, AND USES THEREOF

FIELD OF THE INVENTION

The present invention belongs to pharmaceutical field, involving a urea peptidomimetic boronic compound and pharmaceutical compositions thereof, their preparative methods and uses.

BACKGROUND OF THE INVENTION

Ubiquitin-proteasome pathway is responsible for the degradation of various intracorporal tissue proteins, most of which are closely related to physiological functions, thus the pathway plays a role of regulating various cellular mechanisms. When these physiological function or processes become abnormal, a variety of diseases will appear, such as tumor, inflammation, some neurodegenerative diseases, and so on. Therefore, the proteasome has been considered to be a very potential novel target for antitumor drugs. Peptide boronic compound of bortezomib (PS-341) was the first listed proteasome inhibitor approved by FDA, clinically used for the treatment of multiple myeloma. Since then, the research of peptide boronic proteasomes is highly valued. As the research of peptide proteasome inhibitors moves towards increasing sophistication, it is found that peptide boronic compounds are accompanied by a lot of disadvantages such as laggard synthetic process, poor metabolic stability, narrow antitumor spectra, severe toxic side effects, highlighted drug resistance and so on. Therefore, novel proteasome inhibitors are urgent to be found.

DESCRIPTION OF THE INVENTION

To solve the problems above, the present invention provides a novel urea peptidomimetic boronic compound. The present invention overcomes the synthetic difficulties of alpha-amino boronic acid compounds as key intermediates in the synthetic route of bortezomib, and difficulties of tough separation and purification process accompanied with boronic end-products. In addition, antitumor activities of the novel urea peptidomimetic boronic compounds are fully confirmed by a lot of experiments.

In a first aspect, the present invention provides a compound of formula (I):

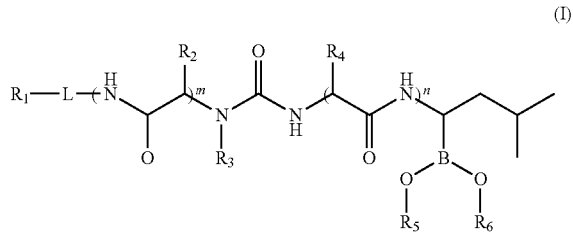

(I)

or a pharmaceutically acceptable salt or solvate thereof, wherein:
m and n represent the number of amino acid residues, independently selected from 0, 1, 2, and are not zero at the same time;
linker group L is alkylene;

$R_1$ is selected from the group consisting of aryl, heteroaryl, cycloalkyl, cycloalkenyl and heterocyclyl, wherein the above aryl, heteroaryl, cycloalkyl, cycloalkenyl or heterocyclyl each can be optionally substituted by one or more substituents independently selected from the group consisting of alkyl, cycloalkyl, alkenyl, cycloalkenyl, alkynyl, aryl, aralkyl, heteroaryl, heteroaralkyl, heterocyclyl, heterocycloalkyl, alkoxy, cycloalkoxy, aryloxy, heteroaryloxy, heterocycloxy, aralkoxy, heteroaralkoxy, heterocycloalkoxy, alkylthio, cycloalkylthio, arylthio, alkoxycarbonyl, aryloxycarbonyl, acyl, thioacyl, acyloxy, amido, carbamido, sulfinyl, alkylsulfonyl, arylsulfonyl, haloalkyl, carbamoyl, halogen, cyano, isocyano, nitro, nitroso, thiocyano, isothiocyano, acylhydrazino, thioalkyl, sulpho and silyl;

$R_2$ and $R_4$ are side chains of amino acids, m of $R_2$ and n of $R_4$ are independently selected from hydrogen, aralkyl, heteroaralkyl, heterocycloalkyl, alkyl, wherein the above aralkyl, heteroaralkyl, heterocycloalkyl or alkyl each can be optionally substituted by one or more substituents independently selected from the group consisting of alkyl, cycloalkyl, alkenyl, cycloalkenyl, alkynyl, aryl, aralkyl, heteroaryl, heteroaralkyl, heterocyclyl, heterocycloalkyl, alkoxy, cycloalkoxy, aryloxy, alkylthio, cycloalkylthio, arylthio, alkoxycarbonyl, aryloxycarbonyl, acyl, thioacyl, acyloxy, amido, carbamido, sulfinyl, alkylsulfonyl, arylsulfonyl, haloalkyl, carbamoyl, halogen, cyano, isocyano, nitro, nitroso, thiocyano, isothiocyano, acylhydrazino, thioalkyl, sulpho and silyl;

$R_3$ is hydrogen or alkyl;

$R_5$ and $R_6$ are hydrogen at the same time, or together $R_5$ and $R_6$ form diol ester group;

when m is 0, $R_1$, L and $R_3$ together with N atom to which L and $R_3$ are attached can alternatively form 5, 6 or 7 membered heterocyclic ring having, in addition to the nitrogen atom, another ring heteroatom selected from N, O and S, and optionally having an oxo group; meanwhile, the 5, 6 or 7 membered heterocyclic ring above is fused to aromatic ring or heteroaromatic ring each optionally substituted by one or more substituents independently selected from the group consisting of alkyl, cycloalkyl, alkenyl, cycloalkenyl, alkynyl, aryl, aralkyl, heteroaryl, heteroaralkyl, heterocyclyl, heterocycloalkyl, alkoxy, cycloalkoxy, aryloxy, alkylthio, cycloalkylthio, arylthio, alkoxycarbonyl, aryloxycarbonyl, acyl, thioacyl, acyloxy, amido, carbamido, sulfinyl, alkylsulfonyl, arylsulfonyl, haloalkyl, carbamoyl, halogen, cyano, isocyano, nitro, nitroso, thiocyano, isothiocyano, acylhydrazino, thioalkyl, sulpho and silyl.

Preferably, linker group L is $C_1$-$C_4$alkylene. More preferably, linker group L is methylene or ethylene.

Preferably, $R_1$ is selected from the group consisting of phenyl, naphthyl, heteroaryl and heterocyclyl, wherein the above phenyl, naphthyl, heteroaryl or heterocyclyl each can be optionally substituted by one or more substituents independently selected from the group consisting of $C_1$-$C_4$ alkyl, aryl, aryl $C_1$-$C_4$ alkyl, heteroaryl, heteroaryl $C_1$-$C_4$ alkyl, heterocyclyl, heterocyclyl $C_1$-$C_4$ alkyl, $C_1$-$C_4$ alkoxy, aryloxy, heteroaryloxy, heterocycloxy, aryl $C_1$-$C_4$ alkoxy, heteroaryl $C_1$-$C_4$ alkoxy, heterocyclyl $C_1$-$C_4$ alkoxy, halogen, cyano, isocyano, nitro, nitroso, thiocyano and isothiocyano. More preferably, $R_1$ is selected from the group consisting of phenyl, naphthyl, oxazolyl, isoxazolyl, imidazolyl, furanyl, indolyl, isoindolyl, pyrrolyl, triazolyl, triazinyl, tetrazolyl, thienyl, thiazolyl, isothiazolyl, pyridinyl, pyrimidinyl, pyrazinyl, pyridazinyl, benzofuranyl, benzothiazolyl, benzoxazolyl, benzimidazolyl, benzothienyl, benzopyranyl, carbazolyl, quinolyl, isoquinolyl, quinazolinyl, cinnolinyl, naphthyridinyl, pteridinyl, purinyl, quinoxalinyl, thiadiazolyl, indolizinyl, acridinyl, phenazinyl, phthalazinyl, coumarinyl, pyrazolo-pyridinyl, pyridino-pyridazinyl, pyrrolo-pyridinyl, imidazo-pyridinyl, pyrazolo-pyridazinyl, azepinyl, acridinyl, benzodioxolyl, benzodioxahexyl, benzodihydropyranyl, dioxolyl, dioxaphospholyl, decahydroisoquinolinyl, indanyl, indolinyl, isoindolinyl, isobenzodihydropyranyl, isothiazolidinyl, isoxazolidinyl, morpholinyl, oxazolinyl, oxazolidinyl, oxadiazolyl, 2-oxopiperazinyl, 2-oxopiperidyl, 2-oxopyrrolidinyl, 2-oxoazepinyl, octahydroindolyl, octahydroisoindolyl, perhydroazepinyl, piperazinyl, 4-piperidonyl, piperidyl, phenothiazinyl, phenoxazinyl, quinuclidinyl, tetrahydroisoquinolinyl, tetrahydrofuranyl, tetrahydropyranyl, pyrrolidinyl, thiazolinyl, thiazolidinyl, thiomorpholinyl, thiomorpholinyl sulfinyl and thiomorpholinyl sulfonyl, wherein the above groups each can be optionally substituted by one or more substituents independently selected from the group consisting of $C_1$-$C_4$alkyl, phenyl, phenyl $C_1$-$C_4$alkyl, heteroaryl, heteroaryl $C_1$-$C_4$ alkyl, heterocyclyl, heterocyclyl $C_1$-$C_4$ alkyl, $C_1$-$C_4$ alkoxy, phenoxy, heteroaryloxy, heterocycloxy, phenyl $C_1$-$C_4$ alkoxy, heteroaryl $C_1$-$C_4$ alkoxy, heterocyclyl $C_1$-$C_4$ alkoxy, fluorine, chlorine, bromine, iodine, cyano, isocyano, nitro, nitroso, thiocyano, isothiocyano. Most preferably, $R_1$ is selected from the group consisting of phenyl, naphthyl, furanyl, pyrazinyl and tetrahydrofuranyl, wherein the above groups each can be optionally substituted by one or more substituents independently selected from the group consisting of methyl, phenyl, benzyl, methoxy, phenoxy, benzyloxy, fluorine, chlorine, bromine, iodine, cyano, isocyano, nitro, nitroso, thiocyano and isothiocyano.

Preferably, m of $R_2$ and n of $R_4$ are independently selected from hydrogen, phenyl $C_1$-$C_4$ alkyl, heteroaryl $C_1$-$C_4$ alkyl, heterocyclyl $C_1$-$C_4$ alkyl, $C_1$-$C_4$ alkyl and naphthyl $C_1$-$C_4$ alkyl, wherein the above phenyl $C_1$-$C_4$ alkyl, heteroaryl $C_1$-$C_4$ alkyl, heterocyclyl $C_1$-$C_4$ alkyl, $C_1$-$C_4$ alkyl or naphthyl $C_1$-$C_4$ alkyl can be optionally substituted by one or more substituents independently selected from the group consisting of carbamoyl, nitro and nitroso. More preferably, m of $R_2$ and n of $R_4$ are independently selected from hydrogen, benzyl, isobutyl, s-butyl, isopropyl, methyl, carbamoylethyl, nitrobenzyl, phenylethyl, naphthylmethl and benzopyrrolylmethyl.

Preferably, $R_3$ is hydrogen or $C_1$-$C_4$ alkyl. More preferably, $R_3$ is hydrogen or methyl. Preferably, $R_5$ and $R_6$ are hydrogen at the same time, or together $R_5$ and $R_6$ form cyclic diol ester group. More preferably, $R_5$ and $R_6$ are hydrogen at the same time, or together $R_5$ and $R_6$ form pinanediol ester or pinacol ester group.

Preferably, when m is 0, $R_1$, L and $R_3$ together with N atom to which L and $R_3$ are attached can alternatively form 5, 6 or 7 membered heterocyclic ring having, in addition to the nitrogen atom, another ring heteroatom selected from N, O and S, and optionally having an oxo group; meanwhile, the 5, 6 or 7 membered heterocyclic ring above is fused to benzene ring, naphthalene ring or heteroaromatic ring, wherein the above benzene ring, naphthalene ring or heteroaromatic ring each optionally substituted by one or more substituents independently selected from the group consisting of alkyl, cycloalkyl, alkenyl, cycloalkenyl, alkynyl, aryl, aralkyl, heteroaryl, heteroaralkyl, heterocyclyl, heterocycloalkyl, alkoxy, cycloalkoxy, aryloxy, alkylthio, cycloalkylthio, arylthio, alkoxycarbonyl, aryloxycarbonyl, acyl, thioacyl, acyloxy, amido, carbamido, sulfinyl, alkylsulfonyl, arylsulfonyl, haloalkyl, carbamoyl, halogen, cyano, isocyano, nitro, nitroso, thiocyano, isothiocyano, acylhydrazino, thioalkyl, sulpho and silyl. More preferably, when m is 0, $R_1$, L and $R_3$ together with N atom to which L and $R_3$ are attached can alternatively form 5, 6 or 7 membered heterocyclic ring having, in addition to the nitrogen atom, another ring heteroatom selected from N, O and S, and optionally having an oxo group; meanwhile, the 5, 6 or 7 membered heterocyclic ring above is fused to benzene ring, naphthalene ring or heteroaromatic ring, wherein the above benzene ring, naphthalene ring or heteroaromatic ring can be optionally substituted by one or more substituents independently selected from the group consisting of $C_1$-$C_4$alkoxy, nitro and nitroso. Most preferably, when m is 0, $R_1$, L and $R_3$ together with N atom to which L and $R_3$ are attached can alternatively form piperidine ring, and optionally having an oxo group; meanwhile, the piperidine ring above is fused to benzene ring optionally substituted by one or more substituents independently selected from the group consisting of methoxy and nitro.

In a second aspect, the present invention provides a pharmaceutical composition comprising a compound or a pharmaceutically acceptable salt or solvate thereof according to the first aspect and a pharmaceutically acceptable carrier.

In a third aspect, the present invention provides a method for preparation of a compound according to the first aspect, comprising the steps of forming amido group, forming carbamido group by coupling; and optionally hydrolyzing the boronic pinacol ester; and optionally further esterifying the boronic acid with diol, preferably pinanediol.

In a fourth aspect, the present invention provides uses of the compound or a pharmaceutically acceptable salt or solvate thereof according to the first aspect in the preparation of pharmaceuticals used as proteasome inhibitors. According to a preferred embodiment, said pharmaceuticals used as proteasome inhibitors are used for treating cancer preferably selected from the group consisting of lung cancer, breast cancer, liver cancer, gastric cancer, cervical cancer, colon cancer, leukemia, ovarian cancer, pancreatic cancer and epithelial cancer.

Specific Embodiments of the Invention

As used herein, the term "alkyl" refers to a group consisting of carbon and hydrogen atoms only, without any units of unsaturation (e.g., double bond, triple bond, or cycle), including any possible geometric isomers and stereoisomers. An alkyl group attaches to the rest of a molecule through a single bond. Examples of alkyl include, but are not limited to, methyl, ethyl, n-propyl, isopropyl, n-butyl, isobutyl, s-butyl, t-butyl, n-pentyl and other seven isomers thereof, n-hexyl and other sixteen isomers thereof, n-heptyl and other isomers thereof, n-octyl and other isomers thereof, n-nonyl and other isomers thereof, n-decyl and other isomers thereof.

As used herein, the term "cycloalkyl" refers to a saturated non-aromatic carbocyclic group having at least 3 carbon atoms, which may be monocyclic, bicyclic, or polycyclic, and may be fused, bridged, or spiro. Examples of cycloalkyl include, but are not limited to, cyclopropyl, cyclobutyl, cyclopentyl, cyclohexyl, cycloheptyl, cyclooctyl, cyclononyl, cyclodecyl, and fused, bridged, or spiro rings formed by two or more monocyclic rings above via sharing bonds or atoms.

As used herein, the term "alkenyl" refers to a group where an alkyl group above (except methyl) has one or more double bonds.

As used herein, the term "cycloalkenyl" refers to a group where a cycloalkyl group above has one or more double bonds.

As used herein, the term "alkynyl" refers to a group where an alkyl group above (except methyl) has one or more triple bonds.

As used herein, the term "alkoxy" refers to a group where an alkyl group above connects to oxygen atom, through which it connects to the rest of a molecule via single bond, including any possible geometric isomers and stereoisomers. Examples of alkoxy include, but are not limited to, methoxy, ethoxy, n-propoxy, isopropoxy, n-butoxy, isobutoxy, s-butoxy, t-butoxy, n-pentoxy and other seven isomers thereof, n-hexyloxy and other isomers thereof, n-heptyloxy and other isomers thereof, n-octyloxy and other isomers thereof, n-nonyloxy and other isomers thereof, n-decyloxy and other isomers thereof.

As used herein, the term "aryl" refers to an aromatic carbocyclic group having at least 6 carbon atoms, which may be monocyclic, bicyclic, or polycyclic, wherein the bicyclic or polycyclic ring can be formed by monocyclic rings through a single bond connection or in a fused manner. Examples of aryl include, but are not limited to, phenyl, naphthyl, anthracyl, phenanthryl, indenyl, pyrenyl, perylenyl, azulenyl, pentalenyl, heptalenyl, acenaphthenyl, fluorenyl, phenalenyl, fluoranthenyl, acephenanthrylenyl, aceanthrylenyl, triphenylenyl, chrysenyl, naphthacenyl, picenyl, pentaphenyl, pentacenyl, tetraphenylenyl, hexaphenyl, hexacenyl, coronenyl, trinaphthylenyl, heptaphenyl, heptacenyl, pyranthrenyl, ovalenyl, biphenylyl, binaphthylyl.

As used herein, the term "heteroaryl" refers to a 5 to 14 membered aromatic heterocyclic group having one or more heteroatoms selected from the group consisting of N, O, S, which can be monocyclic, bicyclic, or polycyclic, wherein the bicyclic or polycyclic ring can be formed by monocyclic rings through a single bond connection or in a fused manner. Examples of heteroaryl include, but are not limited to, oxazolyl, isoxazolyl, imidazolyl, furanyl, indolyl, isoindolyl, pyrrolyl, triazolyl, triazinyl, tetrazolyl, thienyl, thiazolyl, isothiazolyl, pyridinyl, pyrimidinyl, pyrazinyl, pyridazinyl, benzofuranyl, benzothiazolyl, benzoxazolyl, benzimidazolyl, benzothienyl, benzopyranyl, carbazolyl, quinolyl, isoquinolyl, quinazolinyl, cinnolinyl, naphthyridinyl, pteridinyl, purinyl, quinoxalinyl, thiadiazolyl, indolizinyl, acridinyl, phenazinyl, phthalazinyl, coumarinyl, pyrazolopyridinyl, pyridino-pyridazinyl, pyrrolo-pyridinyl, imidazopyridinyl, pyrazolo-pyridazinyl, and groups formed by the above heteroaryl groups through a single bond connection or in a fused manner.

As used herein, the term "heterocyclyl" refers to a 3 to 15 membered non-aromatic heterocyclic group consisting of, in addition to carbon atoms, one or more heteroatoms selected from the group consisting of N, O, S, which can be monocyclic, bicyclic, or polycyclic, can be fused, bridged, or spiro, and can optionally contain one or more double bonds. Examples of heterocyclyl include, but are not limited to, azepinyl, acridinyl, benzodioxolyl, benzodioxahexyl, benzodihydropyranyl, dioxolyl, dioxaphospholyl, decahydroisoquinolinyl, indanyl, indolinyl, isoindolinyl, isobenzodihydropyranyl, isothiazolidinyl, isoxazolidinyl, morpholinyl, oxazolinyl, oxazolidinyl, oxadiazolyl, 2-oxopiperazinyl, 2-oxopiperidyl, 2-oxopyrrolidinyl, 2-oxoazepinyl, octahydroindolyl, octahydroisoindolyl, perhydroazepinyl, piperazinyl, 4-piperidonyl, piperidyl, phenothiazinyl, phenoxazinyl, quinuclidinyl, tetrahydroisoquinolinyl, tetrahydrofuranyl, tetrahydropyranyl, pyrrolidinyl, thiazolinyl, thiazolidinyl, thiomorpholinyl, thiomorpholinyl sulfinyl, thiomorpholinyl sulfonyl.

As used herein, the term "aralkyl" refers to an alkyl group in which one or more hydrogen atoms are replaced by an aryl group, wherein the alkyl group and aryl group are as previously defined.

As used herein, the term "heteroaralkyl" refers to an alkyl group in which one or more hydrogen atoms are replaced by a heteroaryl group, wherein the alkyl group and heteroaryl group are as previously defined.

As used herein, the term "halogen" or "halo" refers to fluorine, chlorine, bromine or iodine.

The pharmaceutical composition of the present invention contains a compound according to the first aspect as active ingredient. In addition, the pharmaceutical composition can also contain a pharmaceutical acceptable carrier, including but not limited to, water, brine solution, alcohol, polyethylene glycol, polyhydroxy-ethoxylated castor oil, peanut oil, olive oil, gelatin, lactose, gypsum powder, sucrose, dextrin, magnesium carbonate, sugar, cyclodextrin, amylose, magnesium stearate, talc, gelatin, agar, pectin, gum arabic, stearic acid or low alkyl cellulose ether, silicic acid, fatty acid, fatty-acid amine, fatty-acid monoglyceride and diglyceride, pentaerythritol fatty-acid ether, polyoxyethylene, hydroxymethyl cellulose and polyvinylpyrrolidone. The pharmaceutical composition can also contain one or more pharmaceutical acceptable adjuvants, wetting agents, emulsifiers, suspending agents, preservatives, osmotic pressure regulators, buffering agents, sweetening agents, flavoring agents, coloring agents or any combinations of the above.

The pharmaceutical composition of the present invention can be produced into any dosage forms, such as capsule, tablet, aerosol, solution, suspension, sugar coating agent, lozenge, syrup, emulsion, soft ointment, ointment, injection, powder, granule, paste, sustained-release agent, foaming agent. According to different routes of administration, the pharmaceutical composition of the present invention can be produced into oral administration preparations, nasal administration preparations, pulmonary administration preparations, buccal administration preparations, subcutaneous administration preparations, intradermal administration preparations, transdermal administration preparations, parenteral administration preparations, rectal administration preparations, repository administration preparations, intravenous administration preparations, intraurethral administration preparations, intramuscular administration preparations, intranasal administration preparations, ophthalmic administration preparations, epidural administration preparations or topical administration preparations.

As used herein, the term "cancer" refers to various known cancers in this field, including, but not limited to, lung cancer, liver cancer, gastric cancer, cervical cancer, colon cancer, breast cancer, leukemia, non-small cell carcinoma, prostate cancer or melanoma, brain cancer, skin cancer, bone cancer, lymphoma, nasopharyngeal carcinoma, laryngeal cancer, esophageal cancer, duodenal carcinoma, small intestine carcinoma, large intestine carcinoma, pancreatic cancer, kidney cancer, genital cancer, thyroid cancer.

EXAMPLES

The following examples are used for further detailed illustration of the present invention, but the present invention is not limited to these examples.

In a typical example, compounds of the present invention are synthesized by the following methods, wherein various substituents are defined as formula (I).

Example 1

N-L-leucine borate-N'-(p-methoxy-benzylcarbamoyl)-L-phenylalanine-urea (hlq-U51)

Synthesis of Intermediate a: N-Boc-L-phenylalanyl-p-methoxy-benzylamine

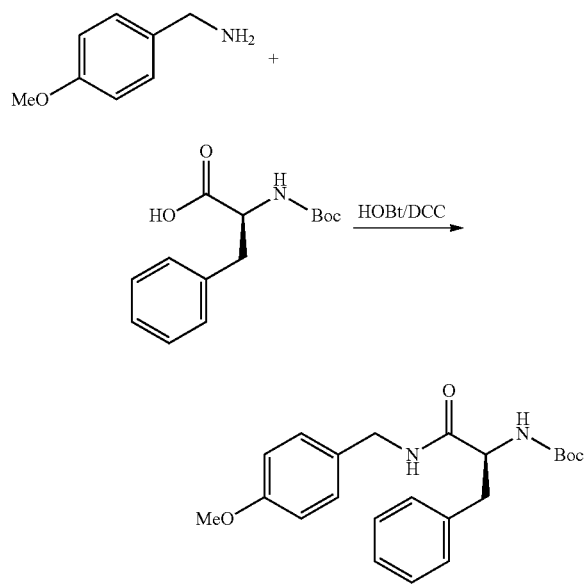

To a stirred solution of N-Boc-L-phenylalanine (2.65 g, 10 mmol) in THF (50 mL) was added HOBt (1.48 g, 11.0 mmol), following by addition of DCC (2.47 g, 12.0 mmol) after 5 min. After 30 min of carboxyl activation, the reacting system became milky white suspension, then p-methoxy-benzylamine (1.3 mL, 10 mmol) and N-methylmorpholine (1.32 mL, 12 mmol) were added. The mixture was allowed to stir for another 24 h at room temperature, and the reaction was showed to be complete with TLC monitoring. Insoluble N,N'-dicyclohexylurea (DCU) was removed by filtration, then the solvent of THF was evaporated under reduced pressure. The residue was dissolved in 50 mL of ethyl acetate, washed with 5% NaHCO$_3$, 10% citric acid, 5% NaHCO$_3$ and saturated brine, then dried over anhydrous Na$_2$SO$_4$. The crude product was purified by silica gel chromatography (ethyl acetate:petroleum ether=1:3) to afford 2.84 g of white solid product with a yield of 74%, mp: 68-71° C.

$^1$H NMR (400 MHz, CDCl$_3$) δ 7.33-7.11 (m, 5H), 7.00 (d, J=7.1 Hz, 2H), 6.77 (d, J=8.5 Hz, 2H), 6.40 (s, 1H), 5.26 (d, J=6.7 Hz, 1H), 4.40 (d, J=17.7 Hz, 1H), 4.24 (qd, J=14.4, 5.2 Hz, 2H), 3.75 (s, 3H), 3.04 (d, J=6.1 Hz, 2H), 1.36 (s, 9H). $^{13}$C NMR (101 MHz, CDCl$_3$) δ 171.15, 158.93, 155.49, 136.81, 129.90, 129.37, 128.99, 128.60, 126.83, 113.95, 80.06, 55.26, 42.88, 38.77, 33.97, 28.27.

Synthesis of Intermediate b: N—HCl-L-phenylalanyl-p-methoxy-benzylamine

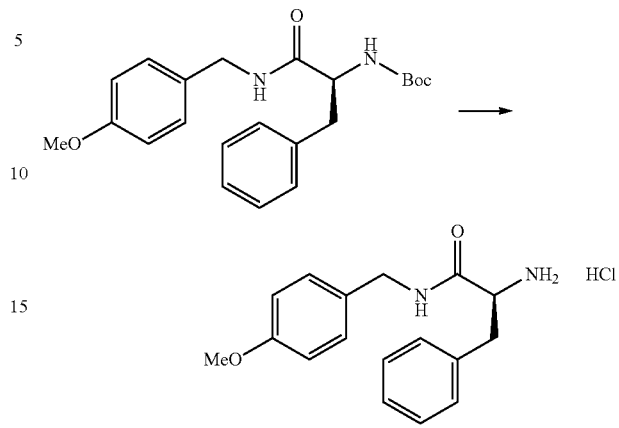

To a solution in an ice bath of intermediate a (2.66 g, 6.9 mmol) in CH$_2$Cl$_2$ (10 mL) was added dropwise a solution of 3-equiv. HCl in EtOH (10 M, 2 mL, 21 mmol) which is 3-equivalent. The mixture was allowed to slowly increase to room temperature and stand for 10 h until completion. All volatile components were evaporated to afford white solid obviously with green impurities. The residue was suspended in 20 mL of ethyl acetate, and after carefully scooping the solid, the mixture was vigorously stirred for 2 h. The solid was collected by suction filtration and dried to obtain 2.2 g (6.9 mmol) of white solid product with a yield of 99%, mp: 195-197° C.

Synthesis of Intermediate c: N-L-leucine borate pinacol ester-N'-(p-methoxy-benzylcarbamoyl)-L-phenylalanine-urea

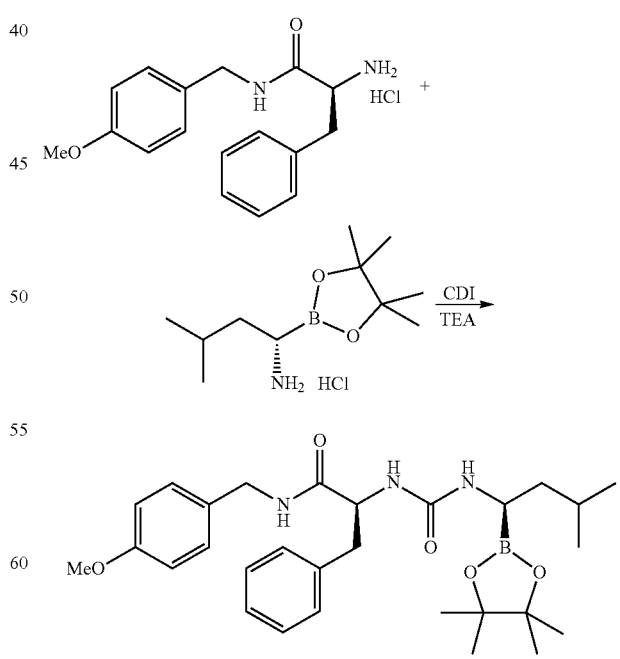

To a mixed solution of carbonyldiimidazole (CDI, 1.1 equiv, 0.49 g, 3.3 mmol) in DMF (8 mL) and acetonitrile (40 mL) was added L-leucine borate pinacol ester hydrochloride (0.75 g, 3 mmol) by portions, ensuring that the solid added last time was completely dissolved before every time of addition. The solution was reacted at room temperature for 2 h. Then intermediate b (0.96 g, 3 mmol) was added, followed by the addition of triethylamine (2 equiv., 0.83 mL, 6 mmol). The mixture became to be clarified and was reacted for another 24 h. The reaction was showed to be complete with TLC monitoring. Acetonitrile was removed carefully. To the residue was added ethyl acetate (50 mL) and distilled water (50 mL), the liquid was partitioned after fully shaking. The ethyl acetate layer was washed with brine (50 mL×2), and dried over Na$_2$SO$_4$. The solvent was evaporated to afford 1.2 g of crude product which was used in the next step without further purification.

Synthesis of the Title Compound: N-L-leucine borate-N'-(p-methoxy-benzylcarbamoyl)-L-phenylalanine-urea

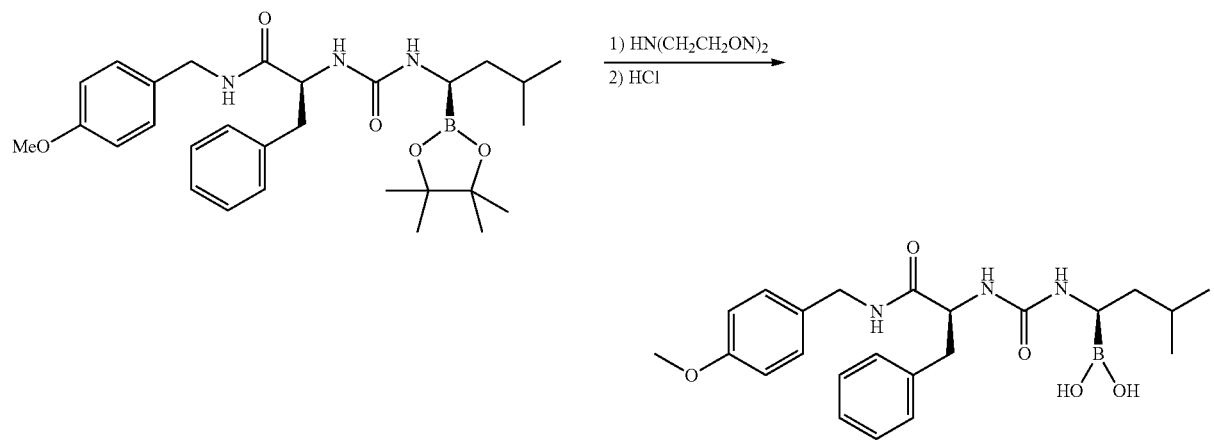

The previously obtained intermediate c (1.2 g) was dissolved in 40 mL of ethyl acetate and the solution was filtered. Diethanolamine (0.2 mL, 1.1 equiv) was added dropwise under stirring. The mixture was allowed to stir for 48 h at room temperature. The precipitate was collected by suction filtration and washed with ethyl acetate (20 mL×2), before suction to dry. The solid was suspended in ethyl acetate (20 mL), then distilled water (20 mL) and 4 N HCl (1 mL) was added. The mixture was vigorously stirred for 6 h and the reaction was completed. The water layer was removed by liquid partition, and the organic layer was washed with distilled water (50 mL×2), saturated brine (50 mL×2), then dried over Na$_2$SO$_4$. The solvent was evaporated to afford foam solid, which was recrystallized by ethyl acetate to obtain 120 mg of white solid product with a yield of 24%, mp: 128-135° C.

$^1$H NMR (400 MHz, DMSO) δ 8.36 (s, 1H), 6.82-7.21 (m, 10H), 4.34 (s, 1H), 4.17 (ddd, J=29.3, 14.6, 5.2 Hz, 2H), 3.71 (s, 3H), 3.07-2.69 (m, 2H), 1.67-1.42 (m, 1H), 1.37-1.04 (m, 2H), 0.79 (t, J=5.6 Hz, 6H). $^{13}$C NMR (101 MHz, DMSO) δ 158.65, 137.77, 131.28, 129.79, 128.95, 128.76, 128.53, 128.44, 126.79, 114.07, 55.49, 42.04, 41.99, 38.78, 25.78, 23.69, 23.29. HRMS (ESI) calcd for C$_{24}$H$_{33}$BN$_3$O$_4$: 438.25629 [(M−H$_2$O+CH$_2$+H)$^+$], found 438.25483.

Example 2

N-L-phenylalanyl-L-leucine borate-N'-pyrazin-2-ylmethylamine-urea (hlq-U78)

Synthesis of Intermediate a: N-L-phenylalanine methyl ester-N'-pyrazin-2-ylmethylamine-urea

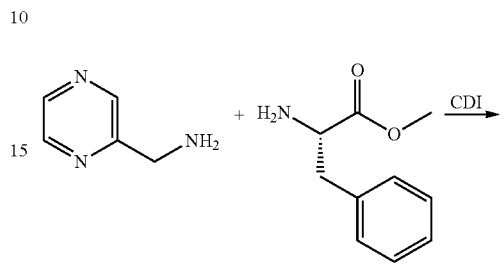

-continued

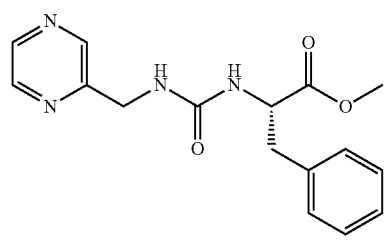

To a solution of carbonyldiimidazole (CDI, 1.64 g, 10.1 mmol) in DMF (8 mL) and acetonitrile (40 mL) was added L-phenylalanine methyl ester hydrochloride (1.98 g, 9.2 mmol) in portions, ensuring that the solid added last time was completely dissolved before every time of addition. The solution was reacted at room temperature for 2 h. Then pyrazin-2-ylmethylamine (1 g, 9.2 mmol) was added, followed by the addition of triethylamine (1.7 mL, 18.4 mmol). The mixture became to be clarified and was reacted for another 24 h. The reaction was showed to be complete with TLC monitoring. Acetonitrile was removed carefully. To the residue was added ethyl acetate (50 mL) and distilled water (50 mL), and the liquid was partitioned after fully shaking. The ethyl acetate layer was washed with saturated brine (50 mL×2), and dried over Na$_2$SO$_4$. The solvent was evaporated to afford crude product, which was recrystallized by mixture of ethyl acetate and diethyl ether to obtain 1.19 g of pure product with a yield of 42%, mp: 114-116° C.

$^1$H NMR (400 MHz, CDCl$_3$) δ 8.54 (s, 1H), 8.41 (d, J=2.5 Hz, 1H), 8.36 (d, J=1.6 Hz, 1H), 7.26-7.13 (m, 3H), 7.08 (d, J=6.8 Hz, 2H), 6.09 (d, J=12.7 Hz, 1H), 5.78 (d, J=14.9 Hz, 1H), 4.78 (dt, J=8.0, 6.0 Hz, 1H), 4.62-4.34 (m, 2H), 3.67 (s, 3H), 3.03 (qd, J=13.8, 6.1 Hz, 2H). $^{13}$C NMR (101 MHz, CDCl$_3$) δ 173.41, 157.51, 153.92, 143.94, 143.54, 143.21, 136.24, 129.29, 128.42, 126.91, 54.09, 52.20, 43.36, 38.42.

Synthesis of Intermediate b: N-L-phenylalanine-N'-pyrazin-2-ylmethylamine-urea

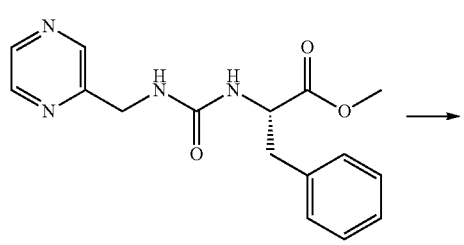

The previously obtained intermediate a (1.19 g, 3.51 mmol) was dissolved in 10 mL of THF. The solution was cooling down in an ice bath, and 2 N LiOH was added dropwise until a pH of 12-13, then the reaction was allowed to continue in an ice bath for 2 h until TLC monitoring showed that reaction was completed. Solvent of THF was evaporated slowly, and the residue in an ice bath was acidified to pH of 2-3 with hydrochloric acid, to afford plenty of white solid. The precipitate was collected by filtration, washed with water and diethyl ether, and then dried to obtain 0.9 g of white solid product with a yield of 77.8%, which was used in the next step directly.

Synthesis of Intermediate c: N-L-phenylalanyl-L-leucine borate pinacol ester-N'-pyrazin-2-ylmethylamine-urea

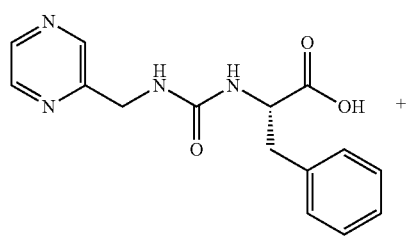

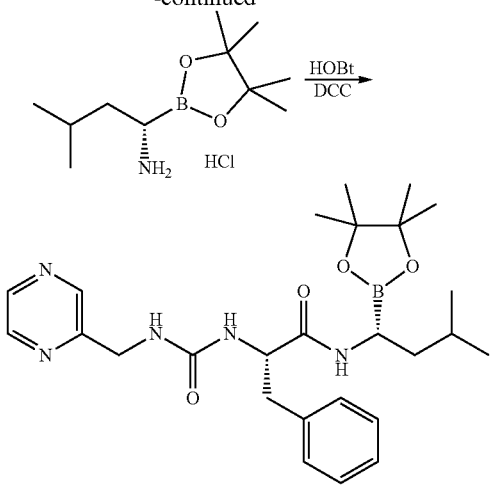

To a stirred suspension of previously obtained intermediate b (0.9 g, 3.0 mmol) in CH$_2$Cl$_2$ (50 mL) was added HOBt (0.45 g, 3.3 mmol), following by addition of DCC (0.74 g, 3.6 mmol) after 5 min. After 30 min of carboxyl activation, the reacting system became milky white suspension, then L-leucine borate pinacol ester hydrochloride (0.75 g, 3 mmol) and DIPEA (0.52 mL, 3 mmol) were added. The mixture was allowed to react for another 24 h at room temperature, and the reaction was showed to be complete with TLC monitoring. Insoluble N,N'-dicyclohexylurea (DCU) was removed by filtration, then the solvent of DCM was rotary-evaporated. The residue was dissolved in 50 mL of ethyl acetate, washed with 10% citric acid, 5% NaHCO$_3$ and saturated brine, then dried over anhydrous Na$_2$SO$_4$. The solvent of ethyl acetate was evaporated to afford 1.23 g of crude product as a faint yellow foam solid, which was used in the next step without further purification.

Synthesis of the Title Compound: N-L-phenylalanyl-L-leucine borate-N'-pyrazin-2-ylmethylamine-urea

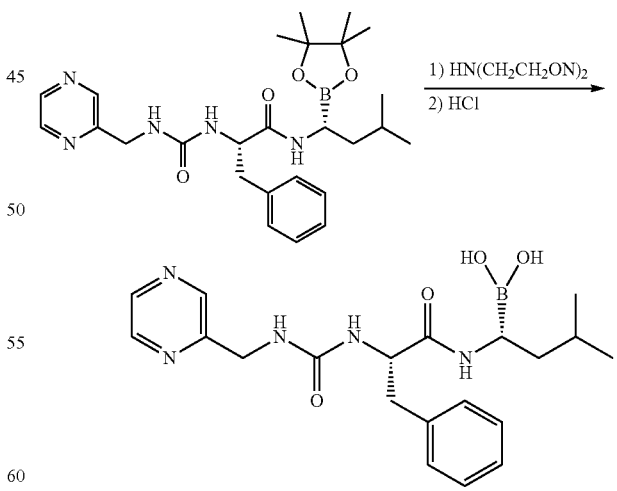

The previously obtained intermediate c (1.23 g) was dissolved in 40 mL of ethyl acetate and the solution was filtered. Diethanolamine (0.2 mL, 1.1 equiv) was added dropwise under stirring. The mixture was allowed to stir for 48 h at room temperature. The precipitate was collected by suction filtration and washed with ethyl acetate (20 mL×2). The solid was suspended in ethyl acetate (20 mL), and collected by suction filtration again. The solid was suspended in ethyl acetate (20 mL), then distilled water (20 mL) and 4 N HCl (1 mL) was added. The mixture was vigorously stirred for 6 h and the reaction was completed. The water layer was removed by liquid partition, and the organic layer was washed with distilled water (50 mL×2) and saturated brine (50 mL×2), then dried over $Na_2SO_4$. The solvent was evaporated to afford foam solid, which was recrystallized to obtain 184 mg of white solid product with a yield of 18%, mp: 154-157° C.

$^1$H NMR (400 MHz, DMSO) δ 8.53 (d, J=1.2 Hz, 1H), 8.49 (d, J=2.5 Hz, 1H), 8.43 (s, 1H), 7.35-7.08 (m, 5H), 6.71 (d, J=5.7 Hz, 1H), 6.58 (dd, J=13.4, 5.1 Hz, 1H), 4.70-4.50 (m, 1H), 4.31 (qd, J=16.6, 5.7 Hz, 2H), 2.90 (ddd, J=22.2, 13.4, 6.6 Hz, 2H), 2.66 (d, J=2.9 Hz, 1H), 1.57 (dd, J=13.3, 6.6 Hz, 1H), 1.41-1.16 (m, 2H), 0.82 (d, J=6.4 Hz, 6H). $^{13}$C NMR (101 MHz, DMSO) δ 172.46, 157.67, 155.48, 144.08, 143.50, 143.34, 137.59, 129.81, 128.47, 126.82, 52.74, 43.44, 38.86, 25.58, 23.38, 23.24, 21.49. HRMS (ESI) calcd for $C_{21}H_{29}BN_5O_3$: 410.23617 [(M−$H_2O$+$CH_2$+H)$^+$], found 410.23521.

Example 3

N-L-leucine borate-N'-(tetrahydrofuran-2-ylmethyl-carbamoyl)-L-phenylalanine-urea (hlq-U52)

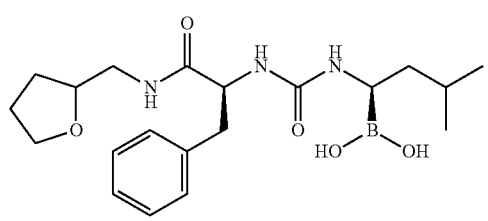 [SMILES: CC(C)C[C@H](NC(=O)N[C@@H](Cc1ccccc1)C(=O)NCC1CCCO1)B(O)O]

Using tetrahydrofuran-2-ylmethylamine as raw material instead of p-methoxy-benzylamine, the synthetic approach was analogous to that described in example 1. White solid was obtained with a yield of 21%.

$^1$H NMR (400 MHz, DMSO) δ 10.1 (s, 1H), 7.58-7.06(m, 5H), 6.73(d, J=7.0 Hz, 1H), 5.07 (s, 2H), 4.53(s, 1H), 4.41-4.37(m, 1H), 4.22-4.10(m, 1H), 3.85-3.64(m, 2H), 3.60-3.58(t, J=7.0 Hz, 1H), 3.42-3.54(d, 2H), 3.38-3.31(d, J=10.3 Hz, 7.0 Hz, 2H), 2.23-1.92(m, 4H), 1.64-1.42(m, 1H), 1.20(dd, J=14.5, 8.5 Hz, 2H), 0.85-0.68(d, J=6.8 Hz, 6H). $^{13}$C NMR (101 MHz, DMSO) δ 170.72, 159.07, 137.47, 128.56, 128.28, 126.91, 82.11, 67.64, 59.42, 59.30, 45.79, 36.71, 33.23, 31.52, 25.77, 23.67, 23.20, 21.52. HRMS (ESI) calcd for C21H33BN3O4: 402.31542 [(M−$H_2O$+$CH_2$+H)$^+$], found 402.31539.

Example 4

N-L-leucine borate-N'-(3-benzyloxy-phenylcarbamoyl)-L-phenylalanine-urea (hlq-U53)

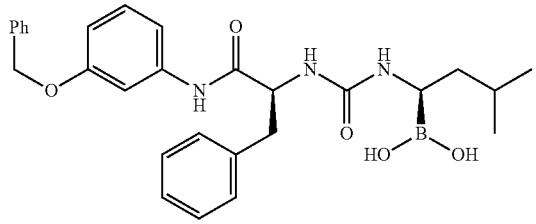 [SMILES: CC(C)C[C@H](NC(=O)N[C@@H](Cc1ccccc1)C(=O)Nc1cccc(OCc2ccccc2)c1)B(O)O]

Using 3-benzyloxy-phenylamine as raw material instead of p-methoxy-benzylamine, the synthetic approach was analogous to that described in example 1. White foam solid was obtained with a yield of 27%, mp: 113-115° C.

$^1$H NMR (400 MHz, DMSO) δ 10.12 (s, 1H), 7.58-7.06 (m, 16H), 6.73 (d, J=7.0 Hz, 1H), 5.07 (s, 2H), 4.53 (s, 1H), 3.03 (s, 1H), 2.90 (s, 1H), 1.64-1.42 (m, 1H), 1.20 (dd, J =14.5, 8.5 Hz, 2H), 0.85-0.68 (s, 6H). $^{13}$C NMR (101 MHz, DMSO) δ 170.72, 159.07, 140.31, 137.47, 130.00, 129.77, 129.55, 128.89, 128.56, 128.28, 128.09, 126.91, 112.42, 110.07, 106.68, 69.60, 56.19, 41.91, 25.77, 23.67, 23.20, 21.52. HRMS (ESI) calcd for $C_{29}H_{35}BN_3O_4$: 500.27202 [(M−$H_2O$+$CH_2$+H)$^+$], found 500.27051.

Example 5

N-L-leucine borate pinanediol ester-N'-(3-benzyloxy-phenylcarbamoyl)-L-phenylalanine-urea (hlq-U53-3)

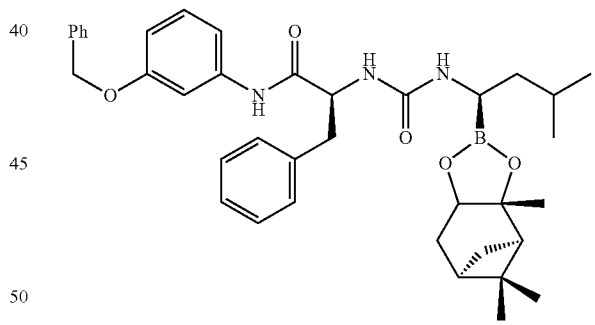

The product (0.2 mmol) of example 4 was dissolved in ethyl acetate (5 mL), to the stirred solution was added (+)-pinanediol (1.1 equiv). The reaction continued for 2 h at room temperature and was completed. Simple column chromatography with silica gel in dropper filtration was applied to obtain white foam solid with a yield of 87%, mp: 78-80° C.

$^1$H NMR (400 MHz, CDCl$_3$) δ 7.48-7.30 (m, 6H), 7.22-7.08 (m, 7H), 6.97 (d, J=6.5 Hz, 1H), 6.76-6.68 (m, 1H), 6.64 (s, 1H), 6.30 (s, 1H), 4.95 (s, 2H), 4.69 (d, J=6.0 Hz, 1H), 4.19 (d, J=7.9 Hz, 1H), 3.16 (s, 2H), 2.55 (s, 1H), 2.37-2.26 (m, 1H), 2.19-2.12 (m, 1H), 2.00 (t, =5.4 Hz, 1H), 1.88 (s, 2H), 1.59-1.45 (m, 2H), 1.35 (s, 3H), 1.29 (s, 3H), 1.27 (s, 2H), 0.86 (s, 3H), 0.81 (d, J=6.2 Hz, 3H), 0.74 (d, J=6.3 Hz, 3H). $^{13}$C NMR (101 MHz, CDCl$_3$) δ 170.39, 160.99, 159.30, 138.54, 136.85, 136.07, 129.80, 129.66, 128.55, 128.49, 127.97, 127.51, 127.04, 112.91, 111.20, 106.99, 73.85, 69.91, 69.07, 53.98, 52.30, 41.70, 40.52, 40.16, 38.14, 29.61, 29.31, 27.85, 27.39, 25.54, 24.29, 23.27, 22.16. HRMS (ESI) calcd for $C_{38}H_{49}BN_3O_5$: 638.37663 [(M+H)$^+$], found 638.37449.

Example 6

N-L-leucine borate-N'-(pyrazin-2-ylcarbamoyl)-L-phenylalanine-urea (hlq-U54)

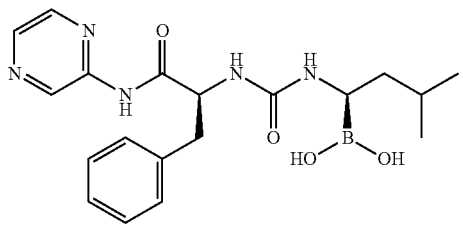 [SMILES: CC(C)C[C@H](NC(=O)N[C@@H](Cc1ccccc1)C(=O)Nc1cnccn1)B(O)O]

Using pyrazin-2-ylamine as raw material instead of p-methoxy-benzylamine, the synthetic approach was analogous to that described in example 1. White foam solid was obtained with a yield of 27%, mp: 145-148° C.

$^1$H NMR (400 MHz, DMSO) δ 10.96 (s, 1H), 9.30 (s, 1H), 8.41 (s, 1H), 8.38 (d, J=1.7 Hz, 1H), 7.42-7.17 (m, 5H), 7.17 (d, J=6.4 Hz, 1H), 4.65 (s, 1H), 3.14-2.81 (m, 2H), 2.41 (s, 1H), 1.45 (dd, J=12.7, 6.3 Hz, 1H), 1.32-1.05 (m, 2H), 0.71 (t, J=7.0 Hz, 6H). $^{13}$C NMR (101 MHz, DMSO) δ 161.07, 148.94, 143.12, 140.40, 137.51, 136.63, 129.80, 128.56, 126.95, 56.03, 41.74, 25.69, 23.56, 23.14, 21.51. HRMS (ESI) calcd for C20H27BN5O3: 396.22050 [(M–H2O+CH2+H)+], found 396.21936.

Example 7

N-L-leucine borate pinanediol ester-N'-(pyrazin-2-ylcarbamoyl)-L-phenylalanine-urea (hlq-U54-3)

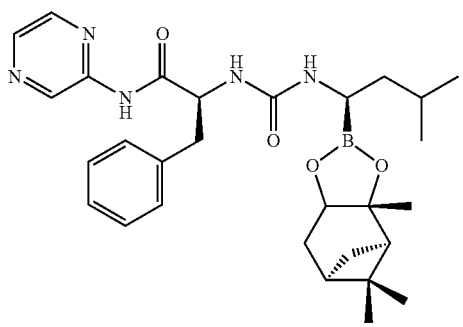

Using the product of example 6 as raw material, the synthetic approach was analogous to the esterification route described in example 5. White foam solid was obtained with a yield of 79%, mp: 93-95° C.

$^1$H NMR (400 MHz, CDCl$_3$) δ 9.52 (s, 1H), 9.49 (s, 1H), 8.31 (d, J=2.5 Hz, 1H), 8.23-8.05 (m, 1H), 7.24-7.04 (m, 5H), 6.35 (s, 1H), 6.08 (s, 1H), 4.77 (d, J=6.8 Hz, 1H), 4.18 (d, J=8.0 Hz, 1H), 3.15 (ddd, J=35.8, 13.9, 7.0 Hz, 2H), 2.81 (s, 1H), 2.34-2.17 (m, 1H), 2.08 (dd, J=10.3, 5.9 Hz, 1H), 1.93 (t, J=5.3 Hz, 1H), 1.84-1.73 (m, 2H), 1.58 (dd, J=13.2, 6.5 Hz, 1H), 1.35 (qd, J=14.0, 7.8 Hz, 3H), 1.25 (s, 3H), 1.22 (s, 3H), 0.82 (t, J=6.8 Hz, 6H), 0.79 (s, 3H). $^{13}$C NMR (101 MHz, CDCl$_3$) δ 171.22, 160.20, 147.82, 142.06, 140.30, 137.30, 135.98, 129.21, 128.65, 127.12, 69.16, 56.83, 51.81, 41.15, 39.80, 38.10, 37.98, 36.12, 28.80, 27.20, 26.49, 25.52, 24.10, 23.08, 22.18. HRMS (ESI) calcd for $C_{29}H_{41}BN_5O_4$: 534.32512 [(M+H)$^+$], found 534.32362.

Example 8

N-L-leucine borate-N'-(p-methoxy-phenylcarbamoyl)-L-phenylalanine-urea (hlq-U55)

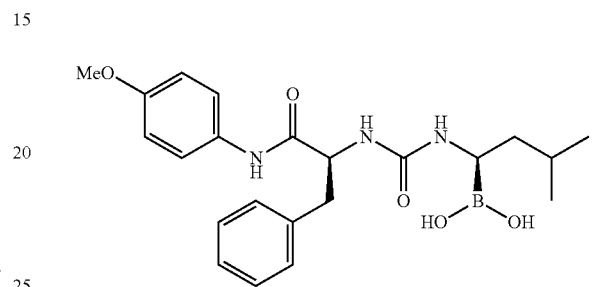

Using p-methoxy-phenylamine as raw material instead of p-methoxy-benzylamine, the synthetic approach was analogous to that described in example 1. White foam solid was obtained with a yield of 25%, mp: 146-148° C.

$^1$H NMR (400 MHz, DMSO) δ 9.91 (s, 1H), 7.45 (d, J=8.9 Hz, 2H), 7.20 (m, 5H), 7.18 (d, J=6.0 Hz, 1H), 6.88 (d, J=9.0 Hz, 2H), 4.50 (d, J=5.4 Hz, 1H), 3.71 (s, 3H), 3.13-2.79 (m, 2H), 1.53 (td, J=12.9, 6.3 Hz, 1H), 1.34-1.09 (m, 2H), 0.91-0.70 (t, J=4.0 Hz, 6H). $^{13}$C NMR (101 MHz, DMSO) δ 172.46, 169.90, 155.90, 137.66, 132.15, 129.78, 128.54, 126.86, 121.50, 114.30, 55.61, 41.95, 38.85, 25.78, 23.69, 23.20. HRMS (ESI) calcd for $C_{23}H_{31}BN_3O_4$: 424.24062 [(M–H$_2$O+CH$_2$+H)$^+$], found 424.23945.

Example 9

N-L-leucine borate pinanediol ester-N'-(p-methoxy-phenylcarbamoyl)-L-phenylalanine-urea (hlq-U55-3)

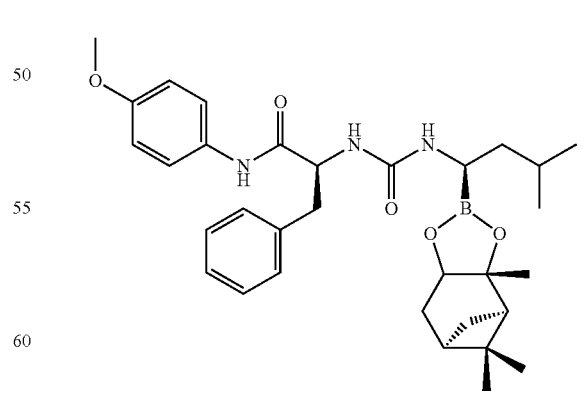

Using the product of example 8 as raw material, the synthetic approach was analogous to the esterification route described in example 5. White foam solid was obtained with a yield of 86%, mp: 78-80° C.

$^1$H NMR (400 MHz, DMSO) δ 9.96 (d, J=39.6 Hz, 1H), 7.43 (d, J=9.0 Hz, 2H), 7.32-7.21 (m, 6H), 7.00 (s, 2H), 6.88 (d, =9.1 Hz, 2H), 4.48 (d, =5.1 Hz, 1H), 3.95 (d, =7.7 Hz, 1H), 3.72 (s, 3H), 3.01 (ddd, =21.3, 13.7, 6.6 Hz, 2H), 2.39 (t, =7.3 Hz, 1H), 2.15 (dd, =11.7, 9.8 Hz, 1H), 2.00-1.91 (m, 1H), 1.77 (dd, =11.4, 5.5 Hz, 2H), 1.68-1.54 (m, 2H), 1.42 (d, =9.7 Hz, 1H), 1.20 (s, 3H), 1.18 (s, 3H), 0.84 (t, =7.2 Hz, 6H), 0.80 (s, 3H). $^{13}$C NMR (101 MHz, DMSO) δ 169.42, 161.81, 155.93, 137.36, 132.07, 129.79, 128.62, 127.02, 121.56, 114.27, 81.77, 75.49, 56.35, 55.60, 52.75, 42.25, 38.07, 37.38, 29.80, 27.77, 26.58, 25.78, 24.52, 23.77, 22.51. HRMS (ESI) calcd for $C_{32}H_{45}BN_3O_5$: 562.34523 [(M+H)$^+$], found 562.34326.

Example 10

N-L-leucine borate-N'-(pyrazin-2-ylcarbamoyl)-D-phenylalanine-urea (hlq-U56)

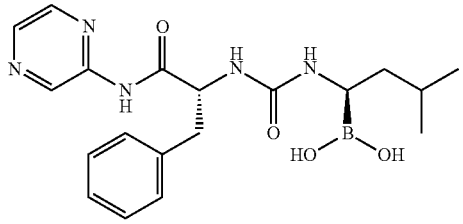 [SMILES: CC(C)C[C@H](NC(=O)N[C@H](Cc1ccccc1)C(=O)Nc1cnccn1)B(O)O]

Using pyrazin-2-ylamine instead of p-methoxy-benzylamine, and Boc-D-phenylalanine instead of Boc-L-phenylalanine, the synthetic approach was analogous to that described in example 1. Yellowish white foam solid was obtained with a yield of 24%, mp: 138-141° C.

$^1$H NMR (400 MHz, DMSO) δ 11.12-10.93 (m, 1H), 9.45-9.22 (m, 1H), 8.40 (s, 1H), 8.37 (s, 1H), 7.28 (d, J=18.4 Hz, 5H), 7.21-7.15 (m, 1H), 6.52 (s, 1H), 4.68 (s, 1H), 2.92 (dd, J=50.3, 43.2 Hz, 2H), 2.44 (s, 1H), 1.45 (dd, J=12.6, 6.3 Hz, 1H), 1.13 (ddd, J=20.3, 12.1, 6.9 Hz, 3H), 0.77-0.61 (dd, J=6.9, 4.2 Hz, 6H). $^{13}$C NMR (101 MHz, DMSO) δ 172.45, 160.69, 148.96, 143.11, 140.39, 137.52, 136.66, 129.83, 128.53, 126.92, 55.88, 41.92, 25.66, 23.61, 23.57, 23.06, 21.49. HRMS (ESI) calcd for $C_{20}H_{27}BN_5O_3$: 396.22050 [(M−H$_2$O+CH$_2$+H)$^+$], found 396.21952.

Example 11

N-L-leucine borate-N'-(pyrazin-2-ylcarbamoyl)-L-leucyl-L-leucine-urea (hlq-U61)

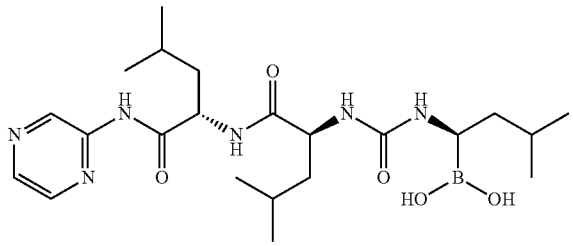 [SMILES: CC(C)C[C@H](NC(=O)N[C@@H](CC(C)C)C(=O)N[C@@H](CC(C)C)C(=O)Nc1cnccn1)B(O)O]

Using N-pyrazinyl-L-leucinamide instead of p-methoxy-benzylamine, and Boc-L-leucine instead of Boc-L-phenyl-alanine, the synthetic approach was analogous to that described in example 1. White foam solid was obtained with a yield of 21%, mp: 157-162° C.

$^1$H NMR (400 MHz, DMSO) δ 10.95 (s, 1H), 9.29 (s, 1H), 8.40 (s, 1H), 8.36 (d, J=2.3 Hz, 1H), 8.13 (d, J=7.2 Hz, 1H), 6.67 (s, 1H), 4.63 (s, 1H), 4.20 (dd, J=15.8, 12.3 Hz, 1H), 1.77-1.10 (m, 9H), 0.99-0.73 (m, 18H). $^{13}$C NMR (101 MHz, DMSO) δ 173.57, 172.60, 149.09, 143.10, 140.31, 140.27, 136.80, 52.37, 52.02, 42.10, 41.07, 25.69, 24.66, 24.49, 23.71, 23.58, 23.30, 22.36, 21.89, 21.83. HRMS (ESI) calcd for $C_{23}H_{40}BN_6O_4$: 475.32027 [(M−H$_2$O+CH$_2$+H)$^+$], found 475.31908.

Example 12

N-L-leucine borate-N'-(pyrazin-2-ylcarbamoyl)-L-leucyl-L-phenylalanine-urea (hlq-U62)

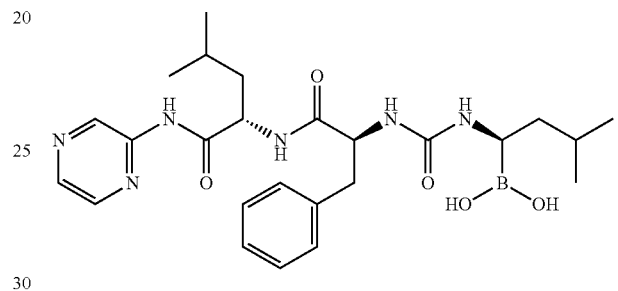

Using N-pyrazinyl-L-leucinamide as raw material instead of p-methoxy-benzylamine, the synthetic approach was analogous to that described in example 1. White foam solid was obtained with a yield of 38%, mp: 154-157° C.

$^1$H NMR (400 MHz, DMSO) δ 10.93 (s, 1H), 9.33 (s, 1H), 8.42 (d, J=1.4 Hz, 1H), 8.39 (d, J=2.4 Hz, 1H), 8.24 (dd, J=18.5, 7.8 Hz, 1H), 7.31-6.97 (m, 5H), 4.66 (dd, J=13.8, 7.5 Hz, 1H), 4.50-4.26 (m, 1H), 3.14-2.69 (m, 2H), 1.75-1.47 (m, 4H), 1.39-1.11 (m, 2H), 0.89 (dd, J=11.9, 6.4 Hz, 6H), 0.80 (t, J=5.6 Hz, 6H). $^{13}$C NMR (101 MHz, DMSO) δ 172.45, 172.43, 149.08, 143.11, 140.35, 137.68, 136.86, 129.83, 129.51, 128.34, 126.65, 52.03, 42.04, 41.12, 25.71, 24.66, 23.73, 23.52, 23.24, 22.02, 21.49. HRMS (ESI) calcd for $C_{26}H_{38}BN6O_4$: 509.30467 [(M−H$_2$O+CH$_2$+H)$^+$], found 509.30313.

Example 13

N-L-leucine borate pinacol ester-N'-(pyrazin-2-ylcarbamoyl)-L-leucyl-L-phenylalanine-urea (hlq-U62-1)

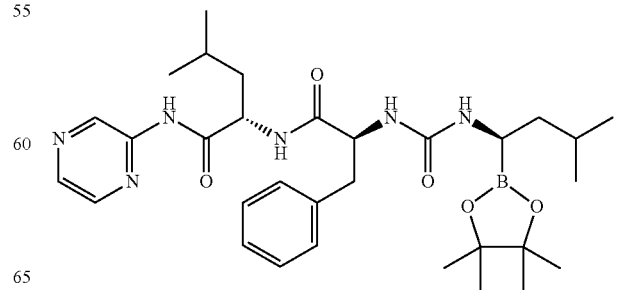

Using N-pyrazinyl-L-leucinamide as raw material instead of p-methoxy-benzylamine, the synthetic approach was analogous to that described in example 1 but the hydrolytic step of intermediate c was omitted. White solid was obtained with a yield of 58%, mp: 196-198° C.

$^1$H NMR (400 MHz, DMSO) δ 11.00 (s, 1H), 9.32 (s, 1H), 8.45-8.41 (m, 1H), 8.39 (d, J=2.6 Hz, 1H), 7.13 (m, 7H), 4.66 (s, 1H), 4.43 (dd, J=12.9, 7.6 Hz, 1H), 3.04 (d, J=9.0 Hz, 1H), 2.88-2.80 (m, 1H), 2.30 (d, J=28.5 Hz, 1H), 1.68 (m, 1H), 1.56 (m, 3H), 1.16-1.07 (m, 2H), 1.04 (s, 12H), 0.91 (dd, J=11.5, 6.6 Hz, 6H), 0.82 (dd, J=12.0, 6.5 Hz, 6H). $^{13}$C NMR (101 MHz, DMSO) δ 172.60, 170.74, 162.08, 149.10, 143.12, 140.34, 136.85, 129.83, 128.44, 128.26, 126.83, 79.02, 52.07, 42.18, 40.93, 36.27, 25.79, 24.73, 24.19, 23.53, 22.10, 22.03.

Example 14

N-L-phenylalanyl-L-leucine borate-N'-benzylamine-urea (hlq-U05)

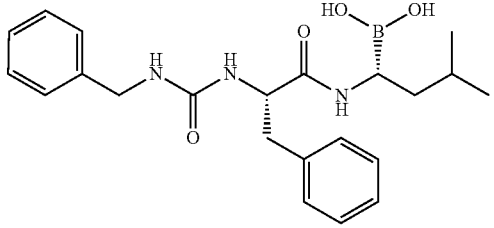 [SMILES: CC(C)C[C@H](NC(=O)[C@H](Cc1ccccc1)NC(=O)NCc1ccccc1)B(O)O]

Using benzylamine as raw material instead of pyrazin-2-ylmethylamine, the synthetic approach was analogous to that described in example 2. White foam solid was obtained with a yield of 15%, mp: 133-136° C.

$^1$H NMR (400 MHz, DMSO) δ 7.41-7.14 (m, 9H), 7.17-7.02 (m, 2H), 6.51 (s, 1H), 6.35 (dd, J=8.4, 4.6 Hz, 1H), 4.70-4.52 (m, 1H), 4.16 (ddd, J=20.4, 15.4, 5.8 Hz, 2H), 3.00 (dd, J=8.9, 4.1 Hz, 1H), 2.91-2.77 (m, 1H), 2.68 (s, 1H), 1.60 (dd, J=13.0, 6.6 Hz, 1H), 1.32 (ddd, J=26.5, 15.3, 6.7 Hz, 2H), 0.84 (d, J=6.2 Hz, 6H). $^{13}$C NMR (101 MHz, DMSO) δ 174.88, 157.71, 140.93, 137.53, 129.86, 128.61, 128.50, 127.29, 126.96, 126.80, 43.25, 38.96, 25.57, 23.48, 23.20, 23.02, 21.51. HRMS (ESI) calcd for $C_{23}H_{31}BN_3O_3$: 408.24571 [(M–H$_2$O+CH$_2$+H)$^+$], found 408.24429.

Example 15

N-L-phenylalanyl-L-leucine borate-N'-(p-methoxy-benzylamine)-urea (hlq-U07)

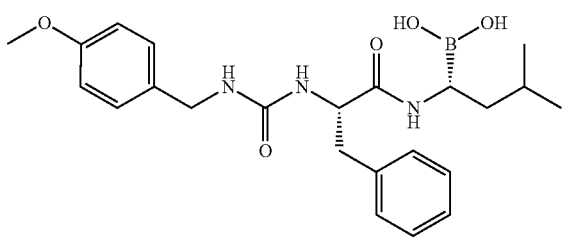 [SMILES: COc1ccc(CNC(=O)N[C@@H](Cc2ccccc2)C(=O)N[C@@H](CC(C)C)B(O)O)cc1]

Using p-methoxy-benzylamine as raw material instead of pyrazin-2-ylmethylamine, the synthetic approach was analogous to that described in example 2. White foam solid was obtained with a yield of 31%, mp: 126-128° C.

$^1$H NMR (400 MHz, DMSO) δ 7.31-7.19 (m, 5H), 7.06 (d, J=8.5 Hz, 2H), 6.83 (d, J=8.6 Hz, 2H), 6.42 (s, 1H), 6.30 (d, J=8.5 Hz, 1H), 4.63 (dd, J=13.7, 7.9 Hz, 1H), 4.20-3.98 (m, 2H), 3.71 (s, 3H), 3.04-2.76 (m, 2H), 2.67 (d, J=2.7 Hz, 1H), 1.59 (dd, J=13.1, 6.5 Hz, 1H), 1.40-1.20 (m, 2H), 0.84 (d, J=4.0 Hz, 6H). $^{13}$C NMR (101 MHz, DMSO) δ 174.96, 158.53, 157.65, 137.61, 132.78, 129.86, 128.64, 128.50, 126.80, 114.04, 55.46, 42.76, 38.97, 25.59, 23.40, 23.27, 21.49. HRMS (ESI) calcd for $C_{24}H_{33}BN_3O_4$: 438.25629 [(M–H$_2$O+CH$_2$+H)$^+$], found 438.25508.

Example 16

N-L-phenylalanyl-L-leucine borate-N'-(3-benzyloxy-phenylamine)-urea (hlq-U21)

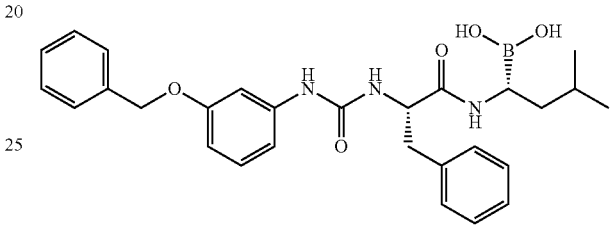

Using 3-benzyloxy-phenylamine as raw material instead of pyrazin-2-ylmethylamine, the synthetic approach was analogous to that described in example 2. White foam solid was obtained with a yield of 26%, mp: 112-115° C.

$^1$H NMR (400 MHz, DMSO) δ 8.84 (d, J=17.7 Hz, 1H), 8.67 (d, J=9.8 Hz, 1H), 7.52-7.16 (m, 11H), 7.10 (dt, =13.7, 6.8 Hz, 1H), 6.86 (d, J=6.6 Hz, 1H), 6.57 (d, J=8.1 Hz, 1H), 6.45 (dd, J=19.5, 8.9 Hz, 1H), 5.04 (s, 2H), 4.77-4.57 (m, 1H), 3.12-2.87 (m, 2H), 2.72 (s, 1H), 1.59 (dt, =13.1, 9.2 Hz, 1H), 1.45-1.20 (m, 2H), 0.84 (d, J=5.4 Hz, 6H). $^{13}$C NMR (101 MHz, DMSO) δ 174.37, 159.25, 154.75, 141.85, 137.64, 137.26, 129.93, 129.87, 128.84, 128.57, 128.18, 128.00, 126.91, 110.77, 108.01, 104.91, 69.52, 52.18 (m), 38.97, 33.84, 25.54, 23.60, 22.94, 21.49. HRMS (ESI) calcd for $C_{29}H_{35}BN_3O_4$: 500.27202 [(M–H$_2$O+CH$_2$+H)$^+$], found 500.27025.

Example 17

N-L-phenylalanyl-L-leucine borate-N'-(pyrazin-2-ylamine)-urea (hlq-U22)

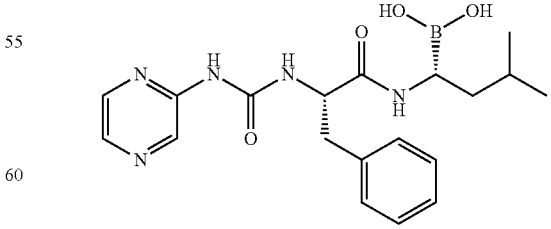

Using pyrazin-2-ylamine as raw material instead of pyrazin-2-ylmethylamine, the synthetic approach was analogous to that described in example 2. White foam solid was obtained with a yield of 17%, mp: 135-138° C.

¹H NMR (400 MHz, DMSO) δ 9.54 (s, 1H), 8.86 (d, J=14.4 Hz, 1H), 8.76 (d, J=6.0 Hz, 1H), 8.17 (dd, J=9.2, 5.6 Hz, 2H), 7.94 (d, J=6.6 Hz, 1H), 7.22 (dt, =27.6, 4.1 Hz, 5H), 4.82-4.62 (m, 1H), 3.14-2.90 (m, 2H), 2.64 (br, 1H), 1.56 (dt, J=13.1, 6.6 Hz, 1H), 1.39-1.12 (m, 2H), 0.78 (dd, J=6.1, 2.6 Hz, 6H). ¹³C NMR (101 MHz, DMSO) δ 173.89, 154.06, 150.00, 141.47, 137.59, 136.92, 135.47, 130.00, 128.59, 127.07, 52.47, 38.61, 25.48, 23.49, 23.01, 22.93. HRMS (ESI) calcd for $C_{20}H_{27}BN_5O_3$: 396.22050 [(M−$H_2O+CH_2+H$)⁺], found 396.21998.

Example 18

N-L-phenylalanyl-L-leucine borate-N'-(2,5-dimethoxy-benzylamine)-urea (hlq-U23)

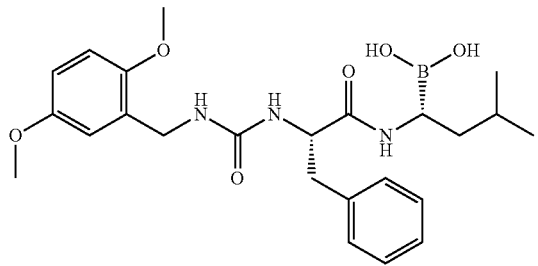 [SMILES: COc1ccc(OC)c(CNC(=O)N[C@@H](Cc2ccccc2)C(=O)N[C@@H](CC(C)C)B(O)O)c1]

Using 2,5-dimethoxy-benzylamine as raw material instead of pyrazin-2-ylmethylamine, the synthetic approach was analogous to that described in example 2. White solid was obtained with a yield of 28%, mp: 156-159° C.

¹H NMR (400 MHz, DMSO) δ 7.23-7.10 (m, 5H), 6.83 (d, J=8.8 Hz, 1H), 6.76-6.68 (m, 2H), 4.30 (dt, J=13.9, 6.2 Hz, 0H), 4.08 (d, J=5.0 Hz, 2H), 3.97 (m, 2H), 3.69 (s, 3H), 3.63 (s, 3H), 3.10-2.83 (m, 2H), 2.81-2.65 (m, 1H), 1.50-1.14 (m, 1H), 0.90-0.58 (dd, 6H). ¹³C NMR (101 MHz, DMSO) δ 171.93, 158.22, 153.46, 151.14, 137.86, 129.56, 129.27, 128.53, 126.73, 114.62, 112.29, 111.83, 56.13, 55.73, 38.45, 25.18, 24.96, 23.55, 23.52, 22.26, 22.02. HRMS (ESI) calcd for $C_{25}H_{35}BN_3O_5$: 468.26687 [(M−$H_2O+CH_2+H$)⁺], found 468.26590.

Example 19

N-L-phenylalanyl-L-leucine borate pinanediol ester-N'-(2,5-dimethoxy-benzylamine)-urea (hlq-U23-3)

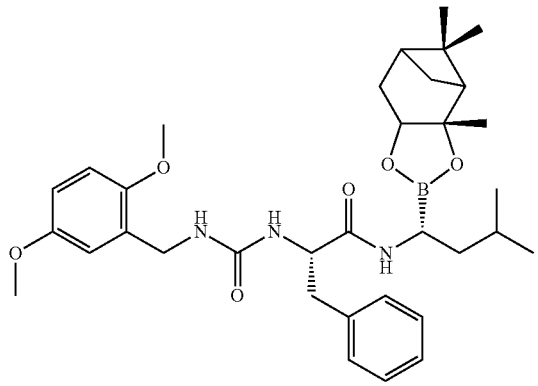

Using the product of example 18 as raw material, the synthetic approach was analogous to the esterification route described in example 5. White solid was obtained with a yield of 89%, mp: 88-90° C.

¹H NMR (400 MHz, CDCl₃) δ 7.32-7.18 (m, 5H), 6.99-6.83 (m, 1H), 6.80-6.68 (m, 2H), 6.14 (s, 1H), 4.38 (dd, J=15.2, 6.0 Hz, 1H), 4.31-4.23 (m, 1H), 3.76 (s, 3H), 3.73 (s, 3H), 3.17 (d, J=6.6 Hz, 1H), 3.10-2.63 (m, 2H), 2.03 (d, J=17.3 Hz, 2H), 1.98-1.73 (m, 2H), 1.68-1.42 (m, 2H), 1.28 (s, 3H), 1.23 (s, 3H), 1.14 (d, J=9.7 Hz, 3H), 0.90-0.79 (m, 6H), 0.76 (s, 3H). ¹³C NMR (101 MHz, CDCl₃) δ 158.46, 153.67, 151.35, 137.20, 129.48, 129.24, 128.48, 126.59, 115.44, 115.10, 112.34, 111.10, 55.69, 51.89, 51.61, 40.35, 39.72, 37.99, 35.70, 28.90, 28.56, 27.23, 27.14, 26.36, 26.28, 25.76, 25.34, 23.99, 23.04, 23.00, 21.94. HRMS (ESI) calcd for $C_{34}H_{49}BN_3O_6$: 606.37148 [(M+H)⁺], found 606.36972.

Example 20

N-L-phenylalanyl-L-leucine borate-N'-(2,3-dichloro-benzylamine)-urea (hlq-U24)

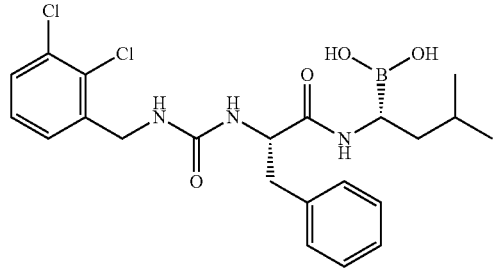 [SMILES: CC(C)C[C@H](NC(=O)[C@H](Cc1ccccc1)NC(=O)NCc1cccc(Cl)c1Cl)B(O)O]

Using 2,3-dichloro-benzylamine as raw material instead of pyrazin-2-ylmethylamine, the synthetic approach was analogous to that described in example 2. White foam solid was obtained with a yield of 32%, mp: 119-122° C.

¹H NMR (400 MHz, DMSO) δ 7.22 (m, 8H), 7.12 (d, J=4.3 Hz, 1H), 6.49 (s, 1H), 6.33 (d, S=8.7 Hz, 1H), 4.58 (d, J=5.9 Hz, 1H), 4.12 (dt, =15.3, 10.3 Hz, 2H), 2.98 (d, J=12.4 Hz, 1H), 2.90-2.74 (m, 1H), 2.64 (s, 1H), 1.70-1.45 (m, 1H), 1.28 (m, 2H), 0.83 (d, J=5.5 Hz, 6H). ¹³C NMR (101 MHz, DMSO) δ 175.00, 157.69, 140.98, 137.54, 129.89, 129.82, 128.59, 128.50, 128.40 (m, 18H), 127.29, 126.95, 126.79, 43.24, 38.99, 25.54, 23.60, 23.01, 21.50. HRMS (ESI) calcd for $C_{23}H_{29}BCl_2N_3O_3$: 462.25222 [(M−$H_2O+CH_2+H$)⁺], found 462.25277.

Example 21

N-glycyl-L-leucine borate-N'-(3-benzyloxy-phenylamine)-urea (hlq-U25)

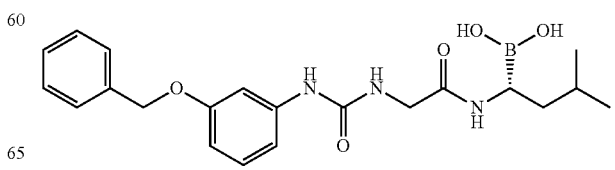

Using 3-benzyloxy-phenylamine as raw material instead of pyrazin-2-ylmethylamine, and glycine methyl ester instead of L-phenylalanine methyl ester, the synthetic approach was analogous to that described in example 2. White foam solid was obtained with a yield of 36%, mp: 109-113° C.

$^1$H NMR (400 MHz, DMSO) δ 8.82 (s, 1H), 8.77 (s, 1H), 7.37 (m, 5H), 7.26 (s, 1H), 7.13 (t, J=8.1 Hz, 1H), 6.92 (d, J=7.8 Hz, 1H), 6.64-6.54 (m, 1H), 6.47 (t, J=5.2 Hz, 1H), 5.05 (s, 2H), 3.92 (d, J=4.6 Hz, 2H), 2.64 (s, 1H), 1.62 (dt, J=13.2, 6.6 Hz, 1H), 1.44-1.20 (m, 2H), 0.83 (d, J=4.9 Hz, 6H). $^{13}$C NMR (101 MHz, DMSO) δ 173.08, 159.24, 155.44, 142.00, 137.65, 129.87, 128.84, 128.18, 128.00, 110.86, 108.02, 104.97, 69.51, 43.5 (m), 40.85, 25.62, 23.39, 23.25, 21.49. HRMS (ESI) calcd for $C_{22}H_{29}BN_3O_4$: 410.22495 [(M−H$_2$O+CH$_2$+H)$^+$], found 410.22377.

Example 22

N-glycyl-L-leucine borate-N'-(2,5-dichloro-phenylamine)-urea (hlq-U26)

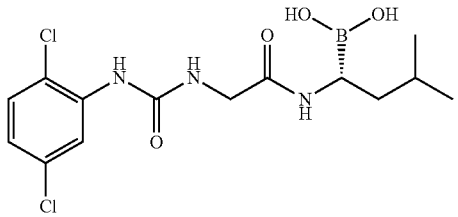 [SMILES: CC(C)C[C@H](NC(=O)CNC(=O)Nc1cc(Cl)ccc1Cl)B(O)O]

Using 2,5-dichloro-phenylamine as raw material instead of pyrazin-2-ylmethylamine, and glycine methyl ester instead of L-phenylalanine methyl ester, the synthetic approach was analogous to that described in example 2. White foam solid was obtained with a yield of 17%, mp: 125-129° C.

$^1$H NMR (400 MHz, DMSO) δ 8.79 (s, 1H), 8.47 (d, J=10.7 Hz, 1H), 8.30 (d, J=2.2 Hz, 1H), 7.57 (dd, J=10.3, 5.3 Hz, 1H), 7.41 (dd, J=8.5, 4.3 Hz, 1H), 7.00 (dd, J=8.5, 2.2 Hz, 1H), 3.95 (d, J=4.8 Hz, 2H), 3.37 (m, 1H), 1.61 (m, 1H), 1.38-1.17 (m, 2H), 0.83 (dd, J=13.9, 3.7 Hz, 6H). $^{13}$C NMR (101 MHz, DMSO) δ 172.63, 168.84, 155.05, 138.26, 132.30, 130.79, 122.41, 119.91, 43.04, 25.60, 23.34, 23.17, 22.91. HRMS (ESI) calcd for $C_{15}H_{21}BCl_2N_3O_3$: 372.10502 [(M−H$_2$O+CH$_2$+H)$^+$], found 372.10413.

Example 23

N-L-phenylalanyl-L-phenylalanyl-L-leucine borate-N'-(3-benzyloxy-phenylamine)-urea (hlq-U31)

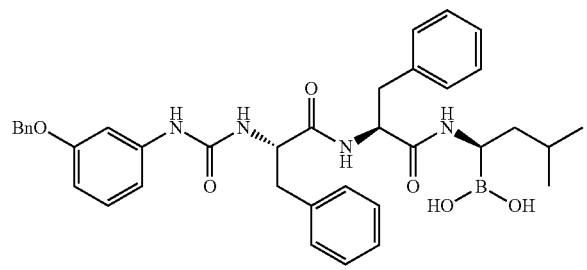 [SMILES: CC(C)C[C@H](NC(=O)[C@H](Cc1ccccc1)NC(=O)[C@H](Cc1ccccc1)NC(=O)Nc1cccc(OCc2ccccc2)c1)B(O)O]

Using 3-benzyloxy-phenylamine as raw material instead of pyrazin-2-ylmethylamine, and L-phenylalanyl-L-phenylalanine methyl ester instead of L-phenylalanine methyl ester, the synthetic approach was analogous to that described in example 2. White foam solid was obtained with a yield of 18%, mp: 130-133° C.

$^1$H NMR (400 MHz, DMSO) δ 8.72 (d, J=5.6 Hz, 1H), 8.65 (d, J=16.6 Hz, 1H), 8.55 (s, 1H), 7.48-7.06 (m, 16H), 6.87 (d, J=8.3 Hz, 1H), 6.80 (d, J=4.0 Hz, 1H), 6.64-6.50 (m, 1H), 6.24 (d, J=5.9 Hz, 1H), 5.04 (s, 2H), 4.68 (dd, J=14.3, 6.5 Hz, 1H), 4.51 (dd, J=16.6, 6.0 Hz, 1H), 3.00 (dd, J=35.2, 22.1 Hz, 2H), 2.88-2.64 (m, 2H), 1.59 (s, 1H), 1.31 (dd, J=23.7, 18.0 Hz, 2H), 0.79 (dd, J=21.1, 5.3 Hz, 6H). $^{13}$C NMR (101 MHz, DMSO) δ 172.42, 171.75, 159.25, 154.96, 141.92, 137.64, 129.88, 129.84, 129.74, 128.84, 128.83, 128.51, 128.36, 128.18, 127.99, 126.69, 126.60, 110.69, 107.92, 104.87, 69.54, 54.30, 37.81, 25.51, 23.67, 23.41, 22.98, 22.80, 21.49. HRMS (ESI) calcd for $C_{38}H_{44}BN_4O_5$: 647.34057 [(M−H$_2$O+CH$_2$+H)], found 647.33814.

Example 24

N-L-phenylalanyl-L-leucine borate-N'-(pyrazin-2-ylcarbamoyl)-L-phenylalanine-urea(hlq-U32)

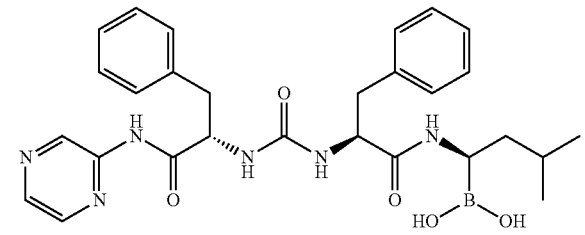 [SMILES: CC(C)C[C@H](NC(=O)[C@H](Cc1ccccc1)NC(=O)N[C@@H](Cc1ccccc1)C(=O)Nc1cnccn1)B(O)O]

Using N-pyrazinyl-L-phenylalaninamide as raw material instead of pyrazin-2-ylmethylamine, the synthetic approach was analogous to that described in example 2. White foam solid was obtained with a yield of 14%, mp: 170-174° C.

$^1$H NMR (400 MHz, DMSO) δ 10.89 (s, 1H), 9.31 (s, 1H), 8.40 (s, 1H), 8.37 (s, 1H), 7.47 (s, 1H), 7.31-7.09 (m, 10H), 6.54 (d, J=7.7 Hz, 1H), 6.40 (d, J=7.6 Hz, 1H), 4.67 (d, J=4.3 Hz, 1H), 4.29 (d, J=5.5 Hz, 1H), 3.10-2.94 (m, 2H), 2.79 (ddd, J=21.0, 13.6, 8.0 Hz, 2H), 1.50 (dd, J=12.7, 6.4 Hz, 1H), 1.41-1.10 (m, 2H), 0.78 (dd, J=27.1, 6.5 Hz, 6H). $^{13}$C NMR (101 MHz, DMSO) δ 172.61, 171.53, 157.53, 149.07, 143.11, 140.24, 138.27, 137.80, 136.69, 129.80, 129.76, 128.55, 128.37, 126.82, 126.47, 55.49, 54.67, 38.77, 38.35, 25.18, 23.71, 23.66, 22.46. HRMS (ESI) calcd for $C_{29}H_{36}BN_6O_4$: 543.28907 [(M−H$_2$O+CH$_2$+H)$^+$], found 543.28785.

Example 25

N-L-phenylalanyl-L-leucine borate-N'-phenylethyl-amine-urea (hlq-U71)

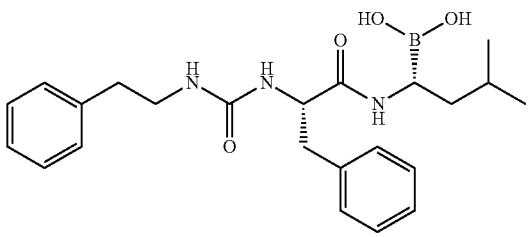 [SMILES: CC(C)C[C@H](NC(=O)[C@H](Cc1ccccc1)NC(=O)NCCc1ccccc1)B(O)O]

Using phenylethylamine as raw material instead of pyrazin-2-ylmethylamine, the synthetic approach was analogous to that described in example 2. White foam solid was obtained with a yield of 18%, mp: 134-137° C.

$^1$H NMR (400 MHz, DMSO) δ 8.63 (d, J=17.7 Hz, 1H), 7.33-7.06 (m, 10H), 6.37-6.24 (m, 1H), 6.05 (s, 1H), 4.55 (dd, J=16.1, 8.1 Hz, 1H), 3.26-3.09 (m, 2H), 2.87 (ddd, J=21.9, 13.6, 7.1 Hz, 2H), 2.61 (m, 3H), 1.75-1.44 (m, 1H), 1.45-1.13 (m, 2H), 0.82 (d, J=5.9 Hz, 6H). $^{13}$C NMR (101 MHz, DMSO) δ 174.98, 157.58, 140.06, 137.66, 129.83, 129.08, 128.73, 128.49, 126.79, 126.42, 52.62, 41.39, 38.95, 36.47, 25.53, 23.40, 23.26. HRMS (ESI) calcd for $C_{24}H_{33}BN_3O_3$: 422.26137 [(M−H$_2$O+CH$_2$+H)$^+$], found 422.26053.

Example 26

N-L-phenylalanyl-L-leucine borate-N'—(R)-2-methyl-benzylamine-urea (hlq-U72)

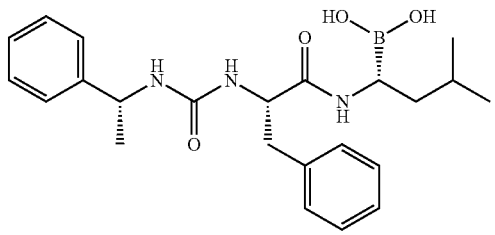 [SMILES: CC(C)C[C@H](NC(=O)[C@H](Cc1ccccc1)NC(=O)N[C@H](C)c1ccccc1)B(O)O]

Using (R)-2-methyl-benzylamine as raw material instead of pyrazin-2-ylmethylamine, the synthetic approach was analogous to that described in example 2. White foam solid was obtained with a yield of 23%, mp: 151-154° C.

$^1$H NMR (400 MHz, DMSO) δ 8.61 (s, 1H), 7.38-7.07 (m, 10H), 6.53 (d, J=7.9 Hz, 1H), 6.12 (d, J=8.5 Hz, 1H), 4.69 (p, J=6.8 Hz, 1H), 4.52 (dd, J=14.4, 7.5 Hz, 1H), 2.89 (ddd, J=21.2, 13.6, 6.8 Hz, 2H), 2.63 (s, 1H), 1.53 (dt, J=13.1, 6.5 Hz, 1H), 1.34-1.15 (m, 2H), 1.27 (d, J=4.8 Hz, 3H), 0.79 (t, J=6.2 Hz, 6H). $^{13}$C NMR (101 MHz, DMSO) δ 174.69, 156.86, 145.73, 137.49, 129.91, 128.60, 128.48, 126.87, 126.78, 126.22, 52.49, 49.07, 39.09, 25.46, 23.74, 23.66, 22.86. HRMS (ESI) calcd for $C_{24}H_{33}BN_3O_3$: 422.26137 [(M−H$_2$O+CH$_2$+H)$^+$], found 422.26043.

Example 27

N-L-phenylalanyl-L-leucine borate-N'—(S)-2-methyl-benzylamine-urea (hlq-U73)

Using (S)-2-methyl-benzylamine as raw material instead of pyrazin-2-ylmethylamine, the synthetic approach was analogous to that described in example 2. White foam solid was obtained with a yield of 32%, mp: 164-167° C.

$^1$H NMR (400 MHz, DMSO) δ 8.58 (s, 1H), 7.31-7.17 (m, 10H), 6.51 (d, J=7.8 Hz, 1H), 6.15 (d, J=8.7 Hz, 1H), 4.72-4.62 (m, 1H), 4.53 (dd, J=14.3, 8.0 Hz, 1H), 3.01-2.74 (m, 2H), 2.62 (d, J=3.4 Hz, 1H), 1.54 (dt, J=13.2, 6.6 Hz, 1H), 1.30-1.17 (m, 2H), 1.25 (d, J=5.3 Hz, 3H), 0.79 (d, J=6.6 Hz, 6H). $^{13}$C NMR (101 MHz, DMSO) δ 174.77, 156.92, 145.62, 137.51, 129.86, 128.64, 128.49, 126.90, 126.82, 126.25, 52.64, 49.10, 39.07, 25.54, 23.76, 23.37, 23.24. HRMS (ESI) calcd for $C_{24}H_{33}BN_3O_3$: 422.26137 [(M−H$_2$O+CH$_2$+H)$^+$], found 422.26051.

Example 28

N-L-phenylalanyl-L-leucine borate-N'-1,2,3,4-tetra-hydroisoquinoline-urea (hlq-U74)

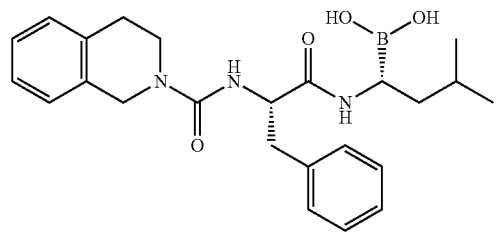 [SMILES: CC(C)C[C@H](NC(=O)[C@H](Cc1ccccc1)NC(=O)N1CCc2ccccc2C1)B(O)O]

Using 1,2,3,4-tetrahydroisoquinoline as raw material instead of pyrazin-2-ylmethylamine, the synthetic approach was analogous to that described in example 2. White foam solid was obtained with a yield of 28%, mp: 158-160° C.

$^1$H NMR (400 MHz, DMSO) δ 8.64 (s, 1H), 7.39-6.93 (m, 9H), 6.76 (d, J=8.2 Hz, 1H), 4.57 (dd, J=14.2, 8.7 Hz, 1H), 4.52-4.36 (m, 2H), 3.50 (t, J=5.7 Hz, 2H), 3.01 (ddd, J=22.8, 13.4, 7.4 Hz, 2H), 2.66 (d, J=5.5 Hz, 2H), 1.58 (td, J=13.2, 6.6 Hz, 1H), 1.38-1.16 (m, 2H), 0.81 (dd, J=6.5, 2.7 Hz, 6H). $^{13}$C NMR (101 MHz, DMSO) δ 175.25, 172.44, 157.02, 138.32, 135.20, 134.39, 129.80, 128.90, 128.42, 126.60, 126.53, 126.38, 53.97, 45.73, 41.50, 37.81, 28.61, 25.58, 23.47, 23.15, 21.50. HRMS (ESI) calcd for $C_{25}H_{33}BN_3O_3$: 434.26139 [(M−H$_2$O+CH$_2$+H)], found 434.26060.

Example 29

N-L-phenylalanyl-L-leucine borate-N'—(N-methyl-benzylamine)-urea (hlq-U75)

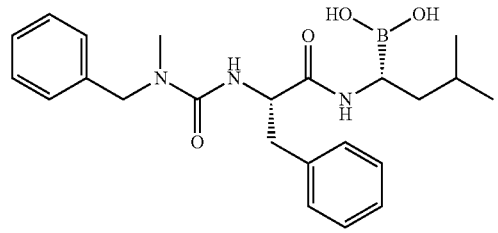

Using N-methyl-benzylamine as raw material instead of pyrazin-2-ylmethylamine, the synthetic approach was analogous to that described in example 2. White foam solid was obtained with a yield of 31%, mp: 111-114° C.

$^1$H NMR (400 MHz, DMSO) δ 8.71 (s, 1H), 7.31-7.18 (m, 8H), 6.99 (d, =6.9 Hz, 2H), 6.60 (d, J=8.4 Hz, 1H), 4.66 (td, J=9.1, 5.2 Hz, 1H), 4.36 (dd, J=75.5, 15.8 Hz, 2H), 3.04 (ddd, J=23.6, 13.6, 7.5 Hz, 2H), 2.70 (s, 3H), 1.65 (td, J=13.3, 6.7 Hz, 1H), 1.46-1.20 (m, 2H), 0.87 (d, J=6.5 Hz, 6H). $^{13}$C NMR (101 MHz, DMSO) δ 175.43, 157.65, 138.85, 138.34, 129.80, 128.73, 128.49, 127.51, 127.17, 126.68, 53.92, 51.53, 37.80, 34.13, 25.66, 23.54, 23.29. HRMS (ESI) calcd for $C_{24}H_{33}BN_3O_3$: 422.26137 [(M−$H_2O$+$CH_2$+H)$^+$], found 422.26058.

Example 30

N-L-phenylalanyl-L-leucine borate-N'-2,3-dimethyl-benzylamine-urea (hlq-U76)

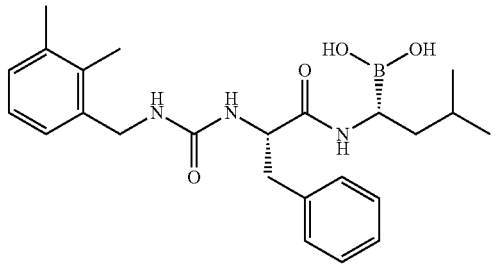 [SMILES: Cc1cccc(CNC(=O)N[C@@H](Cc2ccccc2)C(=O)N[C@@H](CC(C)C)B(O)O)c1C]

Using 2,3-dimethyl-benzylamine as raw material instead of pyrazin-2-ylmethylamine, the synthetic approach was analogous to that described in example 2. White foam solid was obtained with a yield of 19%, mp: 137-139° C.

$^1$H NMR (400 MHz, DMSO) δ 7.24 (s, 5H), 7.07-6.89 (m, 3H), 6.33 (s, 1H), 6.27 (d, J=8.2 Hz, 1H), 4.71-4.52 (m, 1H), 4.13 (ddd, J=26.3, 18.5, 6.4 Hz, 2H), 3.07-2.77 (m, 2H), 2.67 (s, 1H), 2.21 (s, 3H), 2.07 (s, 3H), 1.60 (td, J=13.2, 6.6 Hz, 1H), 1.30 (ddd, J=21.8, 12.4, 6.2 Hz, 2H), 0.84 (d, J=5.9 Hz, 6H). $^{13}$C NMR (101 MHz, DMSO) δ 174.86, 157.46, 138.14, 137.51, 136.58, 134.39, 129.89, 129.84, 128.78, 128.49, 126.79, 125.84, 125.56, 52.64, 42.11, 38.99, 25.57, 23.61, 23.47, 23.01, 20.46, 14.67. HRMS (ESI) calcd for $C_{25}H_{35}BN_3O_3$: 436.27704 [(M−$H_2O$+$CH_2$+H)$^+$], found 436.27918.

Example 31

N-L-phenylalanyl-L-leucine borate-N'-2,5-dichloro-benzylamine-urea (hlq-U79)

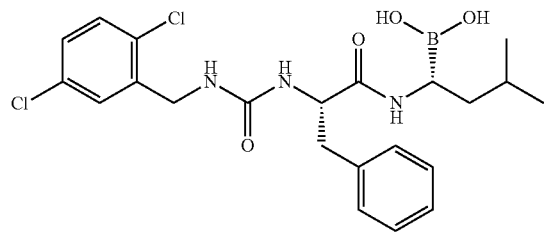 [SMILES: CC(C)C[C@H](NC(=O)[C@H](Cc1ccccc1)NC(=O)NCc1cc(Cl)ccc1Cl)B(O)O]

Using 2,5-dichloro-benzylamine as raw material instead of pyrazin-2-ylmethylamine, the synthetic approach was analogous to that described in example 2. White foam solid was obtained with a yield of 18%, mp: 118-120° C.

$^1$H NMR (400 MHz, DMSO) δ 7.41 (m, 1H), 7.23 (m, 7H), 6.65 (d, J=3.2 Hz, 1H), 6.53 (dd, J=10.2, 5.7 Hz, 1H), 4.59 (dd, J=13.7, 6.7 Hz, 1H), 4.26 (d, J=5.9 Hz, 1H), 4.16 (d, J=15.6 Hz, 3H), 3.01 (d, J=11.9 Hz, 1H), 2.88 (d, J=9.3 Hz, 1H), 2.69 (s, 1H), 1.59 (dt, J=17.1, 6.5 Hz, 1H), 1.40-1.22 (m, 2H), 0.84 (d, J=6.2 Hz, 6H). $^{13}$C NMR (101 MHz, DMSO) δ 174.25, 157.85, 140.58, 137.94, 132.34, 131.09, 130.80, 129.69, 128.61, 128.50, 126.88, 54.41, 41.02, 37.88, 25.56, 23.52, 23.45, 23.10, 23.00. HRMS (ESI) calcd for $C_{23}H_{29}BCl_2N_3O_3$: 476.16776 [(M−$H_2O$+$CH_2$+H)$^+$], found 476.16698.

Example 32

N-L-phenylalanyl-L-leucine borate-N'-p-phenyl-benzylamine-urea (hlq-U80)

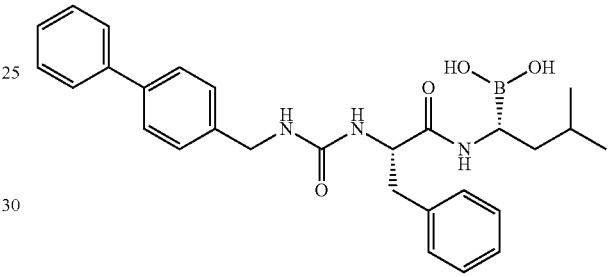

Using p-phenyl-benzylamine as raw material instead of pyrazin-2-ylmethylamine, the synthetic approach was analogous to that described in example 2. White foam solid was obtained with a yield of 19%, mp: 164-167° C.

$^1$H NMR (400 MHz, DMSO) δ 7.63 (d, J=8.3 Hz, 2H), 7.56 (d, J=7.1 Hz, 2H), 7.45 (t, J=7.5 Hz, 2H), 7.35 (t, J=7.3 Hz, 1H), 7.31-7.19 (m, 7H), 6.59 (s, 1H), 6.48-6.32 (m, 1H), 4.66 (dd, J=14.4, 7.0 Hz, 1H), 4.23 (ddd, J=20.6, 15.6, 5.8 Hz, 2H), 3.14-2.82 (m, 2H), 2.73 (t, J=16.0 Hz, 1H), 1.71-1.55 (m, 1H), 1.34 (ddd, J=24.5, 12.7, 6.3 Hz, 2H), 0.86 (d, J=6.0 Hz, 6H). $^{13}$C NMR (101 MHz, DMSO) δ 172.45, 157.72, 140.54, 140.23, 139.01, 137.54, 129.94, 129.89, 129.34, 128.53, 127.94, 127.70, 127.00, 126.96, 52.52, 43.04, 39.02, 25.61, 23.62, 23.05, 21.50. HRMS (ESI) calcd for $C_{29}H_{35}BN_3O_3$: 484.27710 [(M−$H_2O$+$CH_2$+H)$^+$], found 484.27583.

Example 33

N-L-phenylalanyl-L-leucine borate-N'-furan-2-ylm-ethylamine-urea (hlq-U81)

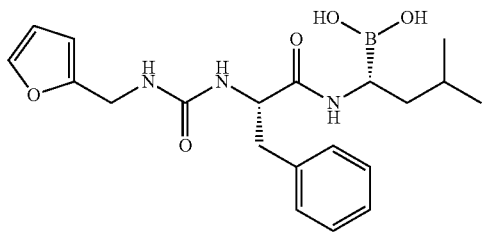 [SMILES: CC(C)C[C@H](NC(=O)[C@H](Cc1ccccc1)NC(=O)NCc1ccco1)B(O)O]

Using furan-2-ylmethylamine as raw material instead of pyrazin-2-ylmethylamine, the synthetic approach was analogous to that described in example 2. White foam solid was obtained with a yield of 30%, mp: 120-124° C.

$^1$H NMR (400 MHz, DMSO) δ 8.67 (s, 1H), 7.53 (d, J=0.9 Hz, 1H), 7.32-7.18 (m, 5H), 6.52-6.25 (m, 3H), 6.10 (d, J=2.7 Hz, 1H), 4.58 (dd, J=14.0, 7.9 Hz, 1H), 4.13 (qd, J=15.7, 5.7 Hz, 2H), 3.04-2.75 (m, 2H), 2.64 (d, J=3.3 Hz, 1H), 1.57 (dt, J=13.2, 6.6 Hz, 1H), 1.37-1.28 (m, 1H), 1.26-1.17 (m, 1H), 0.82 (dd, J=6.4, 3.2 Hz, 7H). $^{13}$C NMR (101 MHz, DMSO) δ 174.82, 157.35, 153.71, 142.28, 137.51, 129.84, 128.50, 126.82, 110.81, 106.64, 52.64, 38.94, 36.85, 25.56, 23.38, 23.24. HRMS (ESI) calcd for $C_{21}H_{29}BN_3O_4$: 398.22494 [(M–H$_2$O+CH$_2$+H)], found 398.22437.

Example 34

N-L-phenylalanyl-L-leucine borate-N'-naphth-1-ylmethylamine-urea (hlq-U82)

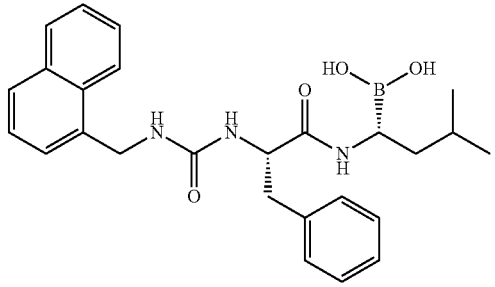 [SMILES: CC(C)C[C@H](NC(=O)[C@H](Cc1ccccc1)NC(=O)NCc1cccc2ccccc12)B(O)O]

Using naphth-1-ylmethylamine as raw material instead of pyrazin-2-ylmethylamine, the synthetic approach was analogous to that described in example 2. White foam solid was obtained with a yield of 32%, mp: 171-174° C.

$^1$H NMR (400 MHz, DMSO) δ 8.12-7.98 (m, 1H), 7.93 (dd, J=6.5, 2.8 Hz, 1H), 7.81 (d, J=8.2 Hz, 1H), 7.63-7.50 (m, 2H), 7.50-7.37 (m, 1H), 7.36-7.28 (m, 1H), 7.29-7.18 (m, 5H), 6.59 (d, J=3.0 Hz, 1H), 6.50-6.30 (m, 1H), 4.70 (dd, J=15.4, 6.0 Hz, 2H), 4.57 (dd, J=15.1, 5.3 Hz, 1H), 2.93 (ddd, J=27.6, 13.7, 7.1 Hz, 2H), 2.71 (s, 1H), 1.61 (dd, J=13.3, 6.6 Hz, 1H), 1.50-1.23 (m, 2H), 0.86 (d, J=6.3 Hz, 6H). $^{13}$C NMR (101 MHz, DMSO) δ 174.94, 157.59, 137.63, 136.04, 133.73, 131.26, 129.87, 128.91, 128.51, 127.74, 126.81, 126.57, 126.15, 125.87, 125.21, 123.82, 52.70, 41.34, 38.99, 25.61, 23.49, 23.23. HRMS (ESI) calcd for $C_{27}H_{33}BN_3O_3$: 458.26142 [(M–H$_2$O+CH$_2$+H)$^+$], found 458.26050.

Example 35

N-L-phenylalanyl-L-leucine borate-N'-3,4-difluoro-benzylamine-urea (hlq-U83)

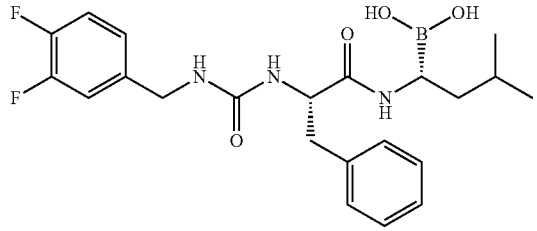 [SMILES: CC(C)C[C@H](NC(=O)[C@H](Cc1ccccc1)NC(=O)NCc1ccc(F)c(F)c1)B(O)O]

Using 3,4-difluoro-benzylamine as raw material instead of pyrazin-2-ylmethylamine, the synthetic approach was analogous to that described in example 2. White foam solid was obtained with a yield of 35%, mp: 163-166° C.

$^1$H NMR (400 MHz, DMSO) δ 7.67-7.43 (m, 1H), 7.30-7.17 (m, 6H), 7.13 (ddd, J=6.9, 6.2, 2.5 Hz, 1H), 6.93 (d, J=7.9 Hz, 1H), 6.67-6.56 (m, 1H), 6.50-6.36 (m, 1H), 4.57 (dd, J=14.0, 8.1 Hz, 1H), 4.23-4.01 (m, 2H), 3.07-2.75 (m, 2H), 2.65 (d, J=6.7 Hz, 1H), 1.67-1.48 (m, 1H), 1.35-1.23 (m, 2H), 0.82 (d, J=5.9 Hz, 6H). $^{13}$C NMR (101 MHz, DMSO) δ 174.84, 157.61, 150.30 (dd, J=12.7 Hz, 107.18 Hz), 147.93 (d, J=12.7 Hz, 105.52 Hz), 139.08, 137.55, 129.85, 128.47, 126.80, 123.73, 117.43 (d, J=16.9 Hz), 116.07 (d, =17.0 Hz), 52.53, 42.24, 38.84, 32.76, 25.53, 23.57, 23.53, 22.96. HRMS (ESI) calcd for $C_{23}H_{29}BF_2N_3O_3$: 444.22549 [(M–H$_2$O+CH$_2$+H)$^+$], found 444.22596.

Example 36

N-L-phenylalanyl-L-leucine borate-N'-3-nitro-benzylamine-urea (hlq-U84)

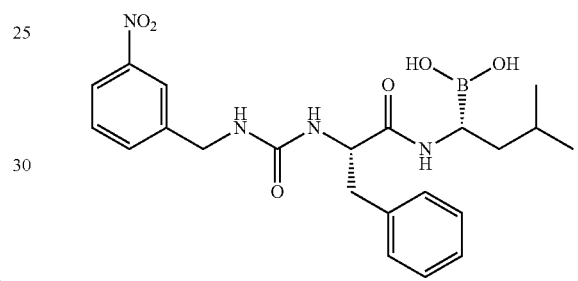

Using 3-nitro-benzylamine as raw material instead of pyrazin-2-ylmethylamine, the synthetic approach was analogous to that described in example 2. White foam solid was obtained with a yield of 35%, mp: 146-149° C.

$^1$H NMR (400 MHz, DMSO) δ 8.12-7.96 (m, 2H), 7.55 (dt, J=5.2, 2.8 Hz, 2H), 7.36-7.10 (m, 5H), 6.72 (s, 1H), 6.47 (dd, J=16.3, 8.6 Hz, 1H), 4.60 (dd, J=14.2, 7.9 Hz, 1H), 4.43-4.11 (m, 2H), 3.14-2.79 (m, 2H), 2.67 (d, J=6.3 Hz, 1H), 1.58 (dd, J=13.6, 6.8 Hz, 1H), 1.43-1.21 (m, 2H), 0.83 (d, J=4.8 Hz, 6H). $^{13}$C NMR (101 MHz, DMSO) δ 174.77, 157.66, 148.20, 143.77, 137.49, 134.01, 130.04, 129.87, 128.46, 126.76, 121.90, 121.82, 52.55, 42.65, 38.86, 25.55, 23.55, 22.97. HRMS (ESI) calcd for $C_{23}H_{30}BN_4O_5$: 453.23078 [(M–H$_2$O+CH$_2$+H)], found 453.22971.

Example 37

N-(1-oxo-1,2,3,4-dihydroisoquinolin-2-ylformyl)-L-phenylalanyl-L-leucine borate (hlq-U85)

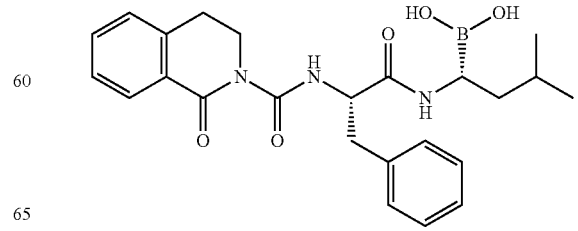

The product of example 28 was oxidized by being exposed to the air. White foam solid was obtained with a yield of 18%, mp: 182-184° C.

$^1$H NMR (400 MHz, DMSO) δ 8.95 (s, 1H), 8.04 (s, 1H), 7.46 (d, J=7.5 Hz, 1H), 7.39-7.09 (m, 7H), 6.83 (t, =6.5 Hz, 1H), 4.21 (d, J=5.5 Hz, 1H), 3.52-3.38 (m, 2H), 2.95-2.72 (m, 4H), 1.77 (dd, J=12.9, 6.8 Hz, 1H), 1.47 (ddd, J=20.9, 13.0, 6.3 Hz, 2H), 0.89 (t, J=5.7 Hz, 6H). $^{13}$C NMR (101 MHz, DMSO) δ 173.57, 171.24, 156.69, 138.09, 136.00, 132.04, 131.12, 130.96, 130.11, 128.55, 127.13, 126.79, 57.41, 50.95, 38.93, 37.15, 25.84, 23.56, 23.24, 21.58. HRMS (ESI) calcd for $C_{24}H_{31}BN_3O_4$: 448.24065 [(M−H$_2$O+CH$_2$+H)$^+$], found 448.23982.

Example 38

N-L-phenylalanyl-L-leucine borate-N'-1,2,3,4-tetra-hydroquinoline-urea (cq01)

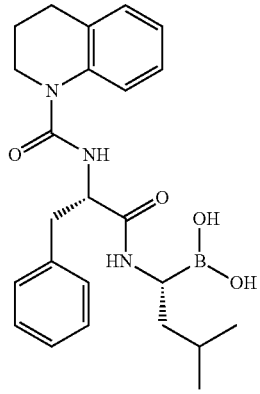 [SMILES: CC(C)C[C@H](NC(=O)[C@H](Cc1ccccc1)NC(=O)N1CCCc2ccccc21)B(O)O]

Synthesis of Intermediate a: N-L-phenylalanine methyl ester-N'-1,2,3,4-tetrahydroquinoline-urea

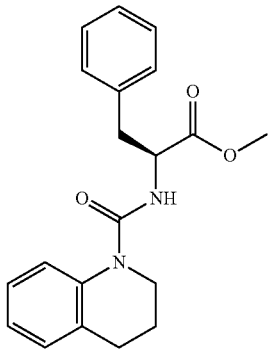 [SMILES: COC(=O)[C@H](Cc1ccccc1)NC(=O)N1CCCc2ccccc21]

To 20 mL of DCM was added triphosgene (1.49 g, 5 mmol), and mixture of 1,2,3,4-tetrahydroquinoline (1.33 g, 10 mmol) and triethylamine (2.1 mL, 15 mmol) in DCM were added dropwise in an ice bath. The mixture was allowed to increase to room temperature and react for 6 h. Then the mixture was quenched with water, partitioned. DCM layer was washed with water, then dried over anhydrous Na$_2$SO$_4$. After filtration, L-phenylalanine methyl ester hydrochloride (2.16 g, 10 mmol) and DIEA (3.8 mL, 22 mmol) were added, and was allowed to react overnight at room temperature. The reaction liquid was washed with water, and organic layer was dried over anhydrous Na$_2$SO$_4$. Column chromatography was applied to afford 2.2 g of white solid, with a yield of 65%, mp: 101-103° C.

$^1$H NMR (400 MHz, CDCl$_3$) δ 7.30-7.21 (m, 3H), 7.14-7.09 (m, 1H), 7.07 (dd, J=7.6, 1.8 Hz, 2H), 7.05-6.97 (m, 3H), 5.51 (d, J=7.6 Hz, 1H), 4.80 (td, J=7.3, 5.7 Hz, 1H), 3.79 (ddd, J=12.4, 7.0, 5.4 Hz, 1H), 3.72 (s, 3H), 3.60 (ddd, J=12.5, 7.2, 5.3 Hz, 1H), 3.17 (dd, J=13.8, 5.6 Hz, 1H), 3.01 (dd, J=13.9, 7.0 Hz, 1H), 2.72 (t, =6.7 Hz, 2H), 1.97-1.81 (m, 2H). $^{13}$C NMR (101 MHz, CDCl$_3$) δ 173.00, 155.85, 138.78, 136.27, 132.17, 129.46, 129.22, 128.67, 127.12, 126.59, 124.38, 123.11, 54.77, 52.30, 43.48, 37.95, 27.05, 23.88.

Synthesis of Intermediate b: N-L-phenylalanine-N'-1,2,3,4-tetrahydroquinoline-urea

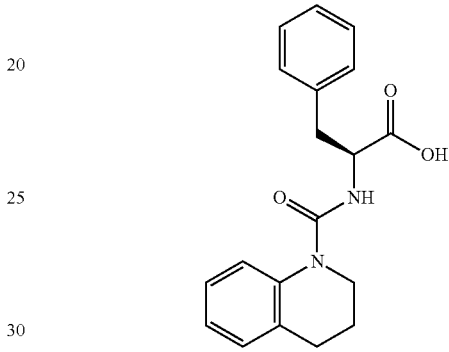

Intermediate a (2.2 g, 6.5 mmol) obtained from the previous step was dissolved in 20 mL of THF, to which 20 mL of water and sodium hydroxide (0.32 g, 8 mmol) were added. After 1 h, the reaction was showed to be complete with TLC monitoring. THF was evaporated under reduced pressure, and pH was adjusted to 2-3 with HCl, to afford plenty of solid. After filtration and drying, 2.1 g of yellow solid was obtained, with a yield of 95%.

Synthesis of Intermediate c: N-(L-phenylalanyl-L-leucine borate pinacol ester)-N'-1,2,3,4-tetra hydroquinoline-urea

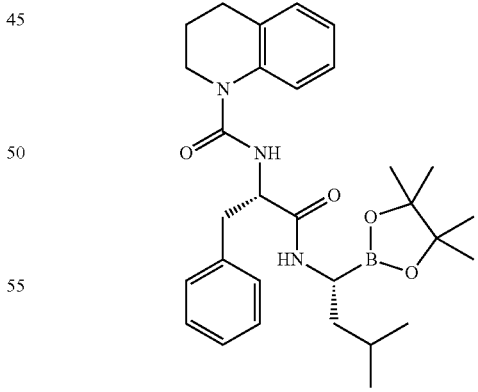

To 20 mL of DCM was sequentially added the intermediate b (0.65 g, 2 mmol) obtained from the previous step, HOBt (0.30 g, 2.2 mmol) and EDCl (0.46 g, 2.4 mmol). After 30-min reaction, L-leucine borate pinacol ester hydrochloride (0.50 g, 2 mmol) and DIEA (0.85 mL, 4.8 mmol) were added, and mixture was allowed to react overnight. A small amount of water was added to quench the reaction, DCM was evaporated under reduced pressure, and ethyl acetate was added. The mixture was washed with 0.5 N HCl, 2 N Na₂CO₃ and saturated brine, and organic layer was dried with anhydrous Na₂SO₄. After filtration, the solvent was evaporated under reduced pressure to afford 0.80 g of crude product, which was used in the next step directly.

Synthesis of the Title Compound: N-L-phenylalanyl-L-leucine borate-N'-1,2,3,4-tetrahydroquinoline-urea Intermediate c (0.80 g, 1.5 mmol) obtained from the previous step was dissolved in 20 mL of ethyl ether. Diethanolamine (0.15 g, 1.5 mmol) was added, and the mixture was allowed to react overnight. After suction filtration, the precipitate was completely washed with ethyl ether and dried. The obtained solid was suspended in 20 mL of ethyl acetate, and 20 mL of distilled water and 1 mL of 4N HCl were added, before vigorous stirring for 30 min. Water phase was removed by partition, and organic layer was washed with distilled water and saturated brine two times each, and dried over anhydrous Na₂SO₄. After filtration, the solvent was evaporated under reduced pressure to afford white foam solid, which was recrystallized by ethyl acetate and n-hexane to obtain 0.26 g of white solid with a yield of 49%, mp: 101-103° C.

$^1$H NMR (400 MHz, DMSO-d₆) δ 8.85-8.59 (m, 1H), 7.33-6.87 (m, 9H), 6.63 (d, J=8.2 Hz, 1H), 4.61 (td, J=8.7, 5.2 Hz, 1H), 3.59 (dt, =12.1, 5.9 Hz, 1H), 3.40 (dt, =12.3, 6.1 Hz, 1H), 3.06 (dd, J=13.7, 5.2 Hz, 1H), 2.95 (dd, J=13.7, 9.4 Hz, 1H), 2.74-2.52 (m, 3H), 1.71 (h, J=6.2 Hz, 2H), 1.60 (dq, J=13.5, 6.7 Hz, 1H), 1.41-1.22 (m, 2H), 0.82 (d, J=6.5 Hz, 6H). $^{13}$C NMR (101 MHz, DMSO-d₆) δ 174.32, 155.73, 138.89, 137.43, 129.90, 129.34, 128.58, 128.03, 126.33, 125.68, 123.25, 122.66, 53.30, 43.97, 40.21, 37.21, 26.55, 25.11, 23.15, 23.04, 22.59. HRMS (ESI) calcd for C₂₅H₃₃BN₃O₃: 434.26095 [(M−H₂O+CH₂+H)⁺], found 434.26180.

Example 39

N-L-phenylalanyl-L-leucine borate-N'-1-methyl-1,2,3,4-tetrahydroisoquinoline-urea (cq02)

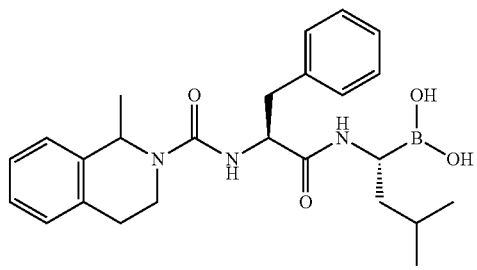 [SMILES: CC(C)C[C@H](NC(=O)[C@H](Cc1ccccc1)NC(=O)N1CCc2ccccc2C1C)B(O)O]

Using 1-methyl-1,2,3,4-tetrahydroisoquinoline as raw material instead of 1,2,3,4-tetrahydroquinoline, the synthetic approach of intermediates a to c was analogous to that described in example 38. Intermediate c (N-(L-phenylalanyl-L-leucine borate pinacol ester)-N'-1,2,3,4-tetrahydroisoquinoline-urea) (0.70 g, 1.3 mmol) was dissolved in 20 mL of ethyl ether, and anhydrous citric acid (0.25 g, 1.3 mmol) was added. The mixture was allowed to react overnight. After suction filtration, the precipitate was completely washed with ethyl ether and dried. The obtained solid was suspended in 20 mL of ethyl acetate, and 20 mL of saturated NaHCO₃ was added. After 30-min vigorous stirring and liquid partition, ethyl acetate layer was washed with saturated NaHCO₃ and saturated NaCl two times each, and dried over anhydrous Na₂SO₄. After filtration, the solvent was evaporated under reduced pressure to afford white foam solid, which was recrystallized by ethyl acetate and n-hexane to obtain 0.27 g of white solid with a yield of 30%.

$^1$H NMR (400 MHz, DMSO-d₆) δ 8.65 (d, J=16.9 Hz, 1H), 7.32-7.01 (m, 9H), 6.74 (d, =8.0 Hz, 1H), 5.15 (dq, J=14.0, 6.6 Hz, 1H), 4.60 (p, J=7.7 Hz, 1H), 3.96 (t, =14.3 Hz, 1H), 3.01 (ddt, J=47.3, 14.2, 8.0 Hz, 3H), 2.81-2.55 (m, 3H), 1.56 (dq, J=13.0, 6.4 Hz, 1H), 1.27 (tq, J=24.3, 10.6, 9.0 Hz, 5H), 0.79 (q, J=7.0 Hz, 6H). $^{13}$C NMR (101 MHz, DMSO-d₆) δ 174.92, 174.81, 155.99, 155.87, 138.89, 138.83, 137.92, 137.84, 133.99, 129.34, 129.23, 128.63, 127.97, 127.91, 126.72, 126.21, 126.11, 126.02, 125.87, 53.39, 49.31, 49.05, 40.24, 37.37, 37.20, 36.72, 36.51, 28.29, 25.11, 25.05, 23.03, 22.97, 22.70, 22.64, 21.80, 21.51. HRMS (ESI) calcd for C₂₆H₃₅BN₃O₃: 434.27660 [(M−H₂O+CH₂+H)⁺], found 434.27612.

Example 40

N-L-leucyl-L-leucine borate-N'-1,2,3,4-tetrahydroisoquinoline-urea (cq04)

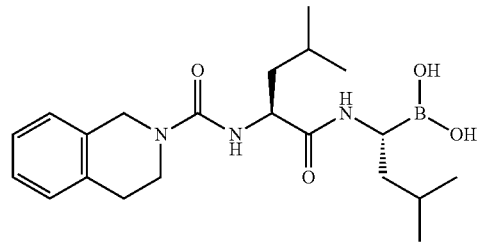 [SMILES: CC(C)C[C@H](NC(=O)[C@H](CC(C)C)NC(=O)N1CCc2ccccc2C1)B(O)O]

Synthesis of Precursor: 2-chloroformyl-1,2,3,4-tetrahydroisoquinoline

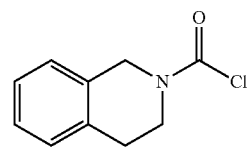 [SMILES: O=C(Cl)N1CCc2ccccc2C1]

To 20 mL of DCM was added triphosgene (1.49 g, 5 mmol), and mixture of 1,2,3,4-tetrahydroisoquinoline (1.33 g, 10 mmol) and triethylamine (2.1 mL, 15 mmol) in DCM were added dropwise in an ice bath. The mixture was allowed to increase to room temperature and react for 6 h. Then the mixture was quenched with water, partitioned. DCM layer was washed with water, then dried over anhydrous Na₂SO₄. Column chromatography was applied to afford 1.6 g of colorless oil, with a yield of 82%.

Synthesis of Intermediate a: N-L-leucine methyl ester-N'-1,2,3,4-tetrahydroisoquinoline-urea

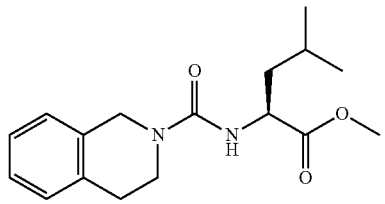 [SMILES: COC(=O)[C@H](CC(C)C)NC(=O)N1CCc2ccccc2C1]

The precursor (1.37 g, 7 mmol) obtained from the previous step was dissolved in 20 mL of DCM. L-leucine methyl ester hydrochloride (1.27 g, 7 mmol) and DIEA (2.7 mL, 15.4 mmol) were added, and was allowed to react overnight at room temperature. The reaction liquid was washed with water, and dried over anhydrous $Na_2SO_4$. Column chromatography was applied to afford 1.8 g of oil, with a yield of 84%.

$^1$H NMR (400 MHz, $CDCl_3$) δ 7.26-7.01 (m, 4H), 5.23 (d, J=8.2 Hz, 1H), 4.58 (dt, =8.6, 4.4 Hz, 1H), 4.54 (d, J=1.7 Hz, 2H), 3.73 (s, 3H), 3.66 (ddd, J=11.9, 6.7, 5.0 Hz, 1H), 3.53 (ddd, J=12.2, 7.0, 5.0 Hz, 1H), 2.93-2.73 (m, 2H), 1.75 (dq, J=8.0, 6.3 Hz, 1H), 1.68-1.50 (m, 2H), 0.95 (d, J=6.5 Hz, 6H). $^{13}$C NMR (101 MHz, $CDCl_3$) δ 175.30, 157.13, 134.98, 133.29, 128.30, 126.57, 126.32, 52.15, 45.37, 41.76, 41.19, 28.95, 24.88, 22.91, 21.92.

Starting from the intermediate a obtained from the previous step, the synthetic approach was analogous to that described in example 38 to afford the title compound as white solid with a yield of 43%, mp: 108-110° C.

$^1$H NMR (400 MHz, DMSO-$d_6$) δ 8.56 (s, 1H), 7.14 (td, J=7.5, 6.7, 3.3 Hz, 4H), 6.65 (d, S=8.1 Hz, 1H), 4.70-4.26 (m, 3H), 3.58 (qd, J=6.6, 3.8 Hz, 2H), 2.76 (t, =6.2 Hz, 2H), 2.54 (dd, J=7.6, 3.4 Hz, 1H), 1.61 (dhept, J=20.4, 7.5, 6.9 Hz, 3H), 1.48 (dq, J=12.6, 7.5, 6.5 Hz, 1H), 1.24 (ddq, J=36.5, 13.4, 7.1 Hz, 2H), 0.93-0.72 (m, 12H). $^{13}$C NMR (101 MHz, DMSO-$d_6$) δ 175.91, 156.66, 134.79, 134.01, 128.48, 126.20, 126.15, 125.95, 50.09, 45.28, 41.00, 40.52, 40.20, 28.32, 25.15, 24.09, 22.96, 22.91, 21.50. HRMS (ESI) calcd for $C_{22}H_{35}BN_3O_3$: 400.27660 [(M−$H_2O$+$CH_2$+H)$^+$], found 400.27683.

Example 41

N-L-alanyl-L-leucine borate-N'-1,2,3,4-tetrahydroisoquinoline-urea (cq05)

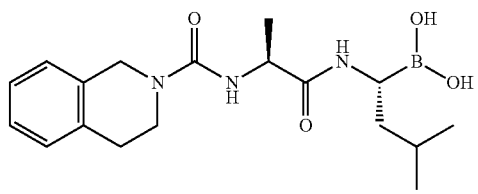 [SMILES: CC(C)C[C@H](NC(=O)[C@H](C)NC(=O)N1CCc2ccccc2C1)B(O)O]

Using L-alanine methyl ester hydrochloride as raw material instead of L-leucine methyl ester hydrochloride, the synthetic approach of intermediate a (N-L-alanine methyl ester-N'-1,2,3,4-tetrahydroisoquinoline-urea) was analogous to that described in example 40. Colorless oil was obtained with a yield of 70%.

$^1$H NMR (400 MHz, $CDCl_3$) δ 7.15 (ddd, J=18.7, 9.5, 4.4 Hz, 4H), 5.21 (d, J=7.3 Hz, 1H), 4.64-4.49 (m, 3H), 3.75 (s, 3H), 3.70-3.53 (m, 2H), 2.95-2.80 (m, 2H), 1.43 (d, J=7.2 Hz, 3H). $^{13}$C NMR (101 MHz, $CDCl_3$) δ 175.00, 156.78, 135.06, 133.31, 128.41, 126.70, 126.43, 126.39, 52.41, 49.39, 45.46, 41.21, 29.04, 19.08.

Starting from the intermediate a obtained from the previous step, the synthetic approach was analogous to that described in example 38 to afford the title compound as white solid with a yield of 21%, mp: 111-113° C.

$^1$H NMR (400 MHz, DMSO-$d_6$) δ 8.64 (s, 1H), 7.14 (td, J=7.2, 6.4, 4.3 Hz, 4H), 6.74 (d, S=7.6 Hz, 1H), 4.61-4.44 (m, 2H), 4.40 (p, J=7.2 Hz, 1H), 3.58 (q, J=6.2 Hz, 2H), 2.77 (t, =5.8 Hz, 2H), 2.57 (q, J=6.7 Hz, 1H), 1.60 (dt, =13.4, 6.7 Hz, 1H), 1.36-1.17 (m, 5H), 0.80 (d, J=7.2 Hz, 6H). $^{13}$C NMR (101 MHz, DMSO-$d_6$) δ 176.19, 156.50, 134.82, 133.96, 128.48, 126.20, 126.16, 125.99, 47.36, 45.23, 40.90, 40.19, 28.34, 25.17, 22.93, 22.90, 18.18. HRMS (ESI) calcd for $C_{19}H_{29}BN_3O_3$: 358.22965 [(M−$H_2O$+$CH_2$+H)$^+$], found 358.22831.

Example 42

N-L-valyl-L-leucine borate-N'-1,2,3,4-tetrahydroisoquinoline-urea (cq06)

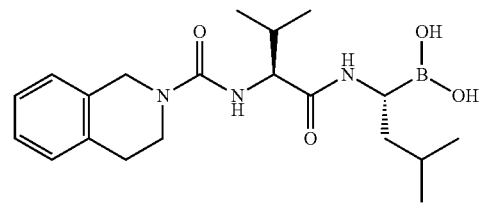 [SMILES: CC(C)C[C@H](NC(=O)[C@@H](NC(=O)N1CCc2ccccc2C1)C(C)C)B(O)O]

Using L-valine methyl ester hydrochloride as raw material instead of L-leucine methyl ester hydrochloride, the synthetic approach of intermediate a (N-L-valine methyl ester-N'-1,2,3,4-tetrahydroisoquinoline-urea) was analogous to that described in example 40. Colorless oil was obtained with a yield of 64%.

$^1$H NMR (400 MHz, $CDCl_3$) δ 7.25-7.06 (m, 4H), 5.06 (d, J=8.4 Hz, 1H), 4.58 (s, 2H), 4.51 (dd, J=8.3, 5.0 Hz, 1H), 3.74 (s, 3H), 3.72-3.66 (m, 1H), 3.59 (ddd, J=12.2, 6.8, 5.2 Hz, 1H), 2.88 (q, J=5.3 Hz, 2H), 2.16 (qd, J=7.1, 5.3 Hz, 1H), 0.95 (dd, J=11.3, 6.8 Hz, 6H). $^{13}$C NMR (101 MHz, $CDCl_3$) δ 174.01, 157.21, 135.09, 133.35, 128.39, 126.71, 126.44, 126.40, 58.54, 52.10, 45.49, 41.31, 31.45, 29.06, 19.08, 18.11.

Starting from the intermediate a obtained from the previous step, the synthetic approach was analogous to that described in example 38 to afford the title compound as white solid with a yield of 33%, mp: 114-115° C.

$^1$H NMR (400 MHz, DMSO-$d_6$) δ 8.72 (s, 1H), 7.15 (td, J=6.3, 2.6 Hz, 4H), 6.48 (d, J=8.5 Hz, 1H), 4.63-4.44 (m, 2H), 4.11 (t, J=8.2 Hz, 1H), 3.59 (t, J=5.9 Hz, 2H), 2.77 (t, J=5.9 Hz, 2H), 2.57 (dt, =10.0, 4.8 Hz, 1H), 2.03 (dq, J=13.9, 6.7 Hz, 1H), 1.61 (dp, S=13.4, 6.6 Hz, 1H), 1.24 (ddq, J=20.6, 13.9, 7.2 Hz, 2H), 0.93-0.73 (m, 12H). $^{13}$C NMR (101 MHz, DMSO-$d_6$) δ 174.74, 156.81, 134.74, 133.99, 128.47, 126.17, 126.14, 125.94, 57.34, 45.37, 41.13, 40.25, 30.08, 28.28, 25.08, 23.13, 22.50, 19.10, 18.97. HRMS (ESI) calcd for $C_{21}H_{33}BN_3O_3$: 386.26095 [(M−$H_2O$+$CH_2$+H)$^+$], found 386.26223.

Example 43

N-L-naphthylalanyl-L-leucine borate-N'-1,2,3,4-tetrahydroisoquinoline-urea (cq07)

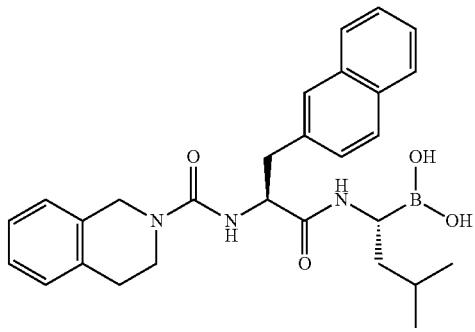 [SMILES: CC(C)C[C@H](NC(=O)[C@H](Cc1ccc2ccccc2c1)NC(=O)N1CCc2ccccc2C1)B(O)O]

Using L-naphthylalanine methyl ester hydrochloride as raw material instead of L-leucine methyl ester hydrochloride, the synthetic approach of intermediate a (N-L-naphthylalanine methyl ester-N'-1,2,3,4-tetrahydroisoquinoline-urea) was analogous to that described in example 40 to afford white foam solid with a yield of 77%.

$^1$H NMR (400 MHz, CDCl$_3$) δ 7.85-7.65 (m, 3H), 7.57 (d, J=1.6 Hz, 1H), 7.44 (dt, =6.3, 3.5 Hz, 2H), 7.27-7.22 (m, 1H), 7.16 (dt, J=7.4, 3.8 Hz, 2H), 7.13-7.09 (m, 1H), 7.07-7.02 (m, 1H), 5.02 (d, J=7.5 Hz, 1H), 4.94 (dt, J=7.5, 5.8 Hz, 1H), 4.58-4.39 (m, 2H), 3.72 (s, 3H), 3.59 (ddd, J=12.0, 6.6, 5.1 Hz, 1H), 3.49 (ddd, J=12.2, 6.7, 5.2 Hz, 1H), 3.37-3.23 (m, 2H), 2.80 (q, J=5.3 Hz, 2H). $^{13}$C NMR (101 MHz, CDCl$_3$) δ 173.30, 156.59, 135.03, 133.95, 133.50, 133.30, 132.51, 128.44, 128.25, 128.11, 127.74, 127.59, 127.53, 126.75, 126.47, 126.41, 126.24, 125.78, 54.55, 52.36, 45.47, 41.30, 38.67, 28.97.

Starting from the intermediate a obtained from the previous step, the synthetic approach was analogous to that described in example 38 to afford the intermediate b (N-L-naphthylalanine-N'-1,2,3,4-tetrahydroisoquinoline-urea) as white solid with a yield of 88%.

Starting from the intermediate b obtained from the previous step, the synthetic approach was analogous to that described in example 39 to afford the title compound as white solid with a yield of 30%, mp: 112-114° C.

$^1$H NMR (400 MHz, DMSO-d$_6$) δ 8.74 (s, 1H), 7.76 (ddd, J=19.2, 11.8, 5.9 Hz, 4H), 7.50-7.36 (m, 3H), 7.20-6.97 (m, 4H), 6.86 (d, J=8.2 Hz, 1H), 4.69 (q, J=7.8 Hz, 1H), 4.44 (q, J=16.5 Hz, 2H), 3.48 (t, J=6.0 Hz, 2H), 3.32-3.08 (m, 2H), 2.79-2.54 (m, 3H), 1.57 (dq, J=13.8, 6.9 Hz, 1H), 1.31 (ddt, =56.5, 13.7, 7.4 Hz, 2H), 0.79 (dd, J=20.2, 6.4 Hz, 6H). $^{13}$C NMR (101 MHz, DMSO-d$_6$) δ 174.75, 156.51, 135.50, 134.65, 133.86, 132.94, 131.80, 128.41, 127.99, 127.74, 127.38, 126.11, 126.03, 125.89, 125.76, 125.31, 53.55, 45.25, 40.99, 37.59, 28.11, 25.10, 22.97, 22.69. HRMS (ESI) calcd for C$_{29}$H$_{35}$BN$_3$O$_3$: 484.27660 [(M−H$_2$O+CH$_2$+H)], found 484.27549.

Example 44

N-L-isoleucyl-L-leucine borate-N'-1,2,3,4-tetrahydroisoquinoline-urea (cq08)

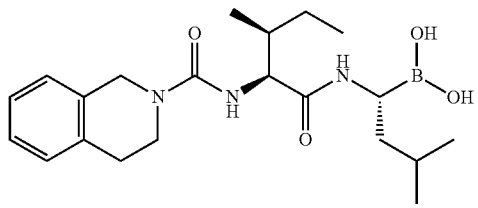 [SMILES: CC[C@H](C)[C@H](NC(=O)N1CCc2ccccc2C1)C(=O)N[C@@H](CC(C)C)B(O)O]

Using L-isoleucine methyl ester hydrochloride as raw material instead of L-leucine methyl ester hydrochloride, the synthetic approach of intermediate a (N-L-isoleucine methyl ester-N'-1,2,3,4-tetrahydroisoquinoline-urea) was analogous to that described in example 40. Colorless oil was obtained with a yield of 84%.

$^1$H NMR (400 MHz, CDCl$_3$) δ 7.24-7.09 (m, 4H), 5.12 (d, J=8.2 Hz, 1H), 4.60-4.52 (m, 3H), 3.74 (s, 3H), 3.72-3.65 (m, 1H), 3.58 (ddd, J=12.0, 6.8, 5.1 Hz, 1H), 2.98-2.76 (m, 2H), 1.89 (dddt, =11.1, 6.6, 4.2, 1.8 Hz, 1H), 1.49 (ddt, =14.8, 7.6, 3.8 Hz, 1H), 1.21 (ddd, J=13.6, 9.1, 7.2 Hz, 1H), 1.02-0.86 (m, 6H). $^{13}$C NMR (101 MHz, CDCl$_3$) δ 173.98, 157.05, 135.06, 133.30, 128.36, 126.67, 126.40, 126.36, 57.79, 52.03, 45.41, 41.21, 38.16, 29.02, 25.40, 15.51, 11.64.

Starting from the intermediate a obtained from the previous step, the synthetic approach was analogous to that described in example 38 to afford the title compound as white solid with a yield of 35%, mp: 108-110° C.

$^1$H NMR (400 MHz, DMSO-d$_6$) δ 8.76-8.45 (m, 1H), 7.31-6.99 (m, 4H), 6.49 (d, J=8.4 Hz, 1H), 4.52 (d, J=3.7 Hz, 2H), 4.16 (t, =8.4 Hz, 1H), 3.57 (t, =5.8 Hz, 2H), 2.76 (t, =5.8 Hz, 2H), 2.57 (q, J=7.3, 6.4 Hz, 1H), 1.92-1.73 (m, 1H), 1.68-1.43 (m, 2H), 1.20 (dtt, J=40.7, 14.2, 7.0 Hz, 3H), 0.81 (dt, J=15.7, 5.6 Hz, 12H). $^{13}$C NMR (101 MHz, DMSO-d$_6$) δ 174.66, 156.74, 134.74, 134.00, 128.47, 126.16, 125.94, 56.03, 45.37, 41.11, 40.27, 35.91, 28.30, 25.09, 24.82, 23.16, 22.51, 15.23, 10.69. HRMS (ESI) calcd for C$_{22}$H$_{35}$BN$_3$O$_3$: 400.27660 [(M−H$_2$O+CH$_2$+H)$^+$], found 400.27769.

Example 45

N-L-tryptophanyl-L-leucine borate-N'-1,2,3,4-tetrahydroisoquinoline-urea (cq09)

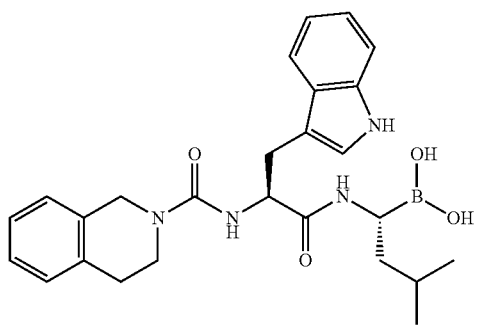 [SMILES: CC(C)C[C@H](NC(=O)[C@H](Cc1c[nH]c2ccccc12)NC(=O)N1CCc2ccccc2C1)B(O)O]

Using L-tryptophane methyl ester hydrochloride as raw material instead of L-leucine methyl ester hydrochloride, the synthetic approach of intermediate a (N-L-tryptophane methyl ester-N'-1,2,3,4-tetrahydroisoquinoline-urea) was analogous to that described in example 40. White solid was obtained with a yield of 83%, mp: 60-62° C.

$^1$H NMR (400 MHz, CDCl$_3$) δ 8.67 (s, 1H), 7.58-7.50 (m, 1H), 7.32 (dd, J=8.2, 0.9 Hz, 1H), 7.19-6.89 (m, 7H), 5.05 (d, J=7.6 Hz, 1H), 4.87 (dt, J=7.6, 5.3 Hz, 1H), 4.38 (q, S=15.6 Hz, 2H), 3.67 (s, 3H), 3.52 (ddd, J=12.0, 6.8, 5.1 Hz, 1H), 3.42 (ddd, J=12.2, 6.7, 5.1 Hz, 1H), 3.38-3.27 (m, 2H), 2.74 (q, J=5.6 Hz, 2H). $^{13}$C NMR (101 MHz, CDCl$_3$) δ 173.59, 156.89, 136.29, 135.02, 133.22, 128.38, 127.86, 126.69, 126.40, 126.37, 122.95, 122.17, 119.54, 118.54, 111.53, 110.11, 54.73, 52.31, 45.41, 41.16, 28.93, 27.98.

Starting from the intermediate a obtained from the previous step, the synthetic approach of intermediate b (N-L-tryptophane-N'-1,2,3,4-tetrahydroisoquinoline-urea) was analogous to that described in example 38. White solid was obtained with a yield of 92%.

Starting from the intermediate b obtained from the previous step, the synthetic approach was analogous to that described in example 39 to afford the title compound as white solid with a yield of 29%, mp: 130-132° C.

$^1$H NMR (400 MHz, DMSO-d$_6$) δ 10.96-10.72 (m, 1H), 8.74 (s, 1H), 7.60 (d, J=7.9 Hz, 1H), 7.32 (d, J=8.1 Hz, 1H), 7.23 (d, J=2.3 Hz, 1H), 7.18-6.99 (m, 5H), 6.93 (t, =7.4 Hz, 1H), 6.60 (d, J=8.0 Hz, 1H), 4.64 (q, J=7.3 Hz, 1H), 4.55-4.32 (m, 2H), 3.49 (t, J=6.0 Hz, 2H), 3.27-3.08 (m, 2H), 2.68 (dq, J=13.0, 6.8 Hz, 3H), 1.63 (dt, =13.3, 6.7 Hz, 1H), 1.34 (ddt, J=63.6, 13.3, 6.8 Hz, 2H), 0.82 (dd, J=6.6, 2.9 Hz, 6H). $^{13}$C NMR (101 MHz, DMSO-d$_6$) δ 175.39, 156.56, 136.06, 134.75, 133.83, 128.41, 127.43, 126.16, 126.06, 125.95, 124.02, 120.81, 118.37, 118.26, 111.31, 109.86, 52.94, 45.19, 40.94, 40.24, 28.24, 27.40, 25.24, 22.99, 22.93. HRMS (ESI) calcd for C$_{27}$H$_{34}$BN$_4$O$_3$: 473.27185 [(M−H$_2$O+CH$_2$+H)$^+$], found 473.27289.

Example 46

N-L-phenylalanyl-L-leucine borate-N'-7-nitro-1,2,3,4-tetrahydroisoquinoline-urea (cq10)

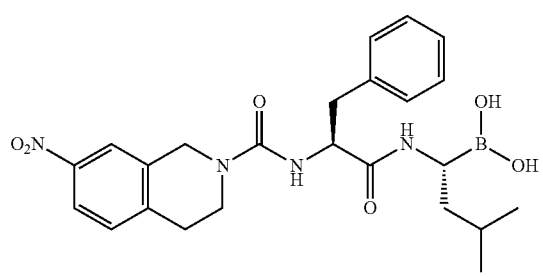 [SMILES: CC(C)C[C@H](NC(=O)[C@H](Cc1ccccc1)NC(=O)N1CCc2ccc([N+](=O)[O-])cc2C1)B(O)O]

Synthesis of Precursor: 7-nitro-1,2,3,4-tetrahydroisoquinoline hydrochloride

To 11 mL of concentrated sulfuric acid in an ice bath was added 1,2,3,4-tetrahydroisoquinoline (2.9 g, 21 mmol), and potassium nitrate (2.4 g, 24 mmol) was added slowly. The mixture was allowed to increase to room temperature and react overnight. Then the reaction liquid was poured into ice water, and pH was adjusted to around 10 with concentrated aqueous ammonia. After extraction with DCM three times, organic layers were combined and dried over anhydrous Na$_2$SO$_4$. After filtration, the solvent was evaporated under reduced pressure to obtain oil. The oil was dissolved in 16 mL of ethanol in an ice bath, and 3 mL of concentrated HCl was added to generate plenty of solid, which was subjected to suction filtration and drying. After recrystallization with methanol, 1.9 g of beige solid was obtained with a yield of 42%.

Starting from the precursor obtained from the previous step, the synthetic approach of intermediate c (N-L-phenylalanyl-L-leucine borate pinacol ester-N'-7-nitro-1,2,3,4-tetrahydroisoquinoline-urea) was analogous to that described in example 38 to afford 0.61 g of foam solid, which was used in the next step directly.

The intermediate c (0.61 g, 1.1 mmol) obtained from the previous step was dissolved in 20 mL of ethyl acetate, and diethanolamine (0.12 g, 1.1 mmol) was added, before overnight reaction at room temperature. No solid was generated from the system, and 20 mL of distilled water and 1 mL of 4N HCl were added, before vigorous stirring form 30 min. Water phase was removed by liquid partition, and organic phase was washed with saturated brine two times, then dried over anhydrous Na$_2$SO$_4$. After filtration, the solvent was evaporated under reduced pressure to afford yellow foam solid. Column chromatography was applied to obtain 80 mg of white solid with a yield of 11%, mp: 128-130° C.

$^1$H NMR (400 MHz, DMSO-d$_6$) δ 8.70 (s, 1H), 8.06-7.89 (m, 2H), 7.36 (d, =8.4 Hz, 1H), 7.27-7.10 (m, 5H), 6.95 (d, J=8.3 Hz, 1H), 4.66-4.43 (m, 3H), 3.54 (q, J=7.1, 6.0 Hz, 2H), 3.04 (dd, =13.8, 5.5 Hz, 1H), 2.97-2.87 (m, 1H), 2.75 (tq, =17.5, 10.9, 8.4 Hz, 2H), 2.61 (q, =6.6 Hz, 1H), 1.54 (dh, =14.6, 7.4, 6.9 Hz, 1H), 1.24 (ddt, =42.7, 13.8, 7.3 Hz, 2H), 0.77 (t, J=5.6 Hz, 6H). $^{13}$C NMR (101 MHz, DMSO-d$_6$) δ 174.69, 156.42, 145.64, 143.18, 137.79, 135.98, 130.00, 129.30, 129.22, 127.95, 127.89, 126.19, 121.13, 120.98, 53.52, 45.17, 40.63, 37.32, 28.14, 25.08, 23.01, 22.67. HRMS (ESI) calcd for C$_{25}$H$_{32}$BN$_4$O$_5$: 479.24603 [(M−H$_2$O+CH$_2$+H)$^+$], found 479.24737.

Example 47

N-L-homophenylalanyl-L-leucine borate-N'-1,2,3,4-tetrahydroisoquinoline-urea (cq14)

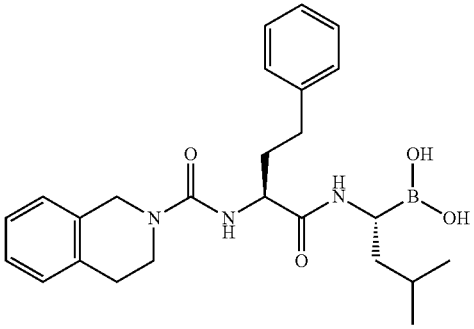 [SMILES: CC(C)C[C@H](NC(=O)[C@H](CCc1ccccc1)NC(=O)N1CCc2ccccc2C1)B(O)O]

Using L-homophenylalanine methyl ester as raw material instead of L-leucine methyl ester hydrochloride, the synthetic approach of intermediate a ( ) was analogous to that described in example 40. White foam solid was obtained with a yield of 90%.

$^1$H NMR (400 MHz, CDCl$_3$) δ 7.31-7.05 (m, 10H), 5.07 (d, J=7.6 Hz, 1H), 4.65 (td, J=7.6, 4.9 Hz, 1H), 4.53-4.34 (m, 2H), 3.72 (s, 3H), 3.60 (ddd, J=12.0, 6.6, 5.0 Hz, 1H), 3.48

(ddd, J=12.2, 6.9, 5.1 Hz, 1H), 2.82 (q, J=5.5 Hz, 2H), 2.71 (t, =7.7 Hz, 2H), 2.22 (dtd, J=15.9, 7.9, 4.9 Hz, 1H), 2.11-2.00 (m, 1H). $^{13}$C NMR (101 MHz, CDCl$_3$) δ 174.23, 156.86, 141.15, 135.04, 133.26, 128.55, 128.50, 128.40, 126.67, 126.40, 126.37, 126.18, 53.66, 52.34, 45.31, 41.10, 34.09, 31.96, 29.03.

Starting from the intermediate a obtained from the previous step, the synthetic approach was analogous to that described in example 38 to afford the title compound as white solid with a yield of 24%, mp: 103-104° C. 5 $^1$H NMR (400 MHz, DMSO-d$_6$) δ 8.57 (t, J=3.4 Hz, 1H), 7.30-7.05 (m, 9H), 6.71 (d, J=8.0 Hz, 1H), 4.52 (q, J=16.5 Hz, 2H), 4.42-4.25 (m, 1H), 3.59 (dt, J=11.6, 5.7 Hz, 2H), 2.78 (q, J=7.5, 6.1 Hz, 2H), 2.58 (dtd, J=17.9, 12.2, 10.1, 4.7 Hz, 3H), 2.03-1.86 (m, 2H), 1.67-1.51 (m, 1H), 1.25 (ddq, J=42.7, 13.3, 7.0 Hz, 2H), 0.77 (dd, J=18.5, 6.7 Hz, 6H). $^{13}$C NMR (101 MHz, DMSO-d$_6$) δ 175.31, 156.69, 141.32, 134.80, 133.99, 128.48, 128.28, 128.22, 128.19, 126.17, 126.13, 125.95, 125.72, 51.51, 45.32, 41.01, 33.56, 31.63, 28.29, 25.14, 22.87, 22.81. HRMS (ESI) calcd for C$_{26}$H$_{35}$BN$_3$O$_3$: 448.27660 [(M−H$_2$O+CH$_2$+H)$^+$], found 448.27649.

Example 48

N-L-4-nitro-phenylalanyl-L-leucine borate-N'-1,2,3,4-tetrahydroisoquinoline-urea (cq15)

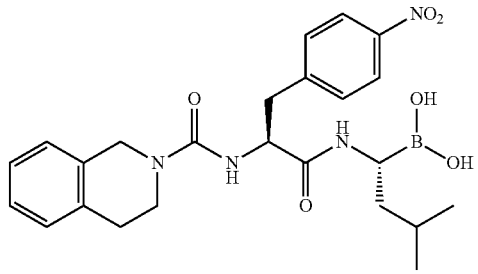 [SMILES: CC(C)C[C@H](NC(=O)[C@H](Cc1ccc([N+](=O)[O-])cc1)NC(=O)N1CCc2ccccc2C1)B(O)O]

Using L-4-nitro-phenylalanine methyl ester as raw material instead of L-phenylalanine methyl ester hydrochloride, the synthetic approach of intermediate a (N-L-4-nitro-phenylalanine methyl ester-N'-1,2,3,4-tetrahydroisoquinoline-urea) was analogous to that described in example 40. White foam solid was obtained with a yield of 83%.

$^1$H NMR (400 MHz, CDCl$_3$) δ 8.16-8.04 (m, 2H), 7.29 (dd, J=9.1, 7.2 Hz, 2H), 7.25-7.04 (m, 4H), 5.15 (d, J=7.1 Hz, 1H), 5.00-4.87 (m, 1H), 4.61-4.44 (m, 2H), 3.75 (s, 3H), 3.65 (ddd, J=11.9, 6.6, 5.0 Hz, 1H), 3.53 (ddd, J=12.3, 7.0, 5.1 Hz, 1H), 3.35-3.17 (m, 2H), 2.85 (q, J=5.7 Hz, 2H). $^{13}$C NMR (101 MHz, CDCl$_3$) δ 172.69, 156.41, 147.06, 144.50, 134.87, 133.10, 130.28, 128.48, 126.90, 126.55, 126.35, 123.62, 54.28, 52.61, 45.54, 41.38, 38.50, 28.85.

Starting from the intermediate a obtained from the previous step, the synthetic approach was analogous to that described in example 38 to afford the title compound as white solid with a yield of 15%, mp: 126-128° C.

$^1$H NMR (400 MHz, DMSO-d$_6$) δ 8.84-8.66 (m, 1H), 8.02 (d, J=8.2 Hz, 2H), 7.52 (dd, J=11.1, 7.1 Hz, 2H), 7.21-6.99 (m, 4H), 6.89 (d, J=8.3 Hz, 1H), 4.64 (q, J=8.1 Hz, 1H), 4.50-4.35 (m, 2H), 3.49 (dtd, J=19.0, 12.8, 6.2 Hz, 2H), 3.13 (ddd, J=35.7, 13.2, 7.4 Hz, 2H), 2.65 (q, J=9.2, 6.5 Hz, 3H), 1.52 (dq, J=13.1, 6.6 Hz, 1H), 1.22 (ddt, J=39.4, 13.7, 7.1 Hz, 2H), 0.78 (q, J=7.4, 5.7 Hz, 6H). $^{13}$C NMR (101 MHz, DMSO-d$_6$) δ 174.22, 156.45, 146.08, 134.61, 133.79, 130.68, 128.41, 126.15, 126.02, 125.88, 122.96, 52.90, 45.27, 40.98, 37.14, 27.99, 25.02, 22.94, 22.52. HRMS (ESI) calcd for C$_{25}$H$_{32}$BN$_4$O$_5$: 479.24603 [(M−H$_2$O+CH$_2$+H)], found 479.24483.

Example 49

N-L-glutamyl-L-leucine borate-N'-1,2,3,4-tetrahydroisoquinoline-urea (cq18)

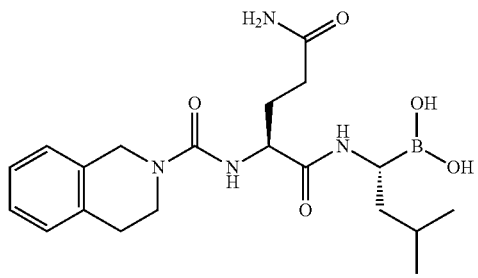 [SMILES: CC(C)C[C@H](NC(=O)[C@H](CCC(N)=O)NC(=O)N1CCc2ccccc2C1)B(O)O]

Using L-glutamine methyl ester hydrochloride as raw material instead of L-leucine methyl ester hydrochloride, the synthetic approach of intermediate a ( ) was analogous to that described in example 40. White solid was obtained with a yield of 44%, mp: 122-124° C.

$^1$H NMR (400 MHz, CDCl$_3$) δ 7.22-7.06 (m, 4H), 6.74 (s, 1H), 6.04 (d, J=20.5 Hz, 2H), 4.54 (s, 2H), 4.44 (dd, J=9.1, 4.3 Hz, 1H), 3.71 (s, 3H), 3.66-3.52 (m, 2H), 2.84 (t, =6.0 Hz, 2H), 2.36 (tddd, J=15.6, 12.6, 7.6, 3.8 Hz, 2H), 2.18-2.08 (m, 1H), 2.01 (dddd, J=14.3, 8.4, 5.3, 3.7 Hz, 1H). $^{13}$C NMR (101 MHz, CDCl$_3$) δ 175.68, 173.78, 157.39, 134.93, 133.33, 128.38, 126.66, 126.38, 126.35, 53.74, 52.39, 45.41, 41.28, 31.95, 28.90, 27.70.

Starting from the intermediate a obtained from the previous step, the synthetic approach was analogous to that described in example 38 to afford the title compound as white solid with a yield of 7%, mp: 122-124° C.

$^1$H NMR (400 MHz, DMSO-d$_6$) δ 8.75-8.50 (m, OH), 7.33 (s, 1H), 7.15 (q, J=6.9, 5.2 Hz, 4H), 6.81 (d, J=9.6 Hz, 2H), 4.64-4.40 (m, 2H), 4.30 (td, J=8.4, 5.0 Hz, 1H), 3.57 (q, J=5.7, 4.6 Hz, 2H), 2.78 (t, =5.7 Hz, 2H), 2.56 (q, J=6.7 Hz, 1H), 2.15 (hept, =7.5 Hz, 2H), 1.88 (dtq, J=32.1, 17.7, 9.7, 8.3 Hz, 2H), 1.58 (dt, =13.3, 6.7 Hz, 1H), 1.25 (ddq, J=31.6, 12.9, 6.7, 6.3 Hz, 2H), 0.90-0.66 (m, 6H). $^{13}$C NMR (101 MHz, DMSO-d$_6$) δ 175.35, 174.11, 156.67, 134.87, 133.97, 128.46, 126.19, 126.15, 125.98, 51.73, 45.17, 40.93, 40.09, 31.48, 28.35, 27.34, 25.15, 22.90, 22.88. HRMS (ESI) calcd for C$_{21}$H$_{32}$BN$_4$O$_4$: 415.25111 [(M−H$_2$O+CH$_2$+H)$^+$], found 415.24994.

Example 50

N-L-phenylalanyl-L-leucine borate-N'-6,7-dimethoxy-1,2,3,4-tetrahydroisoquinoline-urea (cq22)

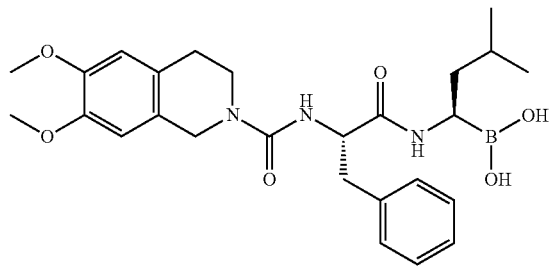 [SMILES: COc1cc2c(cc1OC)CN(C(=O)N[C@@H](Cc1ccccc1)C(=O)N[C@@H](CC(C)C)B(O)O)CC2]

Synthesis of Intermediate a: N-L-phenylalanine methyl ester-N'-6,7-dimethoxy-1,2,3,4-tetrahydroisoquinoline-urea To a solution of carbonyldiimidazole (1.43 g, 8.8 mmol) in 20 mL of DCM was added dropwise a mixed solution of L-phenylalanine methyl ester (1.73 g, 8 mmol) and DIEA (1.4 mL, 8 mmol) in 10 mL of DCM. After 2 h, 6,7-dimethoxy-1,2,3,4-tetrahydroisoquinoline hydrochloride (1.84 g, 8 mmol) and DIEA (1.4 mL, 8 mmol) were added, before overnight reaction. The reaction liquid was washed with water and dried over anhydrous $Na_2SO_4$. Column chromatography was applied to afford 2.0 g of white solid with a yield of 63%, mp: 122-124° C.

$^1$H NMR (400 MHz, $CDCl_3$) δ 7.30-7.22 (m, 3H), 7.15-7.09 (m, 2H), 6.62 (s, 1H), 6.57 (s, 1H), 5.11 (d, J=7.5 Hz, 1H), 4.84 (dt, J=7.6, 5.9 Hz, 1H), 4.50-4.33 (m, 2H), 3.83 (d, =6.7 Hz, 6H), 3.72 (s, 3H), 3.64-3.56 (m, 1H), 3.49 (ddd, =12.3, 6.9, 5.0 Hz, 1H), 3.19-3.07 (m, 2H), 2.82-2.66 (m, 2H). $^{13}$C NMR (101 MHz, $CDCl_3$) δ 173.30, 156.52, 147.65, 147.59, 136.33, 129.26, 128.45, 126.92, 126.68, 124.90, 111.25, 109.17, 55.92, 55.90, 54.48, 52.19, 45.11, 41.27, 38.31, 28.32.

Starting from the intermediate a obtained from the previous step, the synthetic approach was analogous to that described in example 38 to afford the title compound as white solid with a yield of 35%, mp: 112-113° C.

$^1$H NMR (400 MHz, DMSO-$d_6$) δ 8.61 (s, 1H), 7.29-7.12 (m, 5H), 6.81-6.55 (m, 3H), 4.54 (h, J=5.7 Hz, 1H), 4.44-4.26 (m, 2H), 3.70 (d, J=5.3 Hz, 6H), 3.48 (qd, J=9.1, 6.0 Hz, 2H), 3.10-2.88 (m, 2H), 2.61 (dp, J=18.6, 6.7 Hz, 3H), 1.55 (tt, J=13.1, 6.6 Hz, 1H), 1.26 (ddt, J=42.5, 13.5, 7.2 Hz, 2H), 0.80 (dd, J=6.4, 3.8 Hz, 6H). $^{13}$C NMR (101 MHz, DMSO-$d_6$) δ 174.70, 156.52, 147.25, 147.22, 137.88, 129.33, 127.97, 126.38, 126.19, 125.58, 111.95, 109.64, 55.49, 53.52, 44.95, 41.14, 40.22, 37.32, 27.64, 25.09, 23.04, 22.70. HRMS (ESI) calcd for $C_{27}H_{37}BN_3O_5$: 494.28208 [(M−$H_2O$+$CH_2$+H)$^+$], found 494.28207.

Example 51

N-L-phenylalanyl-L-leucine borate-N'-7-methoxy-1,2,3,4-tetrahydroisoquinoline-urea (cq24)

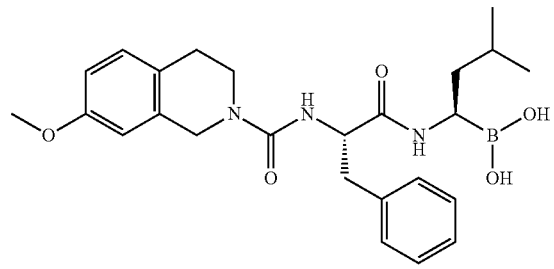 [SMILES: COc1ccc2c(c1)CN(C(=O)N[C@@H](Cc1ccccc1)C(=O)N[C@@H](CC(C)C)B(O)O)CC2]

Synthesis of Precursor I: 7-methoxy-3,4-dihydroisoquinolin-1-one

To 100 mL of anhydrous THF was added p-methoxyphenylethylamine (4.56 g, 30 mmol) and triethylamine (5 mL, 36 mmol), and ethyl chloroformate (3.4 mL, 36 mmol) was added dropwise in an ice bath, before overnight reaction. 100 mL of water was added, THF was evaporated under reduced pressure, and 100 mL of ethyl acetate was added. After liquid partition, the ethyl acetate layer was washed with water two times and dried over anhydrous $Na_2SO_4$. After filtration, the solvent was evaporated under reduced pressure to afford 6.28 g of yellow oil, which was added dropwise into polyphosphoric acid at 120° C. for 30-min reaction. The reaction system was poured into ice water, and extracted with ethyl acetate for three times. The ethyl acetate layer was combined, washed with saturated $NaHCO_3$ until it became basic, and dried over anhydrous $Na_2SO_4$. Column chromatography was applied to afford 1.17 g of white solid with a yield of 22%.

Synthesis of Precursor II: 7-methoxy-1,2,3,4-tetrahydroisoquinoline

To 20 mL of anhydrous THF in an ice bath was slowly added lithium aluminium hydride (0.5 g, 13 mmol), and the precursor 1 (1.14 g, 6.4 mmol) obtained from the previous step was added for 3 h reaction under reflux by heating. To the reaction liquid in an ice bath was sequentially added 0.5 mL of water, 0.5 mL of 15% sodium hydroxide, 1.5 mL of water and some anhydrous magnesium sulfate solid, before 30-min stirring. After filtration, the precipitate was completely washed with THF, and the filtrate was dried over anhydrous $Na_2SO_4$. The solvent was evaporated under reduced pressure to afford 0.98 g of yellow oil, with a yield of 94%.

Starting from the precursor II obtained from the previous step, the synthetic approach of intermediate a (N-L-phenylalanine methyl ester-N'-7-methoxy-1,2,3,4-tetrahydroisoquinoline-urea) was analogous to that described in example 50. Colorless oil was obtained with a yield of 63%.

$^1$H NMR (400 MHz, $CDCl_3$) δ 7.30-7.20 (m, 3H), 7.15-7.09 (m, 2H), 7.03 (d, J=8.4 Hz, 1H), 6.74 (dd, J=8.4, 2.6 Hz, 1H), 6.62 (d, J=2.6 Hz, 1H), 5.03 (d, J=7.5 Hz, 1H), 4.84 (dt, J=7.6, 5.9 Hz, 1H), 4.57-4.35 (m, 2H), 3.76 (s, 3H), 3.72 (s, 3H), 3.58 (ddd, J=12.0, 6.7, 5.1 Hz, 1H), 3.48 (ddd, J=12.2, 6.8, 5.1 Hz, 1H), 3.19-3.07 (m, 2H), 2.75 (q, J=5.5 Hz, 2H). $^{13}$C NMR (101 MHz, $CDCl_3$) δ 173.29, 158.14, 156.55, 136.36, 134.37, 129.33, 129.31, 128.53, 127.02, 126.98, 112.89, 111.19, 55.34, 54.50, 52.26, 45.58, 41.61, 38.41, 28.05.

Starting from the intermediate a obtained from the previous step, the synthetic approach was analogous to that described in example 38 to afford the title compound as white solid with a yield of 24%, mp: 107-109° C.

$^1$H NMR (400 MHz, DMSO-d$_6$) δ 8.82-8.55 (m, 1H), 7.30-7.13 (m, 5H), 7.00 (d, J=8.4 Hz, 1H), 6.82-6.59 (m, 3H), 4.54 (td, J=8.8, 5.2 Hz, 1H), 4.49-4.31 (m, 2H), 3.70 (s, 3H), 3.58-3.40 (m, 2H), 3.09-2.86 (m, 2H), 2.60 (dq, J=19.0, 7.2, 6.4 Hz, 3H), 1.55 (tt, J=12.7, 6.4 Hz, 1H), 1.39-1.16 (m, 2H), 0.80 (td, J=6.5, 5.9, 3.3 Hz, 6H). $^{13}$C NMR (101 MHz, DMSO-d$_6$) δ 174.84, 157.48, 156.51, 137.88, 135.03, 129.40, 129.36, 127.99, 126.57, 126.22, 112.53, 110.78, 54.99, 53.49, 45.44, 41.36, 40.22, 37.32, 27.29, 25.10, 23.05, 22.72. HRMS (ESI) calcd for C$_{26}$H$_{35}$BN$_3$O$_4$: 464.27151 [(M−H$_2$O+CH$_2$+H)$^+$], found 464.27071.

Example 52

N-L-phenylalanyl-L-leucine borate-N'-6-methoxy-1,2,3,4-tetrahydroisoquinoline-urea (cq25)

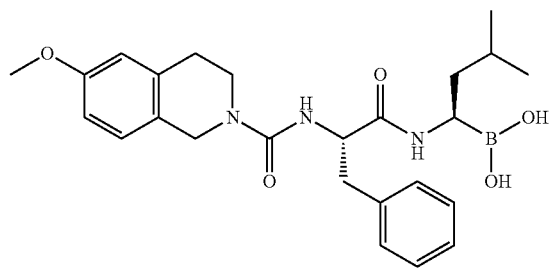 [SMILES: COc1ccc2c(c1)CCN(C(=O)N[C@@H](Cc1ccccc1)C(=O)N[C@@H](CC(C)C)B(O)O)C2]

Using m-methoxy-phenylethylamine as raw material, the synthetic approach of precursor II (6-methoxy-1,2,3,4-tetrahydroisoquinoline) was analogous to that described in example 51. Yellow oil was obtained with a yield of 54%.

Starting from the precursor II obtained from the previous step, the synthetic approach of intermediate a (N-L-phenylalanine methyl ester-N'-6-methoxy-1,2,3,4-tetrahydroisoquinoline-urea) was analogous to that described in example 50. Colorless oil was obtained with a yield of 65%.

$^1$H NMR (400 MHz, CDCl$_3$) δ 7.30-7.21 (m, 3H), 7.14-7.08 (m, 2H), 6.99 (d, J=8.4 Hz, 1H), 6.74 (dd, J=8.4, 2.7 Hz, 1H), 6.67 (d, J=2.6 Hz, 1H), 5.01 (d, J=7.5 Hz, 1H), 4.84 (dt, J=7.5, 5.9 Hz, 1H), 4.51-4.34 (m, 2H), 3.77 (s, 3H), 3.72 (s, 3H), 3.60 (ddd, J=11.9, 6.5, 4.9 Hz, 1H), 3.49 (ddd, J=12.2, 6.8, 5.1 Hz, 1H), 3.20-3.07 (m, 2H), 2.79 (q, J=5.6 Hz, 2H). $^{13}$C NMR (101 MHz, CDCl$_3$) δ 173.28, 158.30, 156.57, 136.37, 136.29, 129.33, 128.53, 127.35, 127.02, 125.35, 113.25, 112.49, 55.32, 54.50, 52.25, 44.90, 41.07, 38.42, 29.25.

Starting from the intermediate a obtained from the previous step, the synthetic approach was analogous to that described in example 38 to afford the title compound as white solid was obtained with a yield of 17%, mp: 106-108° C.

$^1$H NMR (400 MHz, DMSO-d$_6$) δ 8.62 (d, J=4.3 Hz, 1H), 7.36-7.08 (m, 5H), 6.97 (d, J=8.4 Hz, 1H), 6.82-6.55 (m, 3H), 4.51 (td, J=8.7, 5.2 Hz, 1H), 4.43-4.24 (m, 2H), 3.70 (s, 3H), 3.45 (t, =5.9 Hz, 2H), 3.10-2.84 (m, 2H), 2.62 (dq, J=10.0, 5.3 Hz, 3H), 1.54 (dq, J=13.4, 6.7 Hz, 1H), 1.24 (dtd, J=33.8, 13.6, 7.2 Hz, 2H), 0.78 (dd, J=6.8, 2.9 Hz, 6H). $^{13}$C NMR (101 MHz, DMSO-d$_6$) δ 174.73, 157.56, 156.47, 137.82, 135.96, 129.29, 127.93, 127.02, 126.16, 125.87, 113.08, 112.24, 54.96, 53.41, 44.68, 40.86, 37.25, 28.41, 25.05, 22.99, 22.67. HRMS (ESI) calcd for C$_{26}$H$_{35}$BN$_3$O$_4$: 464.27151 [(M−H$_2$O+CH$_2$+H)$^+$], found 464.27270.

Example 53

N-L-phenylalanyl-L-leucine borate-N'-8-methoxy-1,2,3,4-tetrahydroisoquinoline-urea (cq26)

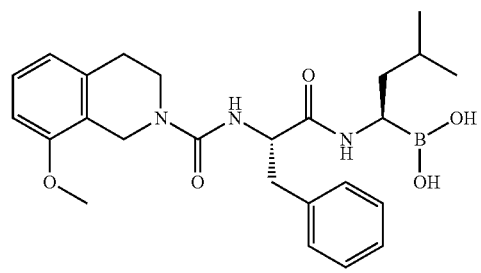 [SMILES: COc1cccc2c1CN(C(=O)N[C@@H](Cc1ccccc1)C(=O)N[C@@H](CC(C)C)B(O)O)CC2]

Using m-methoxy-phenylethylamine as raw material, the synthetic approach of precursor II (8-methoxy-1,2,3,4-tetrahydroisoquinoline) was analogous to that described in example 51. Yellow oil was obtained with a yield of 10%.

Starting from the precursor II obtained from the previous step, the synthetic approach of intermediate a (N-L-phenylalanine methyl ester-N'-8-methoxy-1,2,3,4-tetrahydroisoquinoline-urea) was analogous to that described in example 50. Colorless oil was obtained with a yield of 68%.

$^1$H NMR (400 MHz, CDCl$_3$) δ 7.32-7.04 (m, 7H), 6.71 (dd, J=14.0, 7.9 Hz, 2H), 5.08 (d, S=7.6 Hz, 1H), 4.85 (dt, =7.5, 6.0 Hz, 1H), 4.36 (d, J=2.0 Hz, 2H), 3.81 (s, 3H), 3.70 (s, 3H), 3.68-3.62 (m, 1H), 3.53 (ddd, J=12.5, 6.9, 5.0 Hz, 1H), 3.18-3.08 (m, 2H), 2.79 (q, J=5.8 Hz, 2H). $^{13}$C NMR (101 MHz, CDCl$_3$) δ 173.31, 156.69, 155.91, 136.44, 136.14, 129.36, 128.51, 127.13, 126.98, 121.43, 120.79, 107.46, 55.23, 54.55, 52.20, 41.41, 40.48, 38.55, 28.92.

Starting from the intermediate a obtained from the previous step, the synthetic approach was analogous to that described in example 38 to afford the title compound as white solid with a yield of 29%, mp: 108-110° C.

$^1$H NMR (400 MHz, DMSO-d$_6$) δ 8.79-8.51 (m, 1H), 7.28-7.07 (m, 6H), 6.80 (dd, J=18.9, 8.2 Hz, 2H), 6.69 (d, J=7.9 Hz, 1H), 4.55 (td, J=8.7, 5.2 Hz, 1H), 4.32 (q, J=17.4 Hz, 2H), 3.77 (s, 3H), 3.47 (h, J=7.8 Hz, 2H), 2.99 (qd, J=13.4, 7.2 Hz, 2H), 2.63 (h, J=6.9, 6.3 Hz, 3H), 1.55 (dq, J=13.6, 6.7 Hz, 1H), 1.37-1.15 (m, 2H), 0.79 (dd, J=6.7, 3.9 Hz, 6H). $^{13}$C NMR (101 MHz, DMSO-d$_6$) δ 174.82, 156.60, 155.51, 137.88, 135.72, 129.35, 127.96, 126.75, 126.19, 122.01, 120.71, 107.63, 55.15, 53.43, 41.27, 40.60, 40.21, 37.28, 28.21, 25.09, 23.02, 22.71. HRMS (ESI) calcd for C$_{26}$H$_{35}$BN$_3$O$_4$: 464.27151 [(M−H$_2$O+CH$_2$+H)], found 464.27131.

Example 54

N-L-phenylalanyl-L-leucine borate-N'-5-methoxy-1,2,3,4-tetrahydroisoquinoline-urea (cq27)

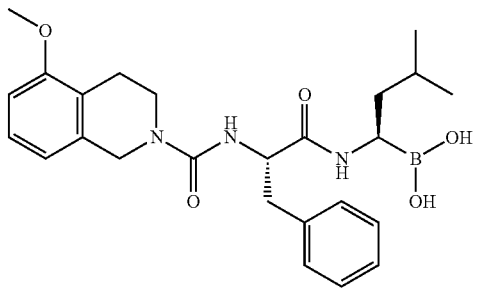 [SMILES: COc1cccc2c1CCN(C(=O)N[C@@H](Cc1ccccc1)C(=O)N[C@@H](CC(C)C)B(O)O)C2]

Using o-methoxy-phenylethylamine as raw material, the synthetic approach of precursor II (5-methoxy-1,2,3,4-tetrahydroisoquinoline) was analogous to that described in example 51. Yellow oil was obtained with a yield of 10%.

Starting from the precursor II obtained from the previous step, the synthetic approach of intermediate a (N-L-phenylalanine methyl ester-N'-5-methoxy-1,2,3,4-tetrahydroisoquinoline-urea) was analogous to that described in example 50. Colorless oil was obtained with a yield of 74%.

$^1$H NMR (400 MHz, CDCl$_3$) δ 7.32-7.21 (m, 3H), 7.17-7.08 (m, 3H), 6.76-6.65 (m, 2H), 5.01 (d, J=7.5 Hz, 1H), 4.84 (dt, =7.6, 5.8 Hz, 1H), 4.48 (q, J=15.9 Hz, 2H), 3.81 (s, 3H), 3.71 (s, 3H), 3.63-3.55 (m, 1H), 3.53-3.44 (m, 1H), 3.19-3.07 (m, 2H), 2.83-2.69 (m, 2H). $^{13}$C NMR (101 MHz, CDCl$_3$) δ 173.26, 156.91, 156.54, 136.37, 134.51, 129.37, 128.56, 127.05, 126.88, 123.66, 118.47, 107.88, 55.39, 54.49, 52.27, 45.46, 41.02, 38.47, 22.59.

Starting from the intermediate a obtained from the previous step, the synthetic approach was analogous to that described in example 38 to afford the title compound as white solid with a yield of 19%, mp: 111-113° C.

$^1$H NMR (400 MHz, DMSO-d$_6$) δ 8.65 (s, 1H), 7.31-7.05 (m, 6H), 6.79 (dd, J=21.9, 8.2 Hz, 2H), 6.67 (d, J=7.8 Hz, 1H), 4.60-4.49 (m, 1H), 4.49-4.27 (m, 2H), 3.75 (s, 3H), 3.49 (q, J=6.5 Hz, 2H), 3.10-2.85 (m, 2H), 2.62 (q, J=7.4, 6.8 Hz, 1H), 2.52 (q, J=5.1, 4.3 Hz, 2H), 1.56 (dt, =13.5, 6.8 Hz, 1H), 1.25 (ddt, J=43.6, 13.9, 7.3 Hz, 2H), 0.78 (dd, J=6.6, 3.4 Hz, 6H). $^{13}$C NMR (101 MHz, DMSO-d$_6$) δ 174.81, 156.64, 156.52, 137.85, 134.98, 129.33, 127.95, 126.55, 126.18, 122.86, 118.16, 107.80, 55.20, 53.45, 45.29, 40.61, 37.27, 25.08, 23.01, 22.67, 22.37. HRMS (ESI) calcd for C$_{26}$H$_{35}$BN$_3$O$_4$: 464.27151 [(M–H$_2$O+CH$_2$+H)$^+$], found 464.27210.

Example 55

N-L-phenylalanyl-L-leucine borate-N'-4,5,6,7-tetrahydrothieno[2,3-c]pyridine-urea (cq29)

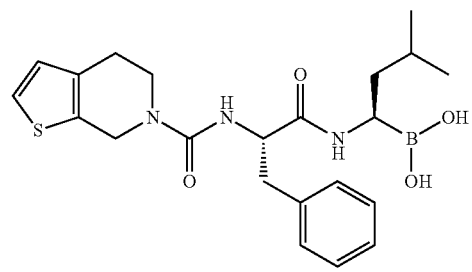 [SMILES: CC(C)C[C@H](NC(=O)[C@H](Cc1ccccc1)NC(=O)N1CCc2ccsc2C1)B(O)O]

Using 4,5,6,7-tetrahydrothieno[2,3-c]pyridine as raw material instead of 6,7-dimethoxy-1,2,3,4-tetrahydroisoquinoline hydrochloride, the synthetic approach of intermediate a (N-L-phenylalanine methyl ester-N'-4,5,6,7-tetrahydrothieno [2,3-c]pyridine-urea) was analogous to that described in example 50. White foam solid was obtained with a yield of 70%.

$^1$H NMR (400 MHz, CDCl$_3$) δ 7.29-7.20 (m, 3H), 7.14-7.08 (m, 3H), 6.74 (d, J=5.2 Hz, 1H), 5.09 (d, J=7.5 Hz, 1H), 4.82 (dt, J=7.5, 5.9 Hz, 1H), 4.49-4.29 (m, 2H), 3.77-3.72 (m, 1H), 3.72 (s, 3H), 3.60 (ddd, J=13.3, 6.7, 4.9 Hz, 1H), 3.20-3.06 (m, 2H), 2.89-2.73 (m, 2H). $^{13}$C NMR (101 MHz, CDCl$_3$) δ 173.27, 156.64, 136.32, 133.65, 131.54, 129.32, 128.54, 127.04, 124.83, 123.28, 54.55, 52.28, 44.23, 41.54, 38.35, 24.98.

Starting from the intermediate a obtained from the previous step, the synthetic approach of intermediate b (N-L-phenylalanine-N'-4,5,6,7-tetrahydrothieno [2,3-c]pyridine-urea) was analogous to that described in example 38. White solid was obtained with a yield of 91%.

Starting from the intermediate b obtained from the previous step, the synthetic approach was analogous to that described in example 46 to afford the title compound as white solid with a yield of 17%, mp: 117-119° C.

$^1$H NMR (400 MHz, DMSO-d$_6$) δ 8.83-8.65 (m, 1H), 7.22 (dtd, J=22.6, 14.9, 6.0 Hz, 6H), 6.94 (d, J=8.4 Hz, 1H), 6.80 (d, J=5.2 Hz, 1H), 4.51 (td, J=8.9, 5.4 Hz, 1H), 4.45-4.24 (m, 2H), 3.58 (q, J=7.2, 6.1 Hz, 2H), 3.08-2.87 (m, 2H), 2.66 (ddt, J=27.9, 13.8, 8.1 Hz, 3H), 1.56 (dt, J=13.4, 6.7 Hz, 1H), 1.38-1.13 (m, 2H), 0.79 (dd, J=6.5, 3.5 Hz, 6H). $^{13}$C NMR (101 MHz, DMSO-d$_6$) δ 174.88, 156.62, 137.91, 132.99, 132.73, 129.34, 127.98, 126.21, 125.07, 123.25, 53.57, 43.83, 41.39, 40.21, 37.27, 25.11, 24.44, 23.06, 22.71. HRMS (ESI) calcd for C$_{23}$H$_{31}$BN$_3$O$_3$S: 440.21737 [(M–H$_2$O+CH$_2$+H)$^+$], found 440.21765.

Test Example 1

The Inhibitory Effects of Urea Peptidomimetic Boronic Compounds on the Proteasome 1 μg of 20S proteasome extracted from rat liver was incubated with a 100 μL solution containing various concentrations of the present compounds, 50 μM fluorescent peptides and 20 mM Tris-HCl at 37° C. for 1 h, respectively. The fluorescence released from AMC and βNA reagents was measured by a spectrofluorimeter Fluostar OPTIMA and BMG Germany at excitation/emission wavelengths of 380/440 nm and 335/410 nm, respectively. 0.1% DMSO was used as a solvent control. Compared with the fluorescence of solvent control, an inhibition rate or IC$_{50}$ value was calculated. Said assays used anticancer drug bortezomib (leukemia drug, namely PS341) as compound for positive control. The results are shown in Table 1 and Table 3.

Test Example 2

The Preliminary Screening Tests of Anti-tumor Activities In Vitro

The test methods used in this test example are routine methods for anti-tumor activities test in pharmaceutical area, for example, referring to the following reference: (J. Immunol Method, 1983, 65, 55).

Test models: A: MTT method (Hela, human cervical carcinoma); B: SRB method (BGC-823, liver cancer); C:

SRB method (MCF-7, breast cancer); D: SRB method (A549, human lung cancer); E: SRB method (PC3M1E8, prostate cancer).

Inhibition rates of the compounds were measured under concentrations of 0.1 μM, 1 μM or 10 μM. The results are shown in Table 2.

Test Example 3

Anti-tumor Activities In Vitro ($IC_{50}$)

Cancer cells were cultured in vitro. When cell growth reached logarithmic phase, the cells were collected and centrifuged at 1000 rpm for 5 min, before the supernate was removed and the cells were suspended in a moderate amount of medium, and then the concentration of cell was adjusted to $3.5 \times 10^4$/mL. The cell suspension was added into a 96-well plate with 100 μL per well and cultured in a cell incubator (37° C., 5% $CO_2$) for 24 h. Then test drugs of different end concentrations were added, and the negative control group was added DMSO (end concentration was 0.5%), while each group afforded three repetitive holes. After cultivation for another 72 h in the cell incubator, a solution containing 5 mg/ml MTT (20 μL) was added into each well and the 96-well plate was placed at 37° C. for 3 h. To each well was added 150 μL DMSO, after oscillation in a shaking table for 5 min, the optical density (OD) values at 492 nm/620 nm were measured. $IC_{50}$ values were calculated by Prism Graphpad statistical software. The results are shown in Table 4, Table 5 and Table 6.

TABLE 1 inhibition of the present compounds on proteasome

| Examples No | concentrations μM | inhibition rates (%) CT-L | PGPH | T-L |
|---|---|---|---|---|
| 1 | 0.2 | 33.819 | 40.869 | −6.549 |
|  | 2 | 86.790 | 87.942 | 22.848 |
|  | 20 | 93.571 | 96.585 | 35.456 |
| 3 | 0.2 | −20.774 | 7.375 | 16.864 |
|  | 2 | 1.913 | 40.763 | 18.480 |
|  | 20 | 68.636 | 88.360 | 35.865 |
| 4 | 0.2 | −14.170 | 2.030 | 6.916 |
|  | 2 | 10.372 | 2.190 | 4.381 |
|  | 20 | 77.749 | 62.706 | 36.157 |
| 5 | 0.2 | −17.752 | 2.666 | −5.231 |
|  | 2 | −15.111 | 3.148 | −1.516 |
|  | 20 | −3.128 | 9.712 | 0.968 |
| 6 | 0.2 | −0.670 | 17.405 | −3.924 |
|  | 2 | 44.666 | 66.342 | 2.409 |
|  | 20 | 86.789 | 93.833 | 27.157 |
| 7 | 0.2 | 23.366 | 5.764 | −16.500 |
|  | 2 | 47.217 | 1.949 | −12.616 |
|  | 20 | 82.623 | 0.485 | 25.314 |
| 8 | 0.2 | 2.873 | 1.617 | −1.392 |
|  | 2 | 59.740 | 7.355 | 9.321 |
|  | 20 | 89.418 | 63.069 | 30.580 |
| 9 | 0.2 | −12.230 | 1.666 | 1.544 |
|  | 2 | 44.893 | 6.259 | 8.997 |
|  | 20 | 76.811 | 34.069 | 21.539 |
| 10 | 0.2 | −4.193 | 18.952 | −12.271 |
|  | 2 | 47.804 | 79.767 | −5.926 |
|  | 20 | 89.050 | 95.963 | 17.397 |
| 11 | 0.2 | 5.785 | 12.760 | −8.060 |
|  | 2 | 52.830 | 32.649 | −5.632 |
|  | 20 | 92.527 | 81.000 | 25.191 |
| 13 | 0.2 | 45.429 | 5.276 | −3.113 |
|  | 2 | 91.338 | 53.430 | 13.827 |
|  | 20 | 95.363 | 96.778 | 49.369 |
| 12 | 0.2 | 63.305 | 9.760 | −7.933 |
|  | 2 | 93.361 | 73.204 | 34.743 |
|  | 20 | 95.804 | 96.668 | 67.841 |

TABLE 1-continued inhibition of the present compounds on proteasome

| Examples No | concentrations μM | inhibition rates (%) CT-L | PGPH | T-L |
|---|---|---|---|---|
| 14 | 0.2 | 82.082 | 6.461 | 5.043 |
|  | 2 | 96.113 | 84.581 | 57.790 |
|  | 20 | 98.939 | 97.009 | 88.422 |
| 15 | 0.2 | 86.338 | 8.450 | 5.722 |
|  | 2 | 95.861 | 89.392 | 53.491 |
|  | 20 | 98.260 | 96.783 | 90.406 |
| 16 | 0.2 | −14.639 | −14.446 | −2.888 |
|  | 2 | 86.614 | −2.926 | 12.266 |
|  | 20 | 94.466 | 92.371 | 62.166 |
| 17 | 0.2 | 10.548 | 3.748 | −3.766 |
|  | 2 | 87.304 | 8.575 | 10.537 |
|  | 20 | 95.808 | 94.509 | 57.290 |
| 18 | 0.2 | 82.067 | 9.814 | 4.990 |
|  | 2 | 96.655 | 68.776 | 56.881 |
|  | 20 | 98.316 | 97.104 | 91.019 |
| 19 | 0.2 | 91.708 | 16.882 | 18.247 |
|  | 2 | 97.264 | 82.273 | 69.061 |
|  | 20 | 98.294 | 97.207 | 90.652 |
| 20 | 0.2 | 91.940 | −23.048 | 35.572 |
|  | 2 | 96.544 | −26.615 | 83.660 |
|  | 20 | 97.046 | −28.863 | 92.573 |
| 21 | 0.2 | 47.308 | 8.577 | 0.355 |
|  | 2 | 90.946 | 62.467 | 29.284 |
|  | 20 | 95.637 | 96.876 | 61.959 |
| 22 | 0.2 | 61.963 | 10.065 | −3.948 |
|  | 2 | 89.674 | 7.173 | 28.328 |
|  | 20 | 93.282 | 5.295 | 53.051 |
| 23 | 0.2 | 49.489 | −13.661 | −0.748 |
|  | 2 | 90.992 | −20.492 | 47.155 |
|  | 20 | 94.189 | −20.304 | 90.533 |
| 24 | 0.2 | 84.643 | −21.838 | −0.926 |
|  | 2 | 95.724 | −24.724 | 43.457 |
|  | 20 | 97.372 | −24.249 | 90.250 |
| positive control | 0.01 | 26.691 | −1.782 | 0.826 |
|  | 0.1 | 91.554 | 55.563 | 33.278 |
|  | 1 | 94.845 | 95.726 | 61.359 |

TABLE 2 activity results on cellular level

| Examples No | concentrations μM | inhibition rates (%) Hela | BGC-823 | MCF-7 | A549 |
|---|---|---|---|---|---|
| 1 | 0.1 | 8.67 | 7.79 | 1.00 | 1.44 |
|  | 1 | 28.02 | 14.88 | 7.46 | 35.28 |
|  | 10 | 38.51 | 31.99 | 22.86 | 50.16 |
| 3 | 0.1 | 10.23 | 4.73 | 3.24 | 5.55 |
|  | 1 | 14.22 | −4.01 | 9.52 | 16.65 |
|  | 10 | 19.22 | 0.96 | 9.37 | 14.87 |
| 4 | 0.1 | 9.59 | 6.67 | 6.46 | 6.40 |
|  | 1 | 11.28 | 4.64 | 9.07 | 16.20 |
|  | 10 | 25.35 | 13.07 | 9.93 | 31.09 |
| 5 | 0.1 | 7.42 | 5.47 | 6.37 | 3.25 |
|  | 1 | 10.31 | 3.19 | 8.84 | 10.26 |
|  | 10 | 21.83 | 8.66 | 8.44 | 30.29 |
| 6 | 0.1 | 1.74 | 4.88 | 0.80 | −6.94 |
|  | 1 | 4.43 | 4.40 | 1.90 | −3.91 |
|  | 10 | 16.86 | 8.98 | 6.05 | 7.01 |
| 7 | 0.1 | 0.48 | 2.21 | 4.81 | −1.53 |
|  | 1 | 5.11 | 0.62 | 7.40 | 2.54 |
|  | 10 | 14.88 | 6.88 | 11.74 | 15.51 |
| 8 | 0.1 | 12.65 | 4.74 | 4.54 | 1.01 |
|  | 1 | 13.43 | 5.62 | 8.51 | 8.26 |
|  | 10 | 32.88 | 15.64 | 16.38 | 39.24 |
| 9 | 0.1 | 11.82 | 8.33 | 6.66 | 4.05 |
|  | 1 | 14.29 | 7.84 | 11.74 | 10.32 |
|  | 10 | 32.14 | 14.72 | 13.81 | 36.21 |

TABLE 2-continued activity results on cellular level

| Examples No | concentrations μM | inhibition rates (%) Hela | BGC-823 | MCF-7 | A549 |
|---|---|---|---|---|---|
| 10 | 0.1 | 11.76 | 4.44 | 8.10 | 3.45 |
|  | 1 | 14.79 | 7.38 | 12.68 | 14.64 |
|  | 10 | 27.00 | 16.43 | 15.97 | 25.01 |
| 11 | 0.1 | 2.45 | 6.32 | 4.81 | −4.49 |
|  | 1 | 6.10 | 4.58 | 7.23 | 0.81 |
|  | 10 | 19.24 | 13.10 | 16.11 | 26.64 |
| 13 | 0.1 | 7.02 | 3.66 | −3.69 | −9.11 |
|  | 1 | 20.25 | 17.81 | 8.39 | 23.49 |
|  | 10 | 37.74 | 40.00 | 19.97 | 50.53 |
| 12 | 0.1 | 12.01 | 6.01 | 1.77 | 1.55 |
|  | 1 | 35.04 | 36.33 | 26.31 | 45.54 |
|  | 10 | 46.04 | 50.21 | 50.75 | 69.67 |
| 14 | 0.1 | 40.31 | 12.86 | 51.92 | 2.67 |
|  | 1 | 43.20 | 33.50 | 67.76 | 13.00 |
|  | 10 | 53.50 | 38.25 | 72.16 | 33.30 |
| 15 | 0.1 | 39.26 | 7.38 | 47.66 | 2.63 |
|  | 1 | 44.50 | 32.56 | 65.03 | 11.04 |
|  | 10 | 51.78 | 38.36 | 73.80 | 31.12 |
| 16 | 0.1 | 9.91 | 6.01 | 6.62 | 5.00 |
|  | 1 | 34.14 | 34.04 | 27.16 | 36.21 |
|  | 10 | 39.61 | 48.72 | 51.39 | 65.05 |
| 17 | 0.1 | 12.09 | 7.89 | 8.29 | 5.46 |
|  | 1 | 34.62 | 27.06 | 26.16 | 40.93 |
|  | 10 | 51.48 | 52.71 | 37.56 | 65.95 |
| 18 | 0.1 | 37.82 | 41.44 | 25.75 | 44.27 |
|  | 1 | 39.58 | 46.57 | 37.45 | 63.51 |
|  | 10 | 46.49 | 50.00 | 47.81 | 66.01 |
| 19 | 0.1 | 39.83 | 43.74 | 23.45 | 53.13 |
|  | 1 | 43.99 | 46.57 | 38.07 | 65.60 |
|  | 10 | 55.03 | 57.22 | 61.72 | 76.14 |
| 20 | 0.1 | 17.42 | 50.03 | 32.17 | 64.98 |
|  | 1 | 42.54 | 47.12 | 42.23 | 68.15 |
|  | 10 | 75.69 | 50.17 | 45.50 | 69.33 |
| 21 | 0.1 | 9.87 | 0.38 | 5.41 | 7.42 |
|  | 1 | 12.91 | 2.21 | 9.64 | 25.20 |
|  | 10 | 29.88 | 23.14 | 24.19 | 41.42 |
| 22 | 0.1 | 8.66 | 2.04 | 7.17 | 1.88 |
|  | 1 | 19.70 | 9.01 | 12.74 | 28.28 |
|  | 10 | 43.40 | 44.52 | 42.19 | 65.60 |
| 23 | 0.1 | 17.42 | 43.22 | 23.66 | 32.71 |
|  | 1 | 42.54 | 42.71 | 55.96 | 68.85 |
|  | 10 | 75.69 | 81.56 | 73.01 | 81.35 |
| 24 | 0.1 | 24.70 | 36.34 | 19.68 | 29.47 |
|  | 1 | 45.30 | 45.60 | 33.28 | 61.47 |
|  | 10 | 48.63 | 51.06 | 45.14 | 70.23 |
| positive control | 0.1 | 41.63 | 40.96 | 27.59 | 59.85 |
|  | 1 | 43.25 | 43.56 | 32.78 | 63.81 |
|  | 10 | 47.32 | 46.78 | 40.68 | 66.14 |

TABLE 3 activity results on enzymatic level

| Examples No | IC$_{50}$ (μM) T-L | CT-L | PGPH |
|---|---|---|---|
| 25 | 1.05 | 0.02 | 0.24 |
| 26 | 0.61 | 0.01 | 0.07 |
| 27 | 6.98 | 0.20 | 0.28 |
| 28 | 2.38 | 0.0000002 | 0.02 |
| 29 | 0.19 | 0.002 | 0.03 |
| 30 | 0.34 | 0.004 | 0.13 |
| 2 | 11.40 | 0.05 | 0.79 |
| 31 | 0.53 | 0.04 | 0.48 |
| 32 | 1.15 | 0.0003 | 0.24 |
| 33 | 5.32 | 0.02 | 0.08 |
| 34 | 0.15 | 0.012 | 0.12 |
| 35 | 0.34 | 0.002 | 0.11 |

TABLE 3-continued activity results on enzymatic level

| Examples No | IC$_{50}$ (μM) T-L | CT-L | PGPH |
|---|---|---|---|
| 36 | 0.19 | 0.003 | 0.14 |
| 37 | >20 | 0.66 | 1.24 |
| positive control | 0.44 | 0.004 | 0.03 |

TABLE 4 the inhibitory activities on growth of liver cancer and stomach cancer cells

| Examples No | IC$_{50}$ (μM) HepG2 | MGC803 | Example No | IC$_{50}$ (μM) HepG2 | MGC803 |
|---|---|---|---|---|---|
| 25 | 0.07086 | 0.03001 | 34 | 0.05308 | 0.007062 |
| 26 | 0.03699 | 0.004084 | 35 | 0.03882 | 0.006698 |
| 27 | 1.072 | 0.1982 | 36 | 0.04381 | 0.006317 |
| 28 | 0.01938 | 0.003962 | 37 | 0.05967 | 0.007298 |
| 29 | 0.03049 | 0.005203 | 14 | 0.08725 | 0.01876 |
| 30 | 0.04468 | 0.006298 | 15 | 0.2501 | 0.03599 |
| 2 | 4.136 | 0.7382 | 18 | 0.05284 | 0.01065 |
| 31 | 0.07067 | 0.02887 | 20 | 0.03781 | 0.007329 |
| 32 | 0.03725 | 0.005873 | positive control | 0.03657 | 0.005782 |
| 33 | 0.04560 | 0.005316 |  |  |  |

TABLE 5 the inhibitory activities of three compounds on various human cancer cells (IC$_{50}$)

| No | cell line | Example 20 (nM) | Example 28 (nM) | Example 35 (nM) | Positive control (nM) |
|---|---|---|---|---|---|
| 1 | A549 | 1022.61 | 3826.15 | 1317.50 | 2135.73 |
| 2 | 95D | 40.96 | 37.11 | 58.85 | 38.18 |
| 3 | HCT116 | 23.02 | 7.32 | 16.07 | 1.40 |
| 4 | HL-60 | 26.96 | 7.71 | 28.53 | 7.60 |
| 5 | MGC803 | 17.52 | 4.98 | 16.73 | 6.54 |
| 6 | Hela | 117.14 | 531.77 | 254.63 | 224.48 |
| 7 | BEL7404 | 42.23 | 13.75 | 47.26 | 25.04 |
| 8 | MKN45 | 20.11 | 15.52 | 26.62 | 7.15 |
| 9 | SKOV3 | 46.30 | 25.88 | 10.47 | 1.62 |
| 10 | MDA-MB-231 | 25.08 | 17.74 | 28.40 | 16.65 |
| 11 | HepG2 | 25.96 | 8.38 | 19.04 | 1.61 |
| 12 | SW1990 | 80.33 | 89.34 | 90.73 | 79.06 |

TABLE 6 the inhibitory activities on growth of stomach cancer cells (MGC80-3)

| Example No | IC$_{50}$ (μM) |
|---|---|
| 38 | 0.1366 ± 0.011 |
| 39 | 0.1393 ± 0.004 |
| 40 | 0.1627 ± 0.008 |
| 41 | 0.1342 ± 0.003 |
| 42 | 0.1427 ± 0.004 |
| 43 | 0.0173 ± 0.003 |
| 44 | 0.1390 ± 0.004 |
| 45 | 0.0092 ± 0.001 |
| 46 | 0.0046 ± 0.000 |
| 47 | 0.0244 ± 0.005 |
| 48 | 0.1109 ± 0.009 |
| 49 | 0.0401 ± 0.005 |

TABLE 6-continued the inhibitory activities on growth
of stomach cancer cells (MGC80-3)

| Example No | IC$_{50}$ (μM) |
|---|---|
| 50 | 0.0172 ± 0.002 |
| 51 | >100 |
| 52 | 0.8503 ± 0.106 |
| 53 | 2.242 ± 0.503 |
| 54 | 0.3606 ± 0.088 |
| 55 | 0.0060 ± 0.000 |
| 56 | 0.0052 ± 0.001 |
| 57 | 0.00025 ± 0.000 |
| 58 | 0.0065 ± 0.002 |
| 59 | 0.0057 ± 0.000 |
| 60 | 0.0079 ± 0.001 |
| positive control | 0.0057 ± 0.001 |

The invention claimed is:

1. A compound of formula (I):

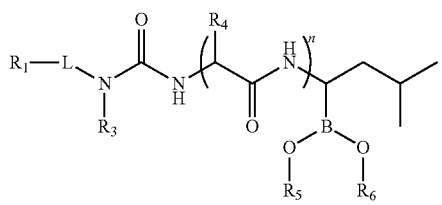

or a pharmaceutically acceptable salt or solvate thereof, wherein:

n represents the number of amino acid residues, and n is 1 or 2;

$R_4$ is a side chain of amino acids independently selected from the group consisting of hydrogen, aralkyl, heteroaralkyl, heterocycloalkyl, and alkyl, wherein the above aralkyl, heteroaralkyl, heterocycloalkyl or alkyl each can be optionally substituted by one or more substituents independently selected from the group consisting of alkyl, cycloalkyl, alkenyl, cycloalkenyl, alkynyl, aryl, aralkyl, heteroaryl, heteroaralkyl, heterocyclyl, heterocycloalkyl, alkoxy, cycloalkoxy, aryloxy, alkylthio, cycloalkylthio, arylthio, alkoxycarbonyl, aryloxycarbonyl, acyl, thioacyl, acyloxy, amido, carbamido, sulfinyl, alkylsulfonyl, arylsulfonyl, haloalkyl, carbamoyl, halogen, cyano, isocyano, nitro, nitroso, thiocyano, isothiocyano, acylhydrazino, thioalkyl, sulpho and silyl;

$R_5$ and $R_6$ are hydrogen at the same time, or together $R_5$ and $R_6$ form a diol ester group;

$R_1$, L and $R_3$ together with N atom to which L and $R_3$ are attached form a 5, 6 or 7 membered heterocyclic ring optionally having, in addition to the nitrogen atom, another ring heteroatom being N, and optionally having an oxo group; meanwhile, the 5, 6 or 7 membered heterocyclic ring above is fused to an aromatic ring or heteroaromatic ring each optionally substituted by one or more substituents independently selected from the group consisting of alkyl, cycloalkyl, alkenyl, cycloalkenyl, alkynyl, aryl, aralkyl, heteroaryl, heteroaralkyl, heterocyclyl, heterocycloalkyl, alkoxy, cycloalkoxy, aryloxy, alkylthio, cycloalkylthio, arylthio, alkoxycarbonyl, aryloxycarbonyl, acyl, thioacyl, acyloxy, amido, carbamido, sulfinyl, alkylsulfonyl, arylsulfonyl, haloalkyl, carbamoyl, halogen, cyano, isocyano, nitro, nitroso, thiocyano, isothiocyano, acylhydrazino, thioalkyl, sulpho and silyl.

2. The compound or a pharmaceutically acceptable salt or solvate thereof according to claim 1, wherein:

$R_4$ is a side chain of amino acids independently selected from hydrogen, phenyl $C_1$-$C_4$ alkyl, heteroaryl $C_1$-$C_4$ alkyl, heterocyclyl $C_1$-$C_4$ alkyl, $C_1$-$C_4$ alkyl or naphthyl $C_1$-$C_4$ alkyl, wherein the above phenyl $C_1$-$C_4$ alkyl, heteroaryl $C_1$-$C_4$ alkyl, heterocyclyl $C_1$-$C_4$ alkyl, $C_1$-$C_4$ alkyl or naphthyl $C_1$-$C_4$ alkyl can be optionally substituted by one or more substituents independently selected from the group consisting of carbamoyl, nitro and nitroso;

$R_5$ and $R_6$ are hydrogen at the same time, or together $R_5$ and $R_6$ form a cyclic diol ester group;

$R_1$, L and $R_3$ together with N atom to which L and $R_3$ are attached form a 5, 6 or 7 membered heterocyclic ring optionally having, in addition to the nitrogen atom, another ring heteroatom being N, and optionally having an oxo group; meanwhile, the 5, 6 or 7 membered heterocyclic ring is fused to a benzene ring, a naphthalene ring or a heteroaromatic ring, wherein the benzene ring, naphthalene ring or heteroaromatic ring each is optionally substituted by one or more substituents independently selected from the group consisting of alkyl, cycloalkyl, alkenyl, cycloalkenyl, alkynyl, aryl, aralkyl, heteroaryl, heteroaralkyl, heterocyclyl, heterocycloalkyl, alkoxy, cycloalkoxy, aryloxy, alkylthio, cycloalkylthio, arylthio, alkoxycarbonyl, aryloxycarbonyl, acyl, thioacyl, acyloxy, amido, carbamido, sulfinyl, alkylsulfonyl, arylsulfonyl, haloalkyl, carbamoyl, halogen, cyano, isocyano, nitro, nitroso, thiocyano, isothiocyano, acylhydrazino, thioalkyl, sulpho and silyl.

3. The compound or a pharmaceutically acceptable salt or solvate thereof according to claim 1, wherein:

$R_4$ is independently selected from hydrogen, benzyl, isobutyl, s-butyl, isopropyl, methyl, carbamoylethyl, nitrobenzyl, phenylethyl, naphthylmethyl or benzopyrrolylmethyl;

$R_5$ and $R_6$ are hydrogen at the same time, or together $R_5$ and $R_6$ form a pinanediol ester or a pinacol ester group;

$R_1$, L and $R_3$ together with N atom to which L and $R_3$ are attached form a 5, 6 or 7 membered heterocyclic ring optionally having, in addition to the nitrogen atom, another ring heteroatom being N, and optionally having an oxo group; meanwhile, the 5, 6 or 7 membered heterocyclic ring is fused to a benzene ring, a naphthalene ring or a heteroaromatic ring, wherein the benzene ring, naphthalene ring or heteroaromatic ring can be optionally substituted by one or more substituents independently selected from the group consisting of $C_1$-$C_4$ alkoxy, nitro and nitroso.

4. The compound or a pharmaceutically acceptable salt or solvate thereof according to claim 1, wherein:

$R_4$ is independently selected from hydrogen, benzyl, isobutyl, s-butyl, isopropyl, methyl, carbamoylethyl, nitrobenzyl, phenylethyl, naphthylmethyl or benzopyrrolylmethyl;

$R_5$ and $R_6$ are hydrogen at the same time, or together $R_5$ and $R_6$ form a pinanediol ester or a pinacol ester group;

$R_1$, L and $R_3$ together with N atom to which L and $R_3$ are attached form a piperidine ring optionally having an oxo group; meanwhile, the piperidine ring is fused to a benzene ring optionally substituted by one or more substituents independently selected from the group consisting of methoxy and nitro.

5. The compound or a pharmaceutically acceptable salt or solvate thereof of claim 1, wherein said compound is selected from the group consisting of:
(28) N-L-phenylalanyl-L-leucine borate-N'-1,2,3,4-tetrahydroisoquinoline-urea;
(37) N-(1-oxo-1,2,3,4-dihydroisoquinolin-2-ylformyl)-L-phenylalanyl-L-leucine borate;
(38) N-L-phenylalanyl-L-leucine borate-N'-1,2,3,4-tetrahydroquinoline-urea;
(39) N-L-phenylalanyl-L-leucine borate-N'-1-methyl-1,2,3,4-tetrahydroisoquinoline-urea;
(40) N-L-leucyl-L-leucine borate-N'-1,2,3,4-tetrahydroisoquinoline-urea;
(41) N-L-alanyl-L-leucine borate-N'-1,2,3,4-tetrahydroisoquinoline-urea;
(42) N-L-valyl-L-leucine borate-N'-1,2,3,4-tetrahydroisoquinoline-urea;
(43) N-L-naphthylalanyl-L-leucine borate-N'-1,2,3,4-tetrahydroisoquinoline-urea;
(44) N-L-isoleucyl-L-leucine borate-N'-1,2,3,4-tetrahydroisoquinoline-urea;
(45) N-L-tryptophanyl-L-leucine borate-N'-1,2,3,4-tetrahydroisoquinoline-urea;
(46) N-L-phenylalanyl-L-leucine borate-N'-7-nitro-1,2,3,4-tetrahydroisoquinoline-urea;
(47) N-L-homophenylalanyl-L-leucine borate-N'-1,2,3,4-tetrahydroisoquinoline-urea;
(48) N-L-4-nitro-phenylalanyl-L-leucine borate-N'-1,2,3,4-tetrahydroisoquinoline-urea;
(49) N-L-glutamyl-L-leucine borate-N'-1,2,3,4-tetrahydroisoquinoline-urea;
(50) N-L-phenylalanyl-L-leucine borate-N'-6,7-dimethoxy-1,2,3,4-tetrahydroisoquinoline-urea;
(51) N-L-phenylalanyl-L-leucine borate-N'-7-methoxy-1,2,3,4-tetrahydroisoquinoline-urea;
(52) N-L-phenylalanyl-L-leucine borate-N'-6-methoxy-1,2,3,4-tetrahydroisoquinoline-urea;
(53) N-L-phenylalanyl-L-leucine borate-N'-8-methoxy-1,2,3,4-tetrahydroisoquinoline-urea;
(54) N-L-phenylalanyl-L-leucine borate-N'-5-methoxy-1,2,3,4-tetrahydroisoquinoline-urea; and
(55) N-L-phenylalanyl-L-leucine borate-N'-4,5,6,7-tetrahydrothieno [2,3-c]pyridine-urea.

6. A method for preparation of the compound according to claim 1, wherein: the compound is prepared according to process (B);
the process (B) comprising:
(B1) formation of carbamido group by coupling;

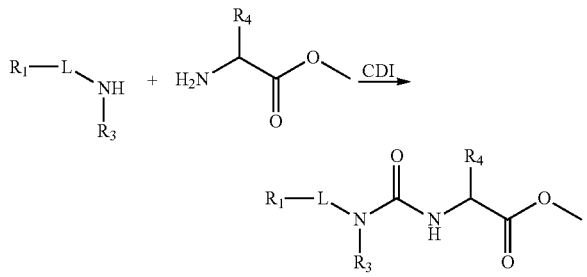

(B2) hydrolysis of methyl ester group;

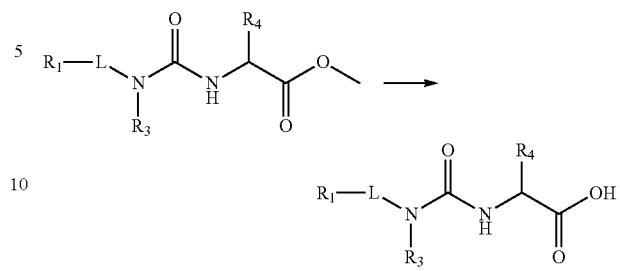

(B3) formation of amido group;

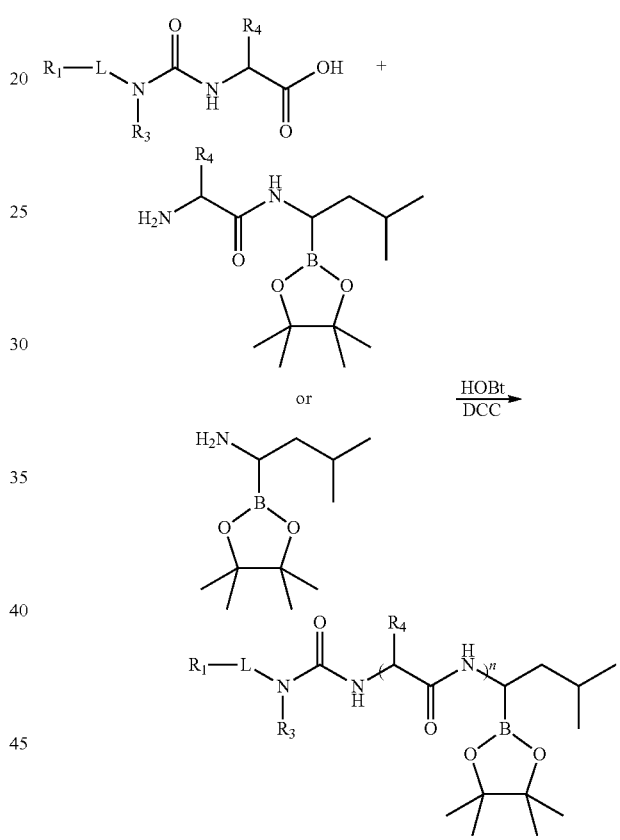

(B4) optionally forming boronic acid compounds or diol ester compounds;
optionally hydrolyzing the pinacol ester obtained by step (B3) to obtain the corresponding boronic acid compound; optionally, further esterifying the boronic acid compound with a diol, to obtain the corresponding diol ester compounds.

7. A method of inhibiting a cancer comprising:
administrating the compound or a pharmaceutically acceptable salt or solvate thereof according to claim 1 to a subject that has cancer.

8. The method according to claim 7, wherein said cancer is selected from the group consisting of lung cancer, breast cancer, liver cancer, gastric cancer, cervical cancer, colon cancer, leukemia, ovarian cancer, pancreatic cancer and epithelial cancer.

* * * * *